(12) United States Patent
Petroff et al.

(10) Patent No.: US 11,278,206 B2
(45) Date of Patent: Mar. 22, 2022

(54) MICRO-OPTIC PROBES FOR NEUROLOGY

(71) Applicant: GENTUITY, LLC, Sudbury, MA (US)

(72) Inventors: Christopher Petroff, Groton, MA (US);
Michael Atlas, Arlington, MA (US);
David Kolstad, Carlisle, MA (US);
Christopher Petersen, Carlisle, MA (US); Nareak Douk, Lowell, MA (US);
J. Christopher Flaherty, Auburndale, FL (US)

(73) Assignee: Gentuity, LLC, Sudbury, MA (US)

( * ) Notice: Subject to any disclaimer, the term of this patent is extended or adjusted under 35 U.S.C. 154(b) by 676 days.

(21) Appl. No.: 15/566,041

(22) PCT Filed: Apr. 15, 2016

(86) PCT No.: PCT/US2016/027764
§ 371 (c)(1),
(2) Date: Oct. 12, 2017

(87) PCT Pub. No.: WO2016/168605
PCT Pub. Date: Oct. 20, 2016

(65) Prior Publication Data
US 2018/0125372 A1    May 10, 2018

Related U.S. Application Data

(60) Provisional application No. 62/322,182, filed on Apr. 13, 2016, provisional application No. 62/148,355, filed on Apr. 16, 2015.

(51) Int. Cl.
*A61B 5/00* (2006.01)
*A61B 1/07* (2006.01)
(Continued)

(52) U.S. Cl.
CPC .............. *A61B 5/0084* (2013.01); *A61B 1/07* (2013.01); *A61B 5/6852* (2013.01);
(Continued)

(58) Field of Classification Search
CPC ....... A61B 1/07; A61B 5/0084; A61B 5/0059; A61B 5/0062; A61B 5/0066;
(Continued)

(56) References Cited

U.S. PATENT DOCUMENTS 4,554,929 A   11/1985   Samson et al.
4,566,330 A    1/1986   Fujii et al.
(Continued)

FOREIGN PATENT DOCUMENTS

AU   2014200116    1/2014
CN      1684624   10/2005
(Continued)

OTHER PUBLICATIONS

Abozenadah, H., Bishop, A., Bittner, S., Lopez, O., Wiley, C., and Flatt, P.M. (2017) Consumer Chemistry: How Organic Chemistry Impacts Our Lives. CC BY-NC-SA. Available at: https://wou.edu/chemistry/courses/online-chemistry-textbooks/ch105-consumer-chemistry/.*

(Continued)

*Primary Examiner* — Carolyn A Pehlke
(74) *Attorney, Agent, or Firm* — Onello & Mello, LLP

(57) ABSTRACT

An imaging system for a patient comprises an imaging probe. The imaging probe comprises: an elongate shaft for insertion into the patient and comprising a proximal end, a distal portion, and a lumen extending between the proximal end and the distal portion; a rotatable optical core comprising a proximal end and a distal end, the rotatable optical core configured to optically and mechanically connect with an interface unit; a probe connector positioned on the elongate (Continued)

shaft proximal end and surrounding at least a portion of the rotatable optical core and an optical assembly positioned in the elongate shaft distal portion and proximate the rotatable optical core distal end, the optical assembly configured to direct light to tissue and collect reflected light from the tissue. A shear-thinning fluid can be provided between the elongate shaft and the rotatable optical core, such as to reduce undesired rotational variations of the rotatable optical core.

40 Claims, 10 Drawing Sheets

(51) Int. Cl.
    *G02B 6/36* (2006.01)
    *C10M 171/02* (2006.01)
(52) U.S. Cl.
    CPC .......... *G02B 6/3604* (2013.01); *A61B 5/0042* (2013.01); *C10M 171/02* (2013.01)
(58) Field of Classification Search
    CPC ... A61B 5/6852; A61B 5/6867; A61B 5/6868; A61B 5/0042; C10M 171/02; G02B 6/36; G02B 6/3604; G02B 6/3624
    See application file for complete search history.

(56) References Cited

U.S. PATENT DOCUMENTS

| | | |
|---|---|---|
| 4,583,184 A | 4/1986 | Murase |
| 4,594,895 A | 6/1986 | Fujii |
| 4,597,292 A | 7/1986 | Fujii et al. |
| 4,646,748 A | 3/1987 | Fujii et al. |
| 4,753,248 A | 6/1988 | Engler et al. |
| 4,957,482 A * | 9/1990 | Shiber ............ A61B 17/22012 604/22 |
| 4,961,427 A | 10/1990 | Namekawa et al. |
| 5,002,059 A | 3/1991 | Crowley et al. |
| 5,039,193 A | 8/1991 | Snow et al. |
| 5,058,587 A | 10/1991 | Kohno et al. |
| 5,118,405 A | 6/1992 | Kaneko et al. |
| 5,127,405 A | 7/1992 | Alcala et al. |
| 5,143,075 A | 9/1992 | Ishizuka |
| 5,151,603 A | 9/1992 | Nakamura |
| 5,152,277 A | 10/1992 | Honda et al. |
| 5,158,086 A | 10/1992 | Brown et al. |
| 5,212,671 A | 5/1993 | Fujii et al. |
| 5,219,335 A | 6/1993 | Willard et al. |
| 5,321,501 A | 6/1994 | Swanson et al. |
| 5,331,309 A | 7/1994 | Sakai |
| 5,383,467 A | 1/1995 | Auer et al. |
| 5,443,781 A | 8/1995 | Saab |
| 5,456,245 A | 10/1995 | Bornhop et al. |
| 5,459,570 A | 10/1995 | Swanson et al. |
| 5,554,139 A | 9/1996 | Okajima |
| 5,568,314 A | 10/1996 | Omori et al. |
| 5,568,503 A | 10/1996 | Omori |
| 5,644,427 A | 7/1997 | Omori et al. |
| 5,647,359 A | 7/1997 | Kohno et al. |
| 5,649,897 A | 7/1997 | Nakamura et al. |
| 5,689,316 A | 11/1997 | Hattori et al. |
| 5,738,100 A | 4/1998 | Yagami et al. |
| 5,745,163 A | 4/1998 | Nakamura et al. |
| 5,774,175 A | 6/1998 | Hattori |
| 5,774,261 A | 6/1998 | Omori et al. |
| 5,793,341 A | 8/1998 | Omori et al. |
| 5,818,399 A | 10/1998 | Omori et al. |
| 5,860,923 A | 1/1999 | Lenker et al. |
| 5,976,017 A | 11/1999 | Omori et al. |
| 5,999,591 A | 12/1999 | Kobayashi et al. |
| 6,011,580 A | 1/2000 | Hattori et al. |
| 6,011,809 A | 1/2000 | Tosaka |
| 6,019,507 A | 2/2000 | Takaki |
| 6,019,737 A | 2/2000 | Murata |
| 6,033,383 A | 3/2000 | Ginsburg |
| 6,036,682 A | 3/2000 | Lange et al. |
| 6,052,613 A | 4/2000 | Takaki |
| 6,064,684 A | 5/2000 | Yoon et al. |
| 6,069,698 A | 5/2000 | Ozawa et al. |
| 6,115,058 A | 9/2000 | Omori et al. |
| 6,134,003 A | 10/2000 | Tearney et al. |
| 6,160,826 A | 12/2000 | Swanson et al. |
| 6,165,127 A | 12/2000 | Crowley |
| 6,191,862 B1 | 2/2001 | Swanson et al. |
| 6,208,887 B1 | 3/2001 | Clarke |
| 6,217,828 B1 | 4/2001 | Bretscher et al. |
| 6,283,632 B1 | 9/2001 | Takaki |
| 6,296,608 B1 | 10/2001 | Daniels et al. |
| 6,309,358 B1 | 10/2001 | Okubo |
| 6,341,036 B1 | 1/2002 | Tearney et al. |
| 6,364,841 B1 | 4/2002 | White et al. |
| 6,383,209 B1 | 5/2002 | Crowley |
| 6,445,939 B1 | 9/2002 | Swanson et al. |
| 6,449,500 B1 | 9/2002 | Asai et al. |
| 6,471,656 B1 | 10/2002 | Shalman et al. |
| 6,485,413 B1 | 11/2002 | Boppart et al. |
| 6,485,482 B1 | 11/2002 | Belef |
| 6,520,959 B1 | 2/2003 | Iwahashi et al. |
| 6,530,921 B1 | 3/2003 | Maki |
| 6,547,757 B1 | 4/2003 | Kranz et al. |
| 6,549,687 B1 | 4/2003 | Kochergin et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,570,893 B1 | 5/2003 | Libatique et al. |
| 6,572,553 B2 | 6/2003 | Crowley |
| 6,577,391 B1 | 6/2003 | Faupel et al. |
| 6,579,286 B1 | 6/2003 | Maki et al. |
| 6,589,233 B1 | 7/2003 | Maki |
| 6,601,459 B1 | 8/2003 | Jenni |
| 6,607,526 B1 | 8/2003 | Maki |
| 6,615,072 B1 | 9/2003 | Izatt et al. |
| 6,654,630 B2 | 11/2003 | Zuluaga et al. |
| 6,658,278 B2 | 12/2003 | Gruhl |
| 6,879,851 B2 | 4/2005 | McNamara et al. |
| 6,891,984 B2 | 5/2005 | Petersen et al. |
| 6,904,197 B2 | 6/2005 | Bhagavatula et al. |
| 6,904,199 B2 | 6/2005 | Zuluaga |
| 6,925,320 B2 | 8/2005 | Gruhl |
| 6,940,885 B1 | 9/2005 | Cheng et al. |
| 7,003,184 B2 | 2/2006 | Ronnekleiv et al. |
| 7,022,118 B2 | 4/2006 | Ariura et al. |
| 7,029,436 B2 | 4/2006 | Iizuka et al. |
| 7,099,358 B1 | 8/2006 | Chong |
| 7,134,994 B2 | 11/2006 | Alpert et al. |
| 7,155,272 B2 | 12/2006 | Yamaguchi et al. |
| 7,231,243 B2 | 6/2007 | Tearney et al. |
| 7,241,286 B2 | 7/2007 | Atlas |
| 7,365,859 B2 | 4/2008 | Yun et al. |
| 7,366,376 B2 | 4/2008 | Shishkov et al. |
| 7,382,949 B2 | 6/2008 | Bouma et al. |
| 7,450,980 B2 | 11/2008 | Kawanishi |
| 7,551,293 B2 | 6/2009 | Yelin et al. |
| 7,567,349 B2 | 7/2009 | Tearney et al. |
| 7,625,366 B2 | 12/2009 | Atlas |
| 7,682,089 B2 | 3/2010 | Rohlen |
| 7,691,061 B2 | 4/2010 | Hirota |
| 7,711,413 B2 | 5/2010 | Feldman et al. |
| 7,724,786 B2 | 5/2010 | Bouma et al. |
| 7,733,497 B2 | 6/2010 | Yun et al. |
| 7,738,941 B2 | 6/2010 | Hirota |
| 7,740,408 B2 | 6/2010 | Irisawa |
| 7,742,173 B2 | 6/2010 | Yun et al. |
| 7,761,139 B2 | 7/2010 | Tearney et al. |
| 7,783,337 B2 | 8/2010 | Feldman et al. |
| 7,794,230 B2 | 9/2010 | Lakin et al. |
| 7,803,141 B2 | 9/2010 | Epstein et al. |
| 7,812,961 B2 | 10/2010 | Yamaguchi |
| 7,813,609 B2 | 10/2010 | Petersen et al. |
| 7,815,632 B2 | 10/2010 | Hayakawa et al. |

(56) References Cited

U.S. PATENT DOCUMENTS

| | | |
|---|---|---|
| 7,843,572 B2 | 11/2010 | Tearney et al. |
| 7,847,949 B2 | 12/2010 | Tearney et al. |
| 7,848,791 B2 | 12/2010 | Schmitt et al. |
| 7,872,759 B2 | 1/2011 | Tearney et al. |
| 7,905,838 B2 | 3/2011 | Hirota |
| 7,911,621 B2 | 3/2011 | Motaghiannezam et al. |
| 7,916,387 B2 | 3/2011 | Schmitt |
| 7,920,271 B2 | 4/2011 | Vakoc et al. |
| 7,926,562 B2 | 4/2011 | Poitzsch et al. |
| 7,935,060 B2 | 5/2011 | Schmitt et al. |
| 7,940,397 B2 | 5/2011 | Masuda |
| 7,969,578 B2 | 6/2011 | Yun et al. |
| 7,982,879 B2 | 7/2011 | Desjardins et al. |
| 8,018,598 B2 | 9/2011 | Cense et al. |
| 8,029,446 B2 | 10/2011 | Horiike et al. |
| 8,029,447 B2 | 10/2011 | Kanz et al. |
| 8,032,200 B2 | 10/2011 | Tearney et al. |
| 8,040,524 B2 | 10/2011 | Ozawa |
| 8,047,996 B2 | 11/2011 | Goodnow et al. |
| 8,049,900 B2 | 11/2011 | Kemp et al. |
| 8,052,605 B2 | 11/2011 | Muller et al. |
| 8,055,107 B2 | 11/2011 | Masuda |
| 8,081,316 B2 | 12/2011 | De Boer et al. |
| 8,094,319 B2 | 1/2012 | Onimura |
| 8,100,833 B2 | 1/2012 | Hirota |
| 8,108,032 B2 | 1/2012 | Onimura et al. |
| 8,116,605 B2 | 2/2012 | Petersen et al. |
| 8,125,648 B2 | 2/2012 | Milner et al. |
| 8,149,418 B2 | 4/2012 | Tearney et al. |
| 8,157,741 B2 | 4/2012 | Hirota |
| 8,157,742 B2 | 4/2012 | Taylor |
| 8,174,702 B2 | 5/2012 | Tearney et al. |
| 8,206,372 B2 | 6/2012 | Larson et al. |
| 8,206,377 B2 | 6/2012 | Petroff |
| 8,208,995 B2 | 6/2012 | Tearney et al. |
| 8,231,516 B2 | 7/2012 | Maschke |
| 8,241,196 B2 | 8/2012 | Scibona |
| 8,289,522 B2 | 10/2012 | Tearney et al. |
| RE43,875 E | 12/2012 | Shishkov et al. |
| 8,322,932 B2 | 12/2012 | Irisawa |
| 8,325,419 B2 | 12/2012 | Schmitt |
| 8,337,379 B2 | 12/2012 | Fletcher et al. |
| 8,339,592 B2 | 12/2012 | Hlavinka et al. |
| 8,346,348 B2 | 1/2013 | Onimura |
| 8,351,665 B2 | 1/2013 | Tearney et al. |
| 8,355,138 B2 | 1/2013 | Yun et al. |
| 8,384,907 B2 | 2/2013 | Tearney et al. |
| 8,384,909 B2 | 2/2013 | Yun et al. |
| 8,412,312 B2 | 4/2013 | Judell et al. |
| 8,414,496 B2 | 4/2013 | Goodnow et al. |
| 8,449,439 B2 | 5/2013 | Fletcher et al. |
| 8,449,468 B2 | 5/2013 | Petersen et al. |
| 8,452,371 B2 | 5/2013 | Feldman et al. |
| 8,473,037 B2 | 6/2013 | Irisawa |
| 8,473,073 B2 | 6/2013 | Vardiman |
| 8,478,384 B2 | 7/2013 | Schmitt et al. |
| 8,478,387 B2 | 7/2013 | Xu |
| 8,493,567 B2 | 7/2013 | Inoue |
| 8,501,015 B2 | 8/2013 | Fletcher et al. |
| 8,503,844 B2 | 8/2013 | Petersen et al. |
| 8,531,676 B2 | 9/2013 | Condit et al. |
| 8,535,210 B2 | 9/2013 | Kolenbrander et al. |
| 8,556,820 B2 | 10/2013 | Alpert et al. |
| 8,559,012 B2 | 10/2013 | Tearney et al. |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,585,592 B2 | 11/2013 | Luevano et al. |
| 8,593,619 B2 | 11/2013 | Colice et al. |
| 8,593,641 B2 | 11/2013 | Kemp et al. |
| 8,618,032 B2 | 12/2013 | Kurita |
| 8,626,453 B2 | 1/2014 | Myoujou et al. |
| 8,636,659 B2 | 1/2014 | Alpert et al. |
| 8,676,013 B2 | 3/2014 | Bouma et al. |
| 8,676,299 B2 | 3/2014 | Schmitt et al. |
| 8,687,201 B2 | 4/2014 | Adler |
| 8,705,046 B2 | 4/2014 | Yun et al. |
| 8,712,506 B2 | 4/2014 | Courtney et al. |
| 8,753,281 B2 | 6/2014 | Schmitt et al. |
| 8,760,663 B2 | 6/2014 | Tearney et al. |
| 8,761,469 B2 | 6/2014 | Kemp et al. |
| 8,786,336 B1 | 7/2014 | Schmitt |
| 8,804,126 B2 | 8/2014 | Tearney et al. |
| 8,810,901 B2 | 8/2014 | Huber et al. |
| 8,825,142 B2 | 9/2014 | Suehara |
| 8,827,926 B2 | 9/2014 | Kinoshita et al. |
| 8,831,321 B1 | 9/2014 | Elbasiony |
| 8,868,159 B2 | 10/2014 | Onimura |
| 8,885,171 B2 | 11/2014 | Watanabe et al. |
| 8,896,838 B2 | 11/2014 | Tearney et al. |
| 8,902,941 B2 | 12/2014 | Schmitt |
| 8,909,324 B2 | 12/2014 | Furuichi |
| 8,911,357 B2 | 12/2014 | Omori |
| 8,926,590 B2 | 1/2015 | Petroff |
| 8,928,889 B2 | 1/2015 | Tearney et al. |
| 8,945,526 B2 | 2/2015 | Akitsu et al. |
| 8,948,228 B2 | 2/2015 | Adler |
| 8,948,613 B2 | 2/2015 | Schmitt et al. |
| 8,953,911 B1 | 2/2015 | Xu et al. |
| 8,994,803 B2 | 3/2015 | Kaneko |
| 8,996,099 B2 | 3/2015 | Feldman et al. |
| 8,998,797 B2 | 4/2015 | Omori |
| 9,007,696 B2 | 4/2015 | Petersen et al. |
| 9,033,890 B2 | 5/2015 | Furuichi |
| 9,036,966 B2 | 5/2015 | Bhagavatula et al. |
| 9,039,626 B2 | 5/2015 | Courtney |
| 9,060,689 B2 | 6/2015 | Tearney et al. |
| 9,069,396 B2 | 6/2015 | Adler et al. |
| 9,081,148 B2 | 7/2015 | Tearney et al. |
| 9,084,532 B2 | 7/2015 | Horiike |
| 9,087,368 B2 | 7/2015 | Tearney et al. |
| 9,091,524 B2 | 7/2015 | Adler et al. |
| 9,101,298 B2 | 8/2015 | Hossack et al. |
| 9,107,682 B2 | 8/2015 | Scheller et al. |
| 9,107,687 B2 | 8/2015 | Kinoshita et al. |
| 9,121,926 B2 | 9/2015 | Nair et al. |
| 9,131,850 B2 | 9/2015 | Liu et al. |
| 9,138,147 B2 | 9/2015 | Schmitt et al. |
| 9,164,240 B2 | 10/2015 | Schmitt et al. |
| 9,168,003 B2 | 10/2015 | Suzuki et al. |
| 9,173,572 B2 | 11/2015 | Colice et al. |
| 9,173,591 B2 | 11/2015 | Elbasiony et al. |
| 9,194,690 B2 | 11/2015 | Bhagavatula et al. |
| 9,207,064 B2 | 12/2015 | Inoue |
| 9,226,660 B2 | 1/2016 | De Boer et al. |
| 9,226,665 B2 | 1/2016 | Tearney et al. |
| 9,254,102 B2 | 2/2016 | Tearney et al. |
| 9,289,127 B2 | 3/2016 | Mitsuhashi et al. |
| 9,289,582 B2 | 3/2016 | Suehara |
| 9,295,450 B2 | 3/2016 | Furuichi et al. |
| 9,295,455 B2 | 3/2016 | Karino et al. |
| 9,301,687 B2 | 4/2016 | Kemp |
| 9,304,121 B2 | 4/2016 | Tearney et al. |
| 9,322,639 B2 | 4/2016 | Watanabe et al. |
| 9,330,092 B2 | 5/2016 | Vakoc et al. |
| 9,339,173 B2 | 5/2016 | Mcweeney et al. |
| 9,339,348 B2 | 5/2016 | Davies et al. |
| 9,345,864 B2 | 5/2016 | Suehara |
| 9,347,765 B2 | 5/2016 | Kemp et al. |
| 9,351,698 B2 | 5/2016 | Dascal et al. |
| 9,357,923 B2 | 6/2016 | Courtney et al. |
| 9,375,148 B2 | 6/2016 | Senoo |
| 9,375,158 B2 | 6/2016 | Vakoc et al. |
| 9,375,164 B2 | 6/2016 | Tolkowsky et al. |
| 9,377,290 B2 | 6/2016 | Yun et al. |
| 9,404,731 B2 | 8/2016 | Adler et al. |
| 9,408,539 B2 | 8/2016 | Tearney et al. |
| 9,417,052 B2 | 8/2016 | Adler |
| 9,435,736 B2 | 9/2016 | Kolenbrander et al. |
| 9,435,956 B1 | 9/2016 | Xu et al. |
| 9,439,570 B2 | 9/2016 | Vertikov |
| 9,441,948 B2 | 9/2016 | Vakoc et al. |
| 9,462,950 B2 | 10/2016 | Xu |

(56) References Cited

U.S. PATENT DOCUMENTS

| | | |
|---|---|---|
| 9,464,883 B2 | 10/2016 | Swanson et al. |
| 9,488,464 B1 | 11/2016 | Schmitt |
| 9,507,074 B2 | 11/2016 | Zhu et al. |
| 9,513,276 B2 | 12/2016 | Tearney et al. |
| 9,526,424 B2 | 12/2016 | Judell et al. |
| 9,566,752 B2 | 2/2017 | Hartkorn |
| 9,572,495 B2 | 2/2017 | Schmitt et al. |
| 9,572,496 B2 | 2/2017 | Furuichi et al. |
| 9,605,942 B2 | 3/2017 | Staloff |
| 9,610,064 B2 | 4/2017 | Adler et al. |
| 9,615,771 B2 | 4/2017 | Furuichi et al. |
| 9,622,706 B2 | 4/2017 | Dick et al. |
| 9,638,862 B2 | 5/2017 | Bhagavatula et al. |
| 9,642,531 B2 | 5/2017 | Tearney et al. |
| 9,645,322 B2 | 5/2017 | Murashima et al. |
| 9,646,377 B2 | 5/2017 | Tearney et al. |
| 9,659,375 B2 | 5/2017 | Zagrodsky et al. |
| 9,702,687 B2 | 7/2017 | Schmitt |
| 9,702,762 B2 | 7/2017 | Friedman et al. |
| 9,704,240 B2 | 7/2017 | Lam et al. |
| 9,710,891 B2 | 7/2017 | Sakamoto |
| 9,730,613 B2 | 8/2017 | Stigall et al. |
| 9,763,623 B2 | 9/2017 | Tearney et al. |
| 9,778,020 B2 | 10/2017 | Tumlinson et al. |
| 9,788,790 B2 | 10/2017 | Black et al. |
| 9,808,303 B2 | 11/2017 | Ryba et al. |
| 9,812,846 B2 | 11/2017 | Yun et al. |
| 9,833,221 B2 | 12/2017 | Hutchins et al. |
| 9,836,835 B2 | 12/2017 | Furuichi et al. |
| 9,843,159 B2 | 12/2017 | Cable et al. |
| 9,855,020 B2 | 1/2018 | Nair et al. |
| 9,858,387 B2 | 1/2018 | Lavi et al. |
| 9,864,140 B2 | 1/2018 | Adler et al. |
| 9,872,665 B2 | 1/2018 | Okubo et al. |
| 9,891,044 B2 | 2/2018 | Tu et al. |
| 9,897,538 B2 | 2/2018 | Fearney et al. |
| 9,907,527 B2 | 3/2018 | Dascal et al. |
| 9,933,244 B2 | 4/2018 | Krol et al. |
| 9,940,723 B2 | 4/2018 | Gopinath et al. |
| 9,943,233 B2 | 4/2018 | Lavi et al. |
| 9,962,127 B2 | 5/2018 | Wang et al. |
| 9,980,648 B2 | 5/2018 | Itoh et al. |
| 9,983,356 B2 | 5/2018 | Schmitt et al. |
| 9,986,938 B2 | 6/2018 | Tu et al. |
| 9,989,945 B2 | 6/2018 | Adler et al. |
| 9,996,921 B2 | 6/2018 | Ambwani et al. |
| 10,004,400 B2 | 6/2018 | Nakamoto et al. |
| 10,006,753 B2 | 6/2018 | Schmitt et al. |
| 10,028,725 B2 | 7/2018 | Petroff |
| 10,089,755 B2 | 10/2018 | Griffin et al. |
| 10,092,188 B2 | 10/2018 | Jaffer et al. |
| 10,109,058 B2 | 10/2018 | Ambwani et al. |
| 10,124,153 B2 | 11/2018 | Feig et al. |
| 10,140,712 B2 | 11/2018 | Ambwani |
| 10,162,114 B2 | 12/2018 | Bhagavatula et al. |
| 10,172,582 B2 | 1/2019 | Dascal et al. |
| 10,186,056 B2 | 1/2019 | Senzig et al. |
| 10,207,124 B2 | 2/2019 | Shimizu et al. |
| 10,213,109 B2 | 2/2019 | Itoh et al. |
| 10,213,186 B2 | 2/2019 | Inoue et al. |
| 10,219,780 B2 | 3/2019 | Castella et al. |
| 10,222,956 B2 | 3/2019 | Gopinath et al. |
| 10,238,349 B2 | 3/2019 | Furuichi et al. |
| 10,261,223 B2 | 4/2019 | Tearney et al. |
| 10,271,818 B2 | 4/2019 | Kobayashi |
| 10,285,568 B2 * | 5/2019 | Tearney ............ A61B 1/00082 |
| 10,327,726 B2 | 6/2019 | Dascal et al. |
| 10,331,099 B2 | 6/2019 | Adler et al. |
| 10,335,039 B2 | 7/2019 | Xu |
| 10,338,795 B2 | 7/2019 | Gopinath et al. |
| 10,342,502 B2 | 7/2019 | Dascal et al. |
| 10,387,013 B2 | 8/2019 | Jamello |
| 10,453,190 B2 | 10/2019 | Griffin |
| 10,453,196 B2 | 10/2019 | Ambwani |
| 10,463,254 B2 | 11/2019 | Tearney et al. |
| 10,499,813 B2 | 12/2019 | Adler |
| 10,529,093 B2 | 1/2020 | Griffin et al. |
| 10,551,251 B2 | 2/2020 | Friedman et al. |
| 10,593,037 B2 | 3/2020 | Gopinath |
| 10,631,754 B2 | 4/2020 | Gopinath |
| 10,646,198 B2 | 5/2020 | Peterson et al. |
| 10,648,918 B2 | 5/2020 | Schmitt |
| 10,687,777 B2 | 6/2020 | Dascal et al. |
| 10,713,786 B2 | 7/2020 | Ambwani et al. |
| 10,729,376 B2 * | 8/2020 | Courtney ............ A61M 25/0113 |
| 10,792,012 B2 | 10/2020 | Hutchins et al. |
| 10,878,572 B2 | 12/2020 | Gopinath et al. |
| 10,902,599 B2 | 1/2021 | Ambwani et al. |
| 2002/0041724 A1 | 4/2002 | Ronnekleiv et al. |
| 2002/0072880 A1 | 6/2002 | Svanerudh et al. |
| 2002/0099289 A1 | 7/2002 | Crowley |
| 2002/0131049 A1 | 9/2002 | Schmitt |
| 2002/0151823 A1 * | 10/2002 | Miyata ................ A61M 25/09 600/585 |
| 2002/0163622 A1 | 11/2002 | Magnin et al. |
| 2002/0183601 A1 | 12/2002 | Tearney et al. |
| 2002/0183622 A1 | 12/2002 | Zuluaga et al. |
| 2002/0188204 A1 | 12/2002 | McNamara et al. |
| 2002/0198457 A1 | 12/2002 | Tearney et al. |
| 2003/0004417 A1 | 1/2003 | Ariura et al. |
| 2003/0013952 A1 | 1/2003 | Iizuka et al. |
| 2003/0073909 A1 | 4/2003 | Gruhl |
| 2003/0081875 A1 | 5/2003 | Kochergin et al. |
| 2003/0165291 A1 | 9/2003 | Bhagavatula et al. |
| 2003/0216621 A1 | 11/2003 | Alpert et al. |
| 2004/0017961 A1 | 1/2004 | Petersen et al. |
| 2004/0034290 A1 | 2/2004 | Zuluaga |
| 2004/0082861 A1 | 4/2004 | Gruhl |
| 2004/0092913 A1 | 5/2004 | Hennings et al. |
| 2004/0215166 A1 | 10/2004 | Atlas |
| 2005/0004453 A1 | 1/2005 | Tearney et al. |
| 2005/0038406 A1 | 2/2005 | Epstein et al. |
| 2005/0101870 A1 | 5/2005 | Yamaguchi et al. |
| 2005/0128488 A1 | 6/2005 | Yelin et al. |
| 2005/0187422 A1 | 8/2005 | Maschke |
| 2005/0201662 A1 | 9/2005 | Petersen et al. |
| 2005/0221277 A1 | 10/2005 | Kawanishi |
| 2005/0272975 A1 * | 12/2005 | McWeeney ....... A61M 25/0068 600/113 |
| 2005/0288583 A1 | 12/2005 | Hirota |
| 2006/0039004 A1 | 2/2006 | de Boer et al. |
| 2006/0055936 A1 | 3/2006 | Yun et al. |
| 2006/0058622 A1 | 3/2006 | Tearney et al. |
| 2006/0067620 A1 | 3/2006 | Shishkov et al. |
| 2006/0091566 A1 | 5/2006 | Yang et al. |
| 2006/0093276 A1 | 5/2006 | Bouma et al. |
| 2006/0095065 A1 | 5/2006 | Tanimura et al. |
| 2006/0166176 A1 | 7/2006 | Lakin et al. |
| 2006/0227333 A1 | 10/2006 | Tearney et al. |
| 2006/0241484 A1 | 10/2006 | Horiike et al. |
| 2006/0241493 A1 | 10/2006 | Feldman et al. |
| 2006/0241503 A1 | 10/2006 | Schmitt et al. |
| 2006/0244973 A1 | 11/2006 | Yun et al. |
| 2006/0247743 A1 | 11/2006 | Hayakawa et al. |
| 2006/0279742 A1 | 12/2006 | Tearney et al. |
| 2007/0012886 A1 | 1/2007 | Tearney et al. |
| 2007/0015969 A1 | 1/2007 | Feldman et al. |
| 2007/0035743 A1 | 2/2007 | Vakoc et al. |
| 2007/0038040 A1 | 2/2007 | Cense et al. |
| 2007/0038274 A1 | 2/2007 | Ishii et al. |
| 2007/0060822 A1 | 3/2007 | Alpert et al. |
| 2007/0073162 A1 | 3/2007 | Tearney et al. |
| 2007/0081236 A1 | 4/2007 | Tearney et al. |
| 2007/0106155 A1 | 5/2007 | Goodnow et al. |
| 2007/0121196 A1 | 5/2007 | Tearney et al. |
| 2007/0201033 A1 | 8/2007 | Desjardins et al. |
| 2007/0229801 A1 | 10/2007 | Tearney et al. |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0233396 A1 | 10/2007 | Tearney et al. |
| 2007/0236700 A1 | 10/2007 | Yun et al. |
| 2007/0244391 A1 | 10/2007 | Hirota |

(56) References Cited

U.S. PATENT DOCUMENTS

| | | |
|---|---|---|
| 2007/0260198 A1 | 11/2007 | Atlas |
| 2008/0002211 A1 | 1/2008 | Park et al. |
| 2008/0004530 A1 | 1/2008 | Feldman et al. |
| 2008/0007734 A1 | 1/2008 | Park et al. |
| 2008/0019908 A1 | 1/2008 | Akitsu et al. |
| 2008/0021275 A1 | 1/2008 | Tearney et al. |
| 2008/0045394 A1 | 2/2008 | Fletcher et al. |
| 2008/0049232 A1 | 2/2008 | Vakoc et al. |
| 2008/0161696 A1 | 7/2008 | Schmitt et al. |
| 2008/0165366 A1 | 7/2008 | Schmitt |
| 2008/0177139 A1 | 7/2008 | Courtney et al. |
| 2008/0181263 A1 | 7/2008 | Bouma et al. |
| 2008/0208227 A1 | 8/2008 | Kadykowski et al. |
| 2008/0225301 A1 | 9/2008 | Yamaguchi |
| 2008/0262346 A1 | 10/2008 | Assis et al. |
| 2008/0269572 A1 | 10/2008 | Kanz et al. |
| 2008/0291463 A1 | 11/2008 | Milner et al. |
| 2008/0297806 A1 | 12/2008 | Motaghiannezam et al. |
| 2009/0018393 A1 | 1/2009 | Dick et al. |
| 2009/0027689 A1 | 1/2009 | Yun et al. |
| 2009/0036782 A1 | 2/2009 | Vakoc et al. |
| 2009/0043191 A1 | 2/2009 | Castella et al. |
| 2009/0046295 A1 | 2/2009 | Kemp et al. |
| 2009/0046980 A1 | 2/2009 | Rohlen |
| 2009/0073454 A1 | 3/2009 | Ozawa |
| 2009/0073455 A1 | 3/2009 | Onimura |
| 2009/0093980 A1 | 4/2009 | Kemp et al. |
| 2009/0122320 A1 | 5/2009 | Petersen et al. |
| 2009/0131801 A1* | 5/2009 | Suter ............ A61B 5/6853 600/478 |
| 2009/0135429 A1 | 5/2009 | Masuda |
| 2009/0143686 A1 | 6/2009 | Onimura et al. |
| 2009/0182246 A1 | 7/2009 | Kinoshita et al. |
| 2009/0192519 A1 | 7/2009 | Omori |
| 2009/0196477 A1 | 8/2009 | Cense et al. |
| 2009/0196554 A1 | 8/2009 | Irisawa |
| 2009/0251704 A1 | 10/2009 | Masuda |
| 2009/0261240 A1 | 10/2009 | Watanabe et al. |
| 2009/0262361 A1 | 10/2009 | Tanioka et al. |
| 2009/0283258 A1 | 11/2009 | Poitzsch et al. |
| 2009/0299195 A1 | 12/2009 | Muller et al. |
| 2009/0306520 A1 | 12/2009 | Schmitt et al. |
| 2010/0019189 A1 | 1/2010 | Kurita |
| 2010/0042084 A1 | 2/2010 | Nariyuki et al. |
| 2010/0073682 A1 | 3/2010 | Inoue |
| 2010/0076320 A1 | 3/2010 | Petersen et al. |
| 2010/0094127 A1 | 4/2010 | Xu |
| 2010/0110414 A1 | 5/2010 | Colice et al. |
| 2010/0130872 A1 | 5/2010 | Irisawa |
| 2010/0157309 A1 | 6/2010 | Tearney et al. |
| 2010/0158339 A1 | 6/2010 | Omori |
| 2010/0160134 A1 | 6/2010 | Scibona |
| 2010/0160780 A1 | 6/2010 | Swan et al. |
| 2010/0168587 A1 | 7/2010 | Feldman et al. |
| 2010/0220334 A1 | 9/2010 | Condit et al. |
| 2010/0241154 A1 | 9/2010 | Larson et al. |
| 2010/0249601 A1 | 9/2010 | Courtney |
| 2010/0253949 A1 | 10/2010 | Adler et al. |
| 2010/0298908 A1 | 11/2010 | Vardiman |
| 2010/0305452 A1 | 12/2010 | Black et al. |
| 2010/0309477 A1 | 12/2010 | Yun et al. |
| 2011/0007315 A1 | 1/2011 | Petersen et al. |
| 2011/0009741 A1 | 1/2011 | Matthews et al. |
| 2011/0019182 A1 | 1/2011 | Hlavinka et al. |
| 2011/0058178 A1 | 3/2011 | Tearney et al. |
| 2011/0071404 A1 | 3/2011 | Schmitt et al. |
| 2011/0071405 A1 | 3/2011 | Judell et al. |
| 2011/0092823 A1 | 4/2011 | Tearney et al. |
| 2011/0101207 A1 | 5/2011 | Schmitt |
| 2011/0143905 A1 | 6/2011 | Kolenbrander et al. |
| 2011/0144504 A1 | 6/2011 | Tearney et al. |
| 2011/0149296 A1 | 6/2011 | Tearney et al. |
| 2011/0151980 A1 | 6/2011 | Petroff |
| 2011/0157686 A1 | 6/2011 | Huber et al. |
| 2011/0172511 A1 | 7/2011 | Petersen et al. |
| 2011/0178398 A1 | 7/2011 | Tearney et al. |
| 2011/0178413 A1 | 7/2011 | Schmitt et al. |
| 2011/0196217 A1 | 8/2011 | Myoujou et al. |
| 2011/0201924 A1 | 8/2011 | Tearney et al. |
| 2011/0216325 A1 | 9/2011 | Schmitt |
| 2011/0218403 A1 | 9/2011 | Tearney et al. |
| 2011/0224541 A1 | 9/2011 | Yun et al. |
| 2011/0228280 A1 | 9/2011 | Schmitt et al. |
| 2011/0237958 A1 | 9/2011 | Onimura |
| 2011/0245683 A1 | 10/2011 | Onimura |
| 2011/0245684 A1 | 10/2011 | Onimura |
| 2011/0261366 A1 | 10/2011 | Tearney et al. |
| 2011/0267340 A1 | 11/2011 | Kraus et al. |
| 2011/0270091 A1 | 11/2011 | Hossack et al. |
| 2011/0292400 A1 | 12/2011 | Fleming et al. |
| 2011/0299091 A1 | 12/2011 | Yun et al. |
| 2012/0002928 A1 | 1/2012 | Irisawa |
| 2012/0007974 A1 | 1/2012 | Kaneko |
| 2012/0008146 A1 | 1/2012 | Fearney et al. |
| 2012/0013914 A1 | 1/2012 | Kemp et al. |
| 2012/0035454 A1 | 2/2012 | Tearney et al. |
| 2012/0053918 A1 | 3/2012 | Taylor |
| 2012/0057157 A1 | 3/2012 | Petersen et al. |
| 2012/0063570 A1 | 3/2012 | Furuichi et al. |
| 2012/0065517 A1 | 3/2012 | Goodnow et al. |
| 2012/0071736 A1 | 3/2012 | Luevano et al. |
| 2012/0127476 A1 | 5/2012 | De Boer et al. |
| 2012/0135384 A1 | 5/2012 | Nakao |
| 2012/0170848 A1 | 7/2012 | Kemp et al. |
| 2012/0190974 A1 | 7/2012 | Suehara |
| 2012/0215091 A1 | 8/2012 | Suzuki et al. |
| 2012/0220836 A1 | 8/2012 | Alpert et al. |
| 2012/0226151 A1 | 9/2012 | Irisawa |
| 2012/0236883 A1 | 9/2012 | Adler |
| 2012/0238869 A1 | 9/2012 | Schmitt et al. |
| 2012/0243761 A1 | 9/2012 | Senzig et al. |
| 2012/0245459 A1 | 9/2012 | Senoo |
| 2012/0250028 A1 | 10/2012 | Schmitt et al. |
| 2012/0253114 A1 | 10/2012 | Kinoshita et al. |
| 2012/0253123 A1 | 10/2012 | Shimizu et al. |
| 2012/0253184 A1 | 10/2012 | Furuichi et al. |
| 2012/0253185 A1 | 10/2012 | Furuichi |
| 2012/0281237 A1 | 11/2012 | Tearney et al. |
| 2012/0310081 A1 | 12/2012 | Adler et al. |
| 2012/0330101 A1 | 12/2012 | Brennan et al. |
| 2013/0002843 A1 | 1/2013 | Horiike |
| 2013/0023760 A1 | 1/2013 | Liu et al. |
| 2013/0023761 A1 | 1/2013 | Petroff |
| 2013/0051728 A1 | 2/2013 | Petroff et al. |
| 2013/0100455 A1 | 4/2013 | Tearney et al. |
| 2013/0116671 A1 | 5/2013 | Scheller et al. |
| 2013/0128274 A1 | 5/2013 | Yun et al. |
| 2013/0148106 A1 | 6/2013 | Tearney et al. |
| 2013/0176571 A1 | 7/2013 | Tearney et al. |
| 2013/0185023 A1 | 7/2013 | Vakoc et al. |
| 2013/0188850 A1 | 7/2013 | Tearney et al. |
| 2013/0314716 A1 | 11/2013 | Tearney et al. |
| 2013/0331689 A1 | 12/2013 | Le et al. |
| 2014/0031677 A1 | 1/2014 | Iftimia et al. |
| 2014/0031679 A1* | 1/2014 | Tashiro ............ A61B 5/0077 600/425 |
| 2014/0083970 A1 | 3/2014 | Kumar et al. |
| 2014/0114182 A1 | 4/2014 | Petersen et al. |
| 2014/0142432 A1 | 5/2014 | Hutchins et al. |
| 2014/0142436 A1 | 5/2014 | Hutchins et al. |
| 2014/0150782 A1* | 6/2014 | Vazales ............ A61M 16/0434 128/202.16 |
| 2014/0177935 A1 | 6/2014 | Nair et al. |
| 2014/0180071 A1 | 6/2014 | Stigall et al. |
| 2014/0187929 A1 | 7/2014 | Schmitt et al. |
| 2014/0218742 A1 | 8/2014 | Adler |
| 2014/0247454 A1 | 9/2014 | Bhagavatula et al. |
| 2014/0249407 A1 | 9/2014 | Adler et al. |
| 2014/0257087 A1 | 9/2014 | Elbasiony et al. |
| 2014/0267038 A1 | 9/2014 | Adler et al. |
| 2014/0268167 A1 | 9/2014 | Friedman et al. |
| 2014/0276108 A1 | 9/2014 | Vertikov |
| 2014/0301620 A1 | 10/2014 | Tearney et al. |
| 2014/0323877 A1 | 10/2014 | Courtney et al. |

(56) References Cited

U.S. PATENT DOCUMENTS

| | | |
|---|---|---|
| 2014/0379269 A1 | 12/2014 | Schmitt |
| 2015/0025369 A1 | 1/2015 | Bhagavatula et al. |
| 2015/0029513 A1 | 1/2015 | Tearney et al. |
| 2015/0049339 A1 | 2/2015 | Tearney et al. |
| 2015/0077755 A1 | 3/2015 | Yun et al. |
| 2015/0099968 A1 | 4/2015 | Jamello |
| 2015/0099975 A1 | 4/2015 | Lam et al. |
| 2015/0119707 A1 | 4/2015 | Petroff |
| 2015/0133773 A1 | 5/2015 | Jaffer et al. |
| 2015/0133776 A1 | 5/2015 | Hoffman |
| 2015/0153157 A1 | 6/2015 | Schmitt et al. |
| 2015/0192405 A1 | 7/2015 | Schmitt |
| 2015/0216415 A1 | 8/2015 | Uribe-Patarroyo et al. |
| 2015/0238084 A1 | 8/2015 | Tearney et al. |
| 2015/0245768 A1* | 9/2015 | Hasegawa ............ G01B 9/0205 356/479 |
| 2015/0265152 A1 | 9/2015 | Feldman et al. |
| 2015/0265162 A1 | 9/2015 | Lavi et al. |
| 2015/0306361 A1 | 10/2015 | Feig et al. |
| 2015/0366534 A1 | 12/2015 | Nair et al. |
| 2015/0370229 A1 | 12/2015 | Adler et al. |
| 2016/0000406 A1 | 1/2016 | Petroff |
| 2016/0015337 A1 | 1/2016 | Inoue et al. |
| 2016/0022208 A1 | 1/2016 | Gopinath |
| 2016/0070066 A1 | 3/2016 | Schmitt et al. |
| 2016/0124134 A1 | 5/2016 | Zhu et al. |
| 2016/0171711 A1 | 6/2016 | Gopinath et al. |
| 2016/0174925 A1 | 6/2016 | Dascal et al. |
| 2016/0228071 A1 | 8/2016 | Wang et al. |
| 2016/0270766 A1 | 9/2016 | Kobayashi |
| 2016/0313507 A1 | 10/2016 | Adler et al. |
| 2016/0320170 A1 | 11/2016 | Yun et al. |
| 2016/0335763 A1 | 11/2016 | Ambwani et al. |
| 2016/0335766 A1 | 11/2016 | Ambwani et al. |
| 2016/0338753 A1 | 11/2016 | Ryba et al. |
| 2016/0349417 A1 | 12/2016 | Tearney et al. |
| 2017/0014100 A1 | 1/2017 | Mori |
| 2017/0020392 A1 | 1/2017 | Xu |
| 2017/0024532 A1 | 1/2017 | Gopinath et al. |
| 2017/0024910 A1 | 1/2017 | Griffin et al. |
| 2017/0103520 A1 | 4/2017 | Gopinath et al. |
| 2017/0135663 A1 | 5/2017 | Dascal et al. |
| 2017/0140243 A1 | 5/2017 | Ambwani |
| 2017/0140531 A1 | 5/2017 | Dascal et al. |
| 2017/0140532 A1 | 5/2017 | Dascal et al. |
| 2017/0140560 A1 | 5/2017 | Kraus et al. |
| 2017/0143296 A1 | 5/2017 | Peterson et al. |
| 2017/0148161 A1 | 5/2017 | Griffin |
| 2017/0153439 A1 | 6/2017 | Horiike |
| 2017/0188831 A1 | 7/2017 | Adler et al. |
| 2017/0238809 A1 | 8/2017 | Fearney et al. |
| 2017/0261378 A1 | 9/2017 | Friedman et al. |
| 2017/0301084 A1 | 10/2017 | Gopinath |
| 2017/0325712 A1 | 11/2017 | Gopinath |
| 2017/0367581 A1 | 12/2017 | Fearney et al. |
| 2018/0003482 A1 | 1/2018 | Schmitt |
| 2018/0085095 A1 | 3/2018 | Hutchins et al. |
| 2018/0085170 A1 | 3/2018 | Gopinath |
| 2018/0125372 A1 | 5/2018 | Petroff et al. |
| 2018/0192957 A1 | 7/2018 | Schmitt et al. |
| 2018/0192983 A1 | 7/2018 | Dascal et al. |
| 2018/0225830 A1 | 8/2018 | Gopinath et al. |
| 2018/0226773 A1 | 8/2018 | Yun et al. |
| 2018/0275622 A1 | 9/2018 | Adler et al. |
| 2018/0293730 A1 | 10/2018 | Ambwani et al. |
| 2018/0306569 A1 | 10/2018 | Schmitt et al. |
| 2018/0344173 A1 | 12/2018 | Tu et al. |
| 2018/0344174 A9 | 12/2018 | Schmitt et al. |
| 2018/0353241 A1 | 12/2018 | Tu et al. |
| 2019/0035114 A1 | 1/2019 | Griffin et al. |
| 2019/0096063 A1 | 3/2019 | Ambwani |
| 2019/0099237 A1 | 4/2019 | Booker et al. |
| 2019/0220980 A1 | 7/2019 | Ambwani et al. |
| 2019/0307412 A1 | 10/2019 | Dascal et al. |
| 2019/0365480 A1 | 12/2019 | Gopinath et al. |
| 2019/0380594 A1 | 12/2019 | Schmitt et al. |
| 2020/0142575 A1 | 5/2020 | Gopinath et al. |
| 2020/0167923 A1 | 5/2020 | Gopinath |
| 2020/0355557 A1 | 11/2020 | Friedman et al. |
| 2020/0397405 A1 | 12/2020 | Hutchins et al. |
| 2021/0004955 A1 | 1/2021 | Ambwani et al. |

FOREIGN PATENT DOCUMENTS

| | | |
|---|---|---|
| CN | 1780584 | 5/2006 |
| CN | 203801215 | 9/2014 |
| CN | 203801216 | 9/2014 |
| CN | 203805643 | 9/2014 |
| CN | 203805646 | 9/2014 |
| CN | 105019592 | 11/2015 |
| CN | 204826364 | 12/2015 |
| CN | 105662387 | 6/2016 |
| CN | 106570313 | 4/2017 |
| CN | 106650029 | 5/2017 |
| CN | 106805989 | 6/2017 |
| CN | 106974622 | 7/2017 |
| CN | 107115108 | 9/2017 |
| CN | 107133959 | 9/2017 |
| CN | 107233106 | 10/2017 |
| CN | 107745346 | 3/2018 |
| CN | 107978371 | 5/2018 |
| CN | 108022650 | 5/2018 |
| CN | 108038848 | 5/2018 |
| CN | 207464715 | 6/2018 |
| DE | 69738291 | 9/2008 |
| DE | 112016005442 | 8/2018 |
| DE | 112016005603 | 10/2018 |
| EP | 0883793 | 12/1998 |
| EP | 1685366 | 8/2006 |
| EP | 2505129 | 10/2012 |
| GB | 2512077 | 9/2014 |
| JP | 2005230552 | 9/2005 |
| JP | 2005533610 | 11/2005 |
| JP | 2006271869 | 10/2006 |
| JP | 2007268131 | 10/2007 |
| JP | 2008510586 | 4/2008 |
| JP | 2009072291 | 4/2009 |
| JP | 4494203 | 6/2010 |
| JP | 2010167029 | 8/2010 |
| JP | 2011078550 | 4/2011 |
| JP | 5093787 | 12/2012 |
| JP | 5269809 | 8/2013 |
| JP | 5474190 | 4/2014 |
| JP | 2014180575 | 9/2014 |
| JP | 5622796 | 11/2014 |
| JP | 5635149 | 12/2014 |
| JP | 5643315 | 12/2014 |
| JP | 2015013217 | 1/2015 |
| JP | 5689728 | 3/2015 |
| JP | 5721721 | 5/2015 |
| JP | 2015518393 | 7/2015 |
| JP | 5778579 | 9/2015 |
| JP | 2015164660 | 9/2015 |
| JP | 5814860 | 11/2015 |
| JP | 2015532717 | 11/2015 |
| JP | 5856605 | 2/2016 |
| JP | 2016508750 | 3/2016 |
| JP | 5987025 | 9/2016 |
| JP | 5997232 | 9/2016 |
| JP | 2018507400 | 3/2018 |
| JP | 2018527961 | 9/2018 |
| WO | 2004010856 | 2/2004 |
| WO | 2005047813 | 5/2005 |
| WO | 2006024015 | 3/2006 |
| WO | 2008134449 | 11/2008 |
| WO | 2009009799 | 1/2009 |
| WO | 2009009802 | 1/2009 |
| WO | 2010095370 | 8/2010 |
| WO | 2010113374 | 10/2010 |
| WO | 2012002302 | 1/2012 |
| WO | 2014142789 | 9/2014 |
| WO | 2014142815 | 9/2014 |
| WO | 2014163601 | 10/2014 |
| WO | 2014175853 | 10/2014 |

(56) References Cited

FOREIGN PATENT DOCUMENTS

| | | | | |
|---|---|---|---|---|
| WO | WO-2014163601 A1 * | 10/2014 | ............ | A61B 8/12 |
| WO | 2015044978 | 4/2015 | | |
| WO | 2015044982 | 4/2015 | | |
| WO | 2015044983 | 4/2015 | | |
| WO | 2015044984 | 4/2015 | | |
| WO | 2015074018 | 5/2015 | | |
| WO | 2015136853 | 9/2015 | | |
| WO | 2015141136 | 9/2015 | | |
| WO | 2016168605 | 10/2016 | | |
| WO | 2016187218 | 11/2016 | | |
| WO | 2016187231 | 11/2016 | | |
| WO | 2016210132 | 12/2016 | | |
| WO | 2017019626 | 2/2017 | | |
| WO | 2017019634 | 2/2017 | | |
| WO | 2015044987 | 3/2017 | | |
| WO | 2015045368 | 3/2017 | | |
| WO | 2017040484 | 3/2017 | | |
| WO | 2017097074 | 6/2017 | | |
| WO | 2017189942 | 11/2017 | | |
| WO | 2017200381 | 11/2017 | | |
| WO | 2019108598 | 6/2019 | | |

OTHER PUBLICATIONS

Introduction to silicone fluids (https://www.clearcoproducts.com/introduction-to-silicone-fluids.html, retrieved Sep. 24, 2020).*
Madigan, Jeremy. "Vascular access: guide catheter selection, usage, and compatibility." In Interventional Neuroradiology, pp. 27-38. Springer, London, 2014.*
Ghannam, Mamdouh T., and M. Nabil Esmail. "Rheological properties of poly (dimethylsiloxane)." Industrial & engineering chemistry research 37, No. 4 (1998): 1335-1340.*
Japanese Office Action dated Sep. 15, 2020 issued in corresponding Japanese Application No. 2018-510969, with English language summary.
International Search Report and Written Opinion dated Sep. 14, 2020 issued in corresponding International Application No. PCT/US20/30616.
Chinese Office Action dated May 25, 2020 issued in corresponding Chinese Application No. 201680034490.4, with English summary.
International Search Report and Written Opinion dated Jan. 31, 2020 issued in corresponding International Application No. PCT/US2019/051447.
FOCABEX, "Core Structure of Optical Cables" Article (online). Feb. 1, 2002 (retrieved Jan. 8, 2020). Retrieved from the Internet: URL: http://www.focabex.com/library-n/CORE-STRUCTURE-OF-OPTICAL-FIBER-CABLES.pdf.
Thorlabs, "Single Wavelength Graded-Index (GRIN) Lenses" Product Catalogue (online). Apr. 9, 2016 (retrieved Jan. 8, 2020). Retrieved from the Internet: URL: https://www.thorlabs.com/NewGroupPage9.cfm?ObjectGroup_ID=1209.
Extended European Search Report dated Apr. 9, 2019 issued in corresponding European Application No. 16842796.1.
Chinese Office Action dated Feb. 27, 2019 issued in corresponding Chinese Application No. 201680034490.4, with English summary.
Chinese Office Action dated Aug. 28, 2019 issued in corresponding Chinese Application No. 201680034490.4, with English summary.
European Office Action dated Feb. 4, 2020 issued in corresponding European Application No. 16780839.3.
Japanese Office Action dated Mar. 31, 2020 issued in corresponding Japanese Application No. 2018-505582, with English translation.
International Search Report dated Jul. 14, 2016 issued in corresponding International Application No. PCT/US2016/027764.
Chinese Office Action dated Aug. 28, 2019 issued in corresponding Chinese Application No. 201680034490.4, with English translation. (Re-submit with full translation provided by assoc).
International Search Report & Written Opinion dated Feb. 11, 2019, issued in related International Application No. PCT/US2018/062766.
Extended European Search Report dated Jan. 2, 2019 issued in corresponding European Application No. 16780839.3.
Jieheng Xi, et al. "Diffractive catheter for ultrahigh-resolution spectral-domain volumetric OCT imaging", Optics Letters, vol. 39, No. 7, Optical Society of America, Mar. 26, 2014, pp. 2016-2019.
International Search Report dated Nov. 7, 2016, issued in corresponding International Application No. PCT/US2016/049415.
Chinese Office Action dated Feb. 27, 2019 issued in corresponding Chinese Application No. 201680034490.4, with English translation.
*Previously submitted with references and brief OA summary on Mar. 20, 2019.
Athanasiou, L.S. et al. "Fully automated lumen segmentation of intracoronary optical coherence tomography images", Medical Imaging 2017, vol. 10133, pp. 1013321-1-1013321-7. Downloaded from the internet on Mar. 6, 2017: http://proceedings.spiedigitallibrary.org/.
Berger, J.D. et al. "Widely tunable external cavity diode laser based on a MEMS electrostatic rotary actuator", OSA/OFC 2001, pp. TuJ2-1-TuJ2-3.
BlazePhotonics. "NL-2.4-800 Highly nonlinear PCF" technical specification sheet.
Buus, J. et al. "Tunable Lasers in Optical Networks", Journal of Lightwave Technology, vol. 24, No. 1 (Jan. 2006), pp. 5-11.
Chang-Hasnain, C.J. "Tunable VCSEL", IEEE Journal on Selected Topics in Quantum Electronics, vol. 6, No. 6 (Nov./Dec. 2000), pp. 978-987.
Chang-Hasnain, C.J., "Progress and Prospects of Long-Wavelength VCSELs", IEEE Optical Communications (Feb. 2003), pp. S30-S34.
Chinn, S.R. et al. "Optical coherence tomography using a frequency-tunable optical source", Optics Letters, vol. 22, No. 5 (Mar. 1, 1997), pp. 340-342.
International Preliminary Report on Patentability dated Mar. 15, 2018 issued in corresponding International Application No. PCT/us2016/049415.
International Preliminary Report on Patentability dated Oct. 17, 2017 issued in corresponding International Application No. PCT/US2016/027764.
Fermann, M.E. et al. "Ultrawide tunable Er solition fiber laser amplified in Yb-doped fiber", Optics Letters, vol. 24, No. 20 (Oct. 15, 1999), pp. 1428-1430.
Golubovic, B. et al. "Optical frequency-domain reflectometry using rapid wavelength tuning of a Cr4+forsterite laser", Optics Letters, vol. 22, No. 22 (Nov. 15, 1997), pp. 1704-1706.
Harris Jr., J.S. "Tunable Long-Wavelength Vertical-Cavity Lasers: The Engine of Next Generation Optical Networks?", IEEE Journal on Selected Topics in Quantum Electronics, vol. 6, No. 6 (Nov./Dec. 2000), pp. 1145-1160.
Kakuta, T. et al. "Behavior of optical fibers under heavy irradiation", Fusion Engineering and Design, vol. 41 (1998), pp. 201-205.
Meuwissen, M. et al. "Role of Variability in Microvascular Resistance onFractional Flow Reserve and Coronary Blood Flow Velocity Reserve in Intermediate Coronary Lesions", Circulation, 103 (2001), pp. 184-187 [online—retrieved on Mar. 7, 2018]. Retrieved from the Internet URL: http://circ.ahajournals.org/content/103/2/184.
NKT Photonics. "ESM-12 Single0mode 12 urn core fiber" technical specification sheet.
MKT Photonics. "HC-1550-02 Hollow Core Photonic Bandgap Fiber" technical specification sheet.
MKT Photonics. "HC-800-02 Hollow Core Photonic Bandgap Fiber" technical specification sheet.
Reed, W.A. et al. "Gradient-index fiber-optic microprobes for minimally invasive in vivo low-coherence interferometry", Optics Letters, vol. 27, No. 20 (Oct. 15, 2002), pp. 1794-1796.
Tearney, G.J. et al. "High-speed phase- and group-delay scanning with a grating-based phase control delay line", Optics Letters, vol. 22, No. 23 (Dec. 1, 1997), pp. 1811-1813.
Von der Weid, J.P. et al. "On the Characterization of Optical Fiber Network Components with Optical Frequency Domain Reflectometry", Journal of Lightwave Technology, vol. 15, No. 7 (Jul. 1997), pp. 1131-1141.

(56) References Cited

OTHER PUBLICATIONS

Youngquist, R.C. et al."Optical coherence-domain reflectometry: a new optical evaluation technique", Optics Letters, vol. 12, No. 3 (Mar. 1987), pp. 158-160.
Yun, S.H. et al. "High-speed optical frequency-domain imaging", Optics Express, vol. 11, No. 22 (Nov. 3, 2003), pp. 2953-2963.
Zheng, W. "Optic Lenses Manufactured on Fiber Ends", IEEE, 978-1-4673-7732-4/15, 2015, pp. 1-10.
Ofili, E.O. et al. "Differential characterization of blood flow, velocity, and vascular resistance between proximal and distal normal epicardial human coronary arteries: Analysis by intracoronary Doppler spectral flow velocity", American Heart Journal (Jul. 1995), pp. 37-46.
International Search Report and Written Opinion dated Jul. 30, 2020 issued in corresponding International Application No. PCT/US20/33953.
Chinese Notice of Allowance and Supplementary Search Report dated Jan. 13, 2021 issued in corresponding Chinese Application No. 201680034490.4.
Japanese Office Action dated Nov. 17, 2020 issued in corresponding Japanese Application No. 2018-505582, with English translation.
Japanese Office Action dated Mar. 16, 2021 issued in corresponding Japanese Application No. 2018-510969, with English language summary.
International Search Report and Written Opinion dated Aug. 2, 2021 issued in corresponding International Application No. PCT/US2021/029836.
European Office Action dated Apr. 21, 2021 issued in corresponding European Application No. 16842796.1.
Extended European Search Report dated Nov. 26, 2021 issued in corresponding European Application No. 18883166.3.
International Preliminary Report on Patentability dated Nov. 11, 2021 issued in related International Application No. PCT/US20/30616.
International Preliminary Report on Patentability dated Dec. 2, 2021 issued in related International Application No. PCT/US2020/033953.

* cited by examiner

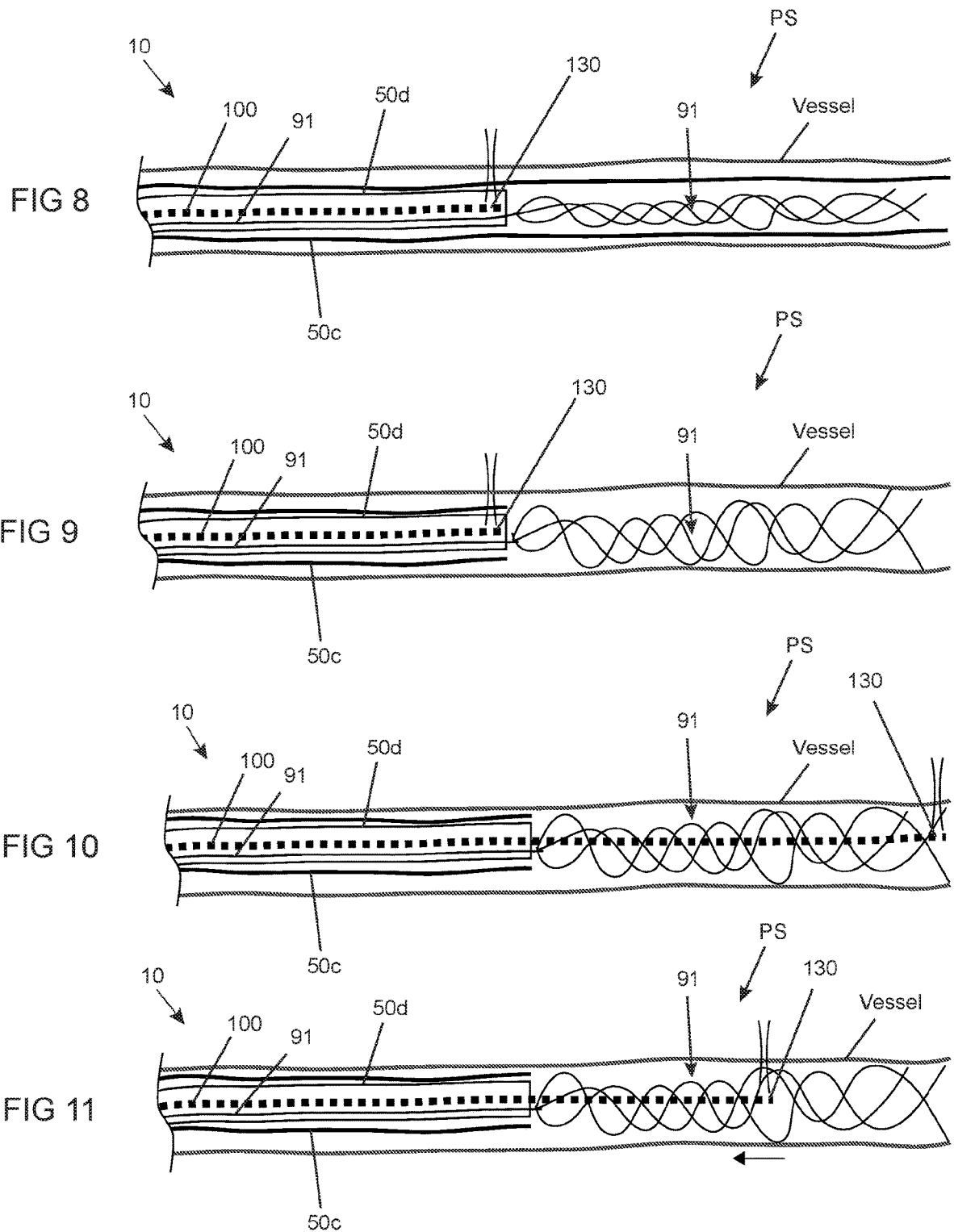

MICRO-OPTIC PROBES FOR NEUROLOGY

RELATED APPLICATIONS

This application claims the benefit of: U.S. Patent Provisional Application Ser. No. 62/322,182, titled "Micro Optic Probes for Neurology", filed Apr. 13, 2016 and U.S. Provisional Application Ser. No. 62/148,355, titled "Micro-Optic Probes for Neurology", filed Apr. 16, 2015, the content of each of which is incorporated herein by reference in its entirety for all purposes. This application is related to: U.S. Provisional Application Ser. No. 62/212,173, titled "Imaging System includes Imaging Probe and Delivery Devices", filed Aug. 31, 2015; the content of which is incorporated herein by reference in its entirety for all purposes.

FIELD

Inventive concepts relate generally to imaging systems, and in particular, neural imaging systems including imaging probes, imaging consoles and delivery devices.

BACKGROUND

Imaging probes have been commercialized for imaging various internal locations of a patient, such as an intravascular probe for imaging a patient's heart. Current imaging probes are limited in their ability to reach certain anatomical locations due to their size and rigidity. Current imaging probes are inserted over a guidewire, which can compromise their placement and limit use of one or more delivery catheters through which the imaging probe is inserted. There is a need for imaging systems that include probes with reduced diameter, high flexibility and ability to be advanced to a patient site to be imaged without a guidewire, as well as systems with one or more delivery devices compatible with these improved imaging probes.

SUMMARY

According to one aspect of the present inventive concepts, an imaging system for a patient comprises: an imaging probe and is configured to produce an image of the patient. The imaging probe comprises: an elongate shaft for insertion into the patient and comprising a proximal end, a distal portion, and a lumen extending between the proximal end and the distal portion; a rotatable optical core comprising a proximal end and a distal end, the rotatable optical core configured to optically and mechanically connect with an interface unit; a probe connector positioned on the elongate shaft proximal end and surrounding at least a portion of the rotatable optical core; and an optical assembly positioned in the elongate shaft distal portion and proximate the rotatable optical core distal end, the optical assembly configured to direct light to tissue and collect reflected light from the tissue.

In some embodiments, the imaging probe comprises a shear-thinning fluid located within the distal portion of the elongate shaft, such as a shear-thinning fluid configured to reduce undesired rotational variances of the rotatable optical core (e.g. and the attached optical assembly 130) while avoiding excessive loads being placed on the rotatable optical core.

In some embodiments, the imaging probe further comprises at least one space reducing element positioned between the elongate shaft and the rotatable optical core, and the at least one space reducing element can be configured to reduce rotational speed variances of the rotatable optical core. The at least one space reducing element can be positioned at least in a portion of the elongate shaft distal portion. The at least one space reducing element can be configured to reduce the rotational speed variances by increasing the shear-thinning of the shear-thinning fluid.

In some embodiments, the imaging probe further comprises an inertial assembly configured to reduce rotational speed variances of the rotatable optical core.

In some embodiments, the imaging probe further comprises an impeller attached to the rotatable optical core and configured to resist rotation of the rotatable optical core when the rotatable optical core is retracted.

In some embodiments, the imaging probe further comprises a stiffening element embedded into the elongate shaft that is configured to resist flexing of the elongate shaft and comprises an optically transparent portion.

In some embodiments, the imaging probe further comprises a reduced inner diameter portion of the elongate shaft, wherein the reduced inner diameter portion is configured to reduce rotational speed variances of the rotatable optical core.

In some embodiments, the imaging system is configured to create a three dimensional image by retraction of the elongate shaft.

In some embodiments, the imaging system is configured to detect and/or quantify malapposition of a flow diverter implanted in the patient.

In some embodiments, the imaging system is configured to provide quantitative and/or qualitative information used to determine the size of a flow diverter to be implanted in the patient and/or position a flow diverter in the patient. The quantitative and/or qualitative information can comprise information related to a parameter selected from the group consisting of: perforator location; perforator geometry; neck size; flow diverter mesh density; and combinations thereof.

In some embodiments, the imaging system is configured to image a stent retriever at least partially positioned in thrombus of the patient. The imaging system can be configured to image thrombus at least one of: thrombus not engaged with the stent retriever or thrombus not removed by the stent retriever.

In some embodiments, the imaging system is configured to quantify a volume of thrombus in the patient. The quantified thrombus can comprise thrombus selected from the group consisting of: residual thrombus in acute stroke; thrombus remaining after a thrombus removal procedure; thrombus present after flow diverter implantation; and combinations thereof.

In some embodiments, the imaging system is configured to provide implant site information, and the implant site information is used to select a particular implantable device for implantation in the patient. The system can further comprise the implantable device for implantation in the patient, and the implantable device can comprise a device selected from the group consisting of: stent; flow diverter; and combinations thereof. The implantable device can be selected based on an implantable device parameter selected from the group consisting of: porosity; length; diameter; and combinations thereof.

In some embodiments, the imaging system is configured to provide porosity information of a device implanted in the patient. The porosity information can comprise porosity of a portion of the implanted device that is to be positioned proximate a sidebranch of a vessel in which the implanted device is positioned. The system can be configured to provide the porosity information based on a wire diameter of the implanted device. The system can further comprise the implanted device, and the implanted device can comprise a device selected from the group consisting of: stent; flow diverter; and combinations thereof. The imaging system can be further configured to provide information related to implanting a second device in the patient. The first implanted device can comprise a stent, and the second implanted device can comprise a flow diverter. The first implanted device can comprise a flow diverter and the second implanted device can comprise a flow diverter. The imaging system can be further configured to provide an image during deployment of the implanted device. The imaging system can be further configured to allow modification of the implanted device while the optical assembly is positioned proximate the implanted device. The modification can comprise a modification of the porosity of the implanted device. The system can further comprise a balloon catheter configured to perform the porosity modification.

In some embodiments, the imaging system is configured to image at least one perforator artery of the patient. The at least one perforator artery can comprise a diameter of at least 50 μm. The system can further comprise a therapeutic device. The therapeutic device can comprise a device selected from the group consisting of: stent retriever; embolization coil; embolization coil delivery catheter; stent; covered stent; stent delivery device; aneurysm treatment implant; aneurysm treatment implant delivery device; flow diverter; balloon catheter; and combinations thereof.

In some embodiments, the system further comprises at least one guide catheter. The at least one guide catheter can comprise a microcatheter. The microcatheter can comprise an inner diameter between 0.0165" and 0.027". The microcatheter can comprise an inner diameter between 0.021" and 0.027".

In some embodiments, the imaging probe is constructed and arranged to access a vessel of a human being.

In some embodiments, the imaging probe is configured to access blood vessels of the brain.

In some embodiments, the elongate shaft comprises a material selected from the group consisting of: FEP; PTFE; Pebax; PEEK; Polyimide; Nylon; and combinations thereof.

In some embodiments, the elongate shaft comprises a material selected from the group consisting of: stainless steel; nickel titanium alloy; and combinations thereof.

In some embodiments, the elongate shaft comprises a first portion comprising a metal tube and a second portion comprising a braided shaft.

In some embodiments, the elongate shaft comprises a hydrophobic material configured to reduce changes in length of the elongate shaft when the elongate shaft is exposed to a fluid.

In some embodiments, the elongate shaft comprises an outer diameter that varies along the length of the elongate shaft.

In some embodiments, the elongate shaft comprises an inner diameter that varies along the length of the elongate shaft.

In some embodiments, the elongate shaft comprises an outer diameter between 0.006" and 0.022".

In some embodiments, the elongate shaft comprises an outer diameter of approximately 0.0134".

In some embodiments, the elongate shaft comprises an inner diameter between 0.004" and 0.012". The elongate shaft can comprise a wall thickness of approximately 0.003".

In some embodiments, the elongate shaft comprises an outer diameter less than or equal to 500 μm.

In some embodiments, the elongate shaft comprises an outer diameter less than or equal to 1 mm.

In some embodiments, the elongate shaft comprises an outer diameter of approximately 0.016". At least the most distal 30 cm of the elongate shaft can comprise an outer diameter less than or equal to 0.016".

In some embodiments, the elongate shaft can comprise an outer diameter of approximately 0.014". The elongate shaft can be configured to be advanced through vasculature without a guidewire or delivery device. At least the most distal 30 cm of the elongate shaft can comprise an outer diameter less than or equal to 0.014".

In some embodiments, the elongate shaft comprises a mid portion proximal to the distal portion, and the distal portion comprises a larger outer diameter than the mid portion. The elongate shaft distal portion can comprise a larger inner diameter than the inner diameter of the mid portion. The larger outer diameter distal portion can surround the optical assembly.

In some embodiments, the elongate shaft comprises a length of at least 100 cm. The elongate shaft can comprise a length of no more than 350 cm.

In some embodiments, the elongate shaft comprises a length of at least 200 cm. The elongate shaft can comprise a length of at least 220 cm. The elongate shaft can comprise a length of at least 240 cm. The elongate shaft can comprise a length of approximately 250 cm.

In some embodiments, the elongate shaft further comprises a middle portion, and the elongate shaft distal portion comprises a larger inner diameter than the elongate shaft middle portion. The elongate shaft distal portion inner diameter can be at least 0.002" larger than the inner diameter of the elongate shaft middle portion. The elongate shaft distal portion can comprise a similar outer diameter to the outer diameter of the elongate shaft middle portion. The elongate shaft distal portion can comprise an outer diameter than is greater than the elongate shaft middle portion outer diameter. The elongate shaft distal portion outer diameter can be at least 0.001" larger than the outer diameter of the elongate shaft middle portion. The elongate shaft distal portion can comprise a wall thickness that is less than the elongate shaft middle portion wall thickness. The elongate shaft distal portion can comprise a stiffer material than the elongate shaft middle portion. The elongate shaft distal portion can comprise a stiffening element.

In some embodiments, the elongate shaft distal portion comprises a rapid exchange guidewire lumen. The guidewire lumen can comprise a length of less than or equal to 150 mm. The guidewire lumen can comprise a length of at least 15 mm. The guidewire lumen can comprise a length of at least 25 mm.

In some embodiments, the elongate shaft distal portion comprises an optically transparent window, and the optical assembly is positioned within the optically transparent window. The optically transparent window can comprise a length less than 20 mm, or less than 15 mm. The optically transparent window can comprise a material selected from the group consisting of: Pebax; Pebax 7233; PEEK; amorphous PEEK; polyimide; glass; sapphire; nylon 12; nylon 66; and combinations thereof. The elongate shaft can comprise at least a first portion, positioned proximate the optically transparent window, and the first portion can comprise a braided shaft. The elongate shaft can further comprise a second portion positioned proximal to the first portion, and the second portion can comprise a metal tube. The optically transparent window can comprise a length between 1 mm and 100 mm. The optically transparent window can comprise a length of approximately 3 mm. The optically transparent window can comprise a material selected from the group consisting of: nylon; nylon 12; nylon 66; and combinations thereof.

In some embodiments, the elongate shaft comprises a stiffening element. The stiffening element can be positioned at least in the elongate shaft distal portion. The stiffening element can be constructed and arranged to resist rotation of the elongate shaft distal portion during rotation of the rotatable optical core. The stiffening element can terminate proximal to the optical assembly. The stiffening element can comprise a coil. The stiffening element can comprise metal coils wound over PTFE. The stiffening element can comprise a coil wound in a direction such that rotation of the rotatable optical core tightens the metal coil. The imaging probe can further comprise a fluid positioned between the rotatable optical core and the elongate shaft, and the metal coil can be configured to reduce twisting of the elongate shaft by torque forces applied by the fluid.

In some embodiments, the elongate shaft comprises a distal end, and the imaging probe comprises a spring tip attached to the elongate shaft distal end. The spring tip can comprise a radiopaque portion. The spring tip can comprise a length between 2 cm and 3 cm.

In some embodiments, the elongate shaft comprises a proximal portion constructed and arranged to be positioned in a service loop, and the elongate shaft proximal portion has a different construction than the remainder of the elongate shaft. The different construction can comprise a larger outer diameter. The different construction can comprise a thicker wall.

In some embodiments, the system further comprises a fluid positioned in the elongate shaft lumen, and a fluid interacting element positioned in the distal portion of the lumen of the elongate shaft, and the fluid interacting element is configured to interact with the fluid to increase load on the rotatable optical core during rotation of the rotatable optical core. The fluid interacting element can comprise a coil positioned in the elongate shaft lumen. The fluid interacting element can comprise a non-circular cross section of the lumen. The non-circular cross section can comprise a geometry selected from the group consisting of: polygon shaped cross section of a lumen of the elongate shaft; projections into a lumen of the elongate shaft; recesses in inner diameter of the elongate shaft; and combinations thereof. The fluid can comprise a low viscosity fluid. The fluid can comprise a viscosity at or below 1000 Cp.

In some embodiments, the imaging probe further comprises a first sealing element located within the elongate shaft lumen, the sealing element positioned between the rotatable optical core and the elongate shaft, and configured to slidingly engage the rotatable optical core and to resist the flow of fluid around the sealing element (e.g. to provide a seal as the rotatable optical core is rotated). The first sealing element can be positioned in the elongate shaft distal portion. The imaging probe can further comprise a first liquid positioned proximate the optical assembly and a second fluid positioned proximate the rotatable optical core, and the first sealing element can be positioned between the first liquid and the second liquid. The first liquid can comprise a first viscosity and the second liquid can comprise a second viscosity greater than the first viscosity. The first sealing element can be further configured to resist rotation of the rotatable optical core. The first sealing element can comprise a hydrogel. The first sealing element can comprise an adhesive bonded to the elongate shaft. The first sealing element can comprise a UV-cured adhesive bonded to the elongate shaft. The rotatable optical core can comprise a material that does not bond to the adhesive. The first sealing element can comprise a compliant material. The compliant material can comprise silicone. The system can further comprise a second sealing element positioned between the rotatable optical core and the elongate shaft, and the second sealing element can be configured to slidingly engage the rotatable optical core and can be further configured to resist flow of fluid around the second sealing element, and the imaging probe can further comprise a fluid positioned between the first sealing element and the second sealing element. The first and second sealing elements can be separated by a distance of between 1 mm and 20 mm. The fluid positioned between the first and second sealing elements can comprise a viscosity between 10 Cp and 100 Cp. The first sealing element can be positioned proximal and proximate the optical assembly and the second sealing element can be positioned distal to the first sealing element.

In some embodiments, the imaging probe comprises a sealing element positioned proximate the proximal end of the elongate shaft. The sealing element can be positioned between the elongate shaft and the probe connector.

In some embodiments, the rotatable optical core comprises a single mode glass fiber with an outer diameter between 40 µm and 175 µm.

In some embodiments, the rotatable optical core comprises a single mode glass fiber with an outer diameter between 80 µm and 125 µm.

In some embodiments, the rotatable optical core comprises a polyimide coating.

In some embodiments, the rotatable optical core comprises an outer diameter between 60 µm and 175 µm. The rotatable optical core can comprise an outer diameter of approximately 110 µm.

In some embodiments, the rotatable optical core comprises a material selected from the group consisting of: silica glass; plastic; polycarbonate; and combinations thereof.

In some embodiments, the rotatable optical core comprises a numerical aperture of approximately 0.11.

In some embodiments, the rotatable optical core comprises a numerical aperture of at least 0.11.

In some embodiments, the rotatable optical core comprises a numerical aperture of approximately 0.16.

In some embodiments, the rotatable optical core comprises a numerical aperture of approximately 0.20.

In some embodiments, the rotatable optical core is constructed and arranged to rotate in a single direction.

In some embodiments, the rotatable optical core is constructed and arranged to rotate in two directions.

In some embodiments, the rotatable optical core is configured to be retracted within the elongate shaft. The system can further comprise purge media introduced between the rotatable optical core and the elongate shaft. The purge media can provide a function selected from the group consisting of: index matching; lubrication; purging of bubbles; and combinations thereof.

In some embodiments, the optical assembly comprises an outer diameter between 80 µm and 500 µm. The optical assembly can comprise an outer diameter of approximately 150 µm.

In some embodiments, the optical assembly comprises an outer diameter of at least 125 µm.

In some embodiments, the optical assembly comprises a length between 200 µm and 3000 µm. The optical assembly can comprise a length of approximately 1000 µm.

In some embodiments, the optical assembly comprises a lens. The lens can comprise a GRIN lens. The lens can comprise a focal length between 0.5 mm and 10.0 mm. The lens can comprise a focal length of approximately 2.0 mm. The lens can comprise a ball lens.

In some embodiments, the optical assembly comprises a reflecting element.

In some embodiments, the optical assembly comprises a lens, a reflecting element and a connecting element, and the connecting element positions the reflecting element relative to the lens. The connecting element can comprise an element selected from the group consisting of: tube; flexible tube; heat shrink; optically transparent arm; and combinations thereof. The connecting element can position the reflecting element a distance of between 0.01 mm and 3.0 mm from the lens. The connecting element can position the reflecting element a distance of between 0.01 mm and 1.0 mm from the lens. The reflecting element can comprise a cleaved portion of a larger assembly. The reflecting element can comprise a segment of a wire. The wire can comprise a gold wire. The lens can comprise a GRIN lens. The lens can have at least one of an outer diameter of 150 µm or a length of 1000 µm. The lens can further comprise a coreless lens positioned proximal to and optically connected to the GRIN lens.

In some embodiments, the imaging probe comprises the inertial assembly, and the inertial assembly is positioned proximate the optical assembly.

In some embodiments, the imaging probe comprises the inertial assembly, and the inertial assembly further comprises a wound hollow core cable comprising a proximal end and a distal end, the distal end of the wound hollow core cable being affixed to the rotatable optical core at a location proximal to the optical assembly, and the proximal end of the wound hollow core cable being unattached to the optical core.

In some embodiments, the imaging probe comprises the inertial assembly, and the inertial assembly comprises fluid within the elongate shaft lumen and a mechanical resistance element positioned on the distal portion of the optical core, and the mechanical resistance element is in contact with the fluid and configured to resist rotation of the rotatable optical core.

In some embodiments, the imaging probe comprises the inertial assembly, and the inertial assembly is constructed and arranged to provide inertial dampening which increases with rotational speed.

In some embodiments, the imaging probe comprises the inertial assembly, and the inertial assembly comprises a projection from the rotatable optical core. The projection can be constructed and arranged to frictionally engage the elongate shaft. The projection can be constructed and arranged to cause shear force that applies a load to the rotatable optical core during rotation.

In some embodiments, the imaging probe comprises the inertial assembly, and the inertial assembly comprises a projection from the elongate shaft. The projection can be constructed and arranged to frictionally engage the rotatable optical core. The projection can be constructed and arranged to cause shear force that applies a load to the rotatable optical core during rotation. The projection can be created by a thermal processing of the elongate shaft.

In some embodiments, the imaging probe comprises the inertial assembly, and the inertial assembly comprises a compressed portion from the elongate shaft. The system can further comprise at least one band configured to crimp the elongate shaft to create the compressed portion.

In some embodiments, the imaging probe comprises the inertial assembly, and the inertial assembly comprises the impeller.

In some embodiments, the imaging probe comprises the impeller, and the impeller is constructed and arranged to cause wind-up loading of the rotatable optical core during rotation.

In some embodiments, the imaging probe comprises the impeller and the imaging probe further comprises fluid in a lumen, and the impeller is configured to engage the fluid during rotation of the rotatable optical core.

In some embodiments, the imaging probe comprises the impeller, and the impeller comprises a turbine.

In some embodiments, the imaging probe comprises the impeller, and the impeller is configured to frictionally engage the elongate shaft during rotation of the rotatable optical core.

In some embodiments, the imaging probe comprises the impeller, and the impeller comprises a vane-type micro structure.

In some embodiments, the imaging probe comprises the impeller, and the impeller comprises a flywheel.

In some embodiments, the imaging probe comprises the stiffening element.

In some embodiments, the imaging probe comprises the stiffening element, and the stiffening element comprises a wire coil embedded in the elongate shaft, and the wire spiral geometry and a pullback spiral rotational pattern of the optical assembly are matched but offset by approximately one-half of a wire spiral, such that an imaging beam of the optical assembly passes between the wire spirals during pullback.

In some embodiments, the imaging probe comprises the stiffening element, and the stiffening element comprises a wound wire formed over the rotatable optical core.

In some embodiments, the imaging probe comprises the stiffening element, and the stiffening element comprises a stiffening member embedded in the elongate shaft, and the stiffening member geometry and a pullback spiral pattern of the optical assembly are matched but offset by approximately one-half of a wire spiral, such that an imaging beam of the optical assembly passes between the wire spirals during pullback.

In some embodiments, the imaging probe comprises the reduced portion of the elongate shaft. The imaging probe can comprise at least one band crimped about the elongate shaft and constricting the elongate shaft to create the reduced portion of the elongate shaft. At least one band can provide a seal to be formed between the rotatable core and the elongate shaft. The reduced portion of the elongate shaft can comprise a thermally treated portion of the elongate shaft.

In some embodiments, the imaging probe further comprises a fluid positioned within the lumen of the elongate shaft. The fluid can be configured to reduce variances in rotational speed of the rotatable optical core. The system can further comprise a sealing element positioned proximate the proximal end of the elongate shaft, and the seal can be configured to maintain the fluid within the lumen. The fluid can comprise a first fluid positioned around the optical assembly and a second fluid positioned around the rotatable optical core. The first fluid can comprise a first viscosity and the second fluid can comprise a second viscosity greater than the first viscosity. The second fluid can be constructed and arranged to reduce variances in rotational speed of the rotatable optical core. The system can further comprise a sealing element positioned between the first fluid and the second fluid. The fluid can comprise a gel. The fluid can comprise a shear-thinning fluid. The fluid can comprise a shear-thinning gel. The fluid can be configured to provide lubrication. The fluid can be configured to cause the rotatable optical core to tend to remain centered in the elongate shaft during rotation of the rotatable optical core. The first fluid can comprise a viscosity between 10 Pa-S and 100,000 Pa-S. The first fluid can be configured to reduce in viscosity to a level of approximately 3 Pa-S at a shear rate of 100 s−1. The fluid can comprise a lubricant configured to reduce friction between the rotatable optical core and the elongate shaft. The fluid can comprise a first fluid and a second fluid, and the second fluid can be positioned within the elongate shaft proximate the optical assembly, and the first fluid can be positioned within the elongate shaft proximal to the second fluid. The imaging probe can further comprise a sealing element in between the first fluid and the second fluid. The sealing element can be positioned between 1 mm and 20 mm from the optical assembly. The sealing element can be positioned approximately 3 mm from the optical assembly. The first fluid can comprise a viscosity between 10 Pa-S and 100,000 Pa-S. The first fluid can comprise a shear-thinning fluid. The first fluid can be configured to reduce in viscosity to a level of approximately 3 Pa-S at a shear rate of 100 s−1. The first fluid material can comprise a fluid selected from the group consisting of: hydrocarbon-based material; silicone; and combinations thereof. The second fluid can comprise a viscosity between 1 Pa-S and 100 Pa-S. The second fluid can comprise a viscosity of approximately 10 Pa-S. The second fluid can comprise a fluid selected from the group consisting of: mineral oil; silicone; and combinations thereof. The imaging system can be configured to pressurize the fluid in the lumen. The imaging system can be constructed and arranged to perform the pressurization of the fluid to reduce bubble formation and/or bubble growth. The imaging system can be configured to pressurize the fluid in the lumen to a pressure of at least 100 psi. The imaging system can comprise a pressurization assembly configured to perform the pressurization of the fluid. The pressurization assembly can comprise a check valve. The fluid can comprise a lubricant. The lubricant can be configured to reduce friction between the rotatable optical core and the elongate shaft when at least a portion of the elongate shaft is positioned proximate and distal to the carotid artery. The fluid can comprise a high viscosity fluid. The elongate shaft can be constructed and arranged to expand when the fluid is pressurized. The elongate shaft can be constructed and arranged to expand to a first inner diameter when the fluid is at a first pressure. The elongate shaft can be constructed and arranged to expand to a second inner diameter when the fluid is at a second pressure. The elongate shaft can be constructed and arranged to become more rigid when the fluid is pressurized. The elongate shaft can be constructed and arranged to increase space between the rotatable optical core and the elongate shaft during the expansion by the pressurized fluid. The elongate shaft can be constructed and arranged to remain at least partially expanded when the fluid pressure is reduced.

In some embodiments, the imaging probe further comprises a torque shaft with a proximal end and a distal end, and the torque shaft can be fixedly attached to the rotatable optical core such that rotation of the torque shaft rotates the rotatable optical core. The torque shaft can comprise stainless steel. The torque shaft can comprise an outer diameter between 0.02" and 0.09". The torque shaft can comprise an outer diameter of approximately 0.025". The torque shaft can comprise a length of approximately 49 cm. The torque shaft can comprise a dimension selected from the group consisting of: an inner diameter of approximately 0.015"; an outer diameter of approximately 0.025"; and combinations thereof. The torque shaft can comprise a wall thickness between 0.003" and 0.020". The torque shaft can comprise a wall thickness of approximately 0.005". The torque shaft distal end can be positioned within 60 cm of the optical connector. The torque shaft distal end can be positioned within 50 cm of the optical connector. The torque shaft distal end can be positioned at least 50 cm from the optical assembly. The torque shaft distal end can be positioned at least 100 cm from the optical assembly. The imaging system can further comprise a retraction assembly constructed and arranged to retract at least one of the rotatable optical core or the elongate shaft, and the torque shaft distal end can be positioned proximal to the retraction assembly. The imaging probe can further comprise a fixation tube positioned between the torque shaft and the rotatable optical core. The fixation tube can be adhesively attached to at least one of the torque shaft or the rotatable optical core.

In some embodiments, the imaging system further comprises a visualizable marker constructed and arranged to identify the location of the optical assembly on a second image produced by a separate imaging device. The separate imaging device can comprise a device selected from the group consisting of: fluoroscope; ultrasonic imager; MRI; and combinations thereof. The visualizable marker can be positioned on the optical assembly. The visualizable marker can be positioned at a fixed distance from the optical assembly. The imaging system can further comprise a connecting element connecting the visualizable marker to the optical assembly.

In some embodiments, the imaging probe can comprise multiple markers constructed and arranged to provide a rule function. The at least one of the multiple markers can comprise at least one of a sealing element or a rotational dampener. The multiple markers can comprise two or more markers selected from the group consisting of: radiopaque marker; ultrasonically reflective marker; magnetic marker; and combinations thereof. The multiple markers can be positioned on the rotatable optical core. The multiple markers can be positioned on the elongate shaft.

In some embodiments, the imaging system further comprises a console comprising a component selected from the group consisting of: rotation assembly; retraction assembly; imaging assembly; algorithm; and combinations thereof.

In some embodiments, the imaging system further comprises a rotation assembly constructed and arranged to rotate the rotatable optical core. The rotation assembly can comprise a motor. The imaging system can further comprise a retraction assembly constructed and arranged to retract at least one of the rotatable optical core or the elongate shaft. The imaging system can further comprise a translatable slide, and the rotation assembly can be positioned on the translatable slide. The rotation assembly can be constructed and arranged to be positioned independent of the position of the retraction assembly. The retraction assembly can be constructed and arranged to be positioned closer to the patient than the rotation assembly. The rotation assembly can provide motive force to the retraction assembly. The rotation assembly can comprise a drive cable that provides the motive force to the retraction assembly. The elongate shaft can be constructed and arranged to be retracted by the retraction assembly. The elongate shaft can comprise a proximal portion constructed and arranged to provide a service loop during retraction by the retraction assembly. The rotation assembly can rotate the rotatable optical core at a rate between 20 rps and 2500 rps. The rotation assembly can rotate the rotatable optical core at a rate of approximately 250 rps. The rotation assembly can rotate the rotatable optical core at a rate of up to 25,000 rps. The rotation assembly can be constructed and arranged to rotate the rotatable optical core at a variable rate of rotation. The imaging system can further comprise a sensor configured to produce a signal, and the rotational rate can be varied based on the sensor signal. The sensor signal represents a parameter selected from the group consisting of: tortuosity of vessel; narrowing of vessel; presence of clot; presence of an implanted device; and combinations thereof. The rotation assembly can be configured to allow an operator to vary the rate of rotation. The rotation assembly can be configured to automatically vary the rate of rotation. The rotation assembly can be configured to increase the rate of rotation when collecting image data from a target area.

In some embodiments, the imaging system further comprises a retraction assembly constructed and arranged to retract at least one of the rotatable optical core or the elongate shaft. The retraction assembly can be constructed and arranged to retract the rotatable optical core without retracting the elongate shaft. The retraction assembly can be constructed and arranged to retract both the rotatable optical core and the elongate shaft. The retraction assembly can be constructed and arranged to retract the rotatable optical core and the elongate shaft simultaneously. The retraction assembly can be constructed and arranged to retract the rotatable optical core and the elongate shaft in unison. The imaging probe can comprise a fluid between the rotatable optical core and the elongate shaft, and the retraction assembly can be constructed and arranged to perform the retraction while minimizing bubble formation in the fluid. The elongate shaft distal portion can comprise an optically transparent window, and the optical assembly can be positioned within the optically transparent window. The optically transparent window can comprise a length of less than or equal to 6 mm, less than or equal to 15 mm, or less than or equal to 20 mm. The optically transparent window can comprise a length of between 5 mm and 50 mm. The optically transparent window can comprise a length of approximately 10 mm, or approximately 12 mm. The optically transparent window can comprise a length of less than or equal to 4 mm. The optically transparent window can comprise a length of approximately 3 mm. The elongate shaft can comprise an outer diameter less than or equal to 0.025". The elongate shaft can comprise an outer diameter less than or equal to 0.016". The elongate shaft can comprise an outer diameter less than or equal to 0.014". The retraction assembly can be constructed and arranged to retract the elongate shaft. The elongate shaft can comprise a proximal portion constructed and arranged to provide a service loop during retraction by the retraction assembly. The retraction assembly can comprise a telescoping retraction assembly. The telescoping retraction assembly can comprise a disposable motor. The imaging probe can comprise a Tuohy valve and the retraction assembly can operably engage the Tuohy valve during retraction. The retraction assembly can be configured to perform a retraction over a time period of between 0.1 seconds and 10 seconds. The retraction assembly can be configured to perform a retraction over a time period of approximately 4 seconds. The retraction assembly can be constructed and arranged to retract the at least one of the rotatable optical core or the elongate shaft over a distance of approximately 50 mm. The retraction assembly can be constructed and arranged to retract the at least one of the rotatable optical core or the elongate shaft over a distance of approximately 75 mm. The retraction assembly can be constructed and arranged to retract the at least one of the rotatable optical core or the elongate shaft over a distance of between 20 mm and 150 mm. The retraction assembly can be constructed and arranged to have its retraction distance selected by an operator of the system. The retraction assembly can be configured to perform the retraction at a rate between 3 mm/sec and 500 mm/sec. The retraction assembly can be configured to perform the retraction at a rate of approximately 50 mm/sec. The retraction assembly can be constructed and arranged to retract the at least one of the rotatable optical core or the elongate shaft at a variable rate of retraction. The imaging system can further comprise a sensor configured to produce a signal, and the retraction rate can be varied based on the sensor signal. The sensor signal can represent a parameter selected from the group consisting of: tortuosity of vessel; narrowing of vessel; presence of clot; presence of an implanted device; and combinations thereof. The retraction assembly can be configured to allow an operator to vary the retraction rate. The retraction assembly can be configured to automatically vary the retraction rate. The retraction assembly can be configured to decrease the rate of retraction when visualizing a target area. The imaging system can further comprise a catheter device comprising at least one of a vascular introducer or a guide catheter, the elongate shaft insertable through the catheter device, and the retraction assembly can be attachable to the catheter device. The imaging system can further comprise a catheter device comprising at least one of a vascular introducer or a guide catheter, the elongate shaft insertable through the catheter device, and the retraction assembly can be constructed and arranged to be positioned within 20 cm from the catheter device.

In some embodiments, the imaging system further comprises an imaging assembly configured to provide light to the rotatable optical core and to collect light from the rotatable optical core. The imaging assembly can comprise a light source configured to provide the light to the rotatable optical core. The imaging assembly can comprise a fiber optic rotary joint comprising an optical core configured to transmit light to the rotatable optical core and receive light from the rotatable optical core. The rotatable optical core can comprise a fiber with a first numerical aperture, and the imaging assembly can comprise an imaging assembly optical core with a second numerical aperture different than the first numerical aperture. The first numerical aperture can be approximately 0.16 and the second numerical aperture can be approximately 0.11. The imaging system can further comprise an adaptor configured to attach the imaging probe to the imaging assembly. The adaptor can comprise a lens assembly configured to match different numerical apertures. The adaptor can be configured to be used in multiple clinical procedures, but in less procedures than the imaging assembly. The adaptor can comprise a fiber with a numerical aperture chosen to minimize coupling losses between the imaging probe and the imaging assembly. The numerical aperture of the adaptor fiber can be approximately equal to the geometrical mean of the numerical aperture of the rotatable optical core and the numerical aperture of the imaging assembly. The numerical aperture of the adaptor fiber can be approximately equal to the arithmetic mean of the numerical aperture of the rotatable optical core and the numerical aperture of the imaging assembly.

In some embodiments, the imaging system further comprises an algorithm. The imaging system can further comprise a sensor configured to produce a signal, and the algorithm can be configured to analyze the sensor signal. The sensor signal can represent light collected from tissue. The sensor signal can represent a parameter related to:

tortuosity of a blood vessel; narrowing of a blood vessel; presence of clot; presence of implanted device; and combinations thereof.

In some embodiments, the imaging system further comprises at least one guide catheter configured to slidingly receive the imaging probe. The imaging system can further comprise a flushing fluid delivery assembly configured to deliver a flushing fluid between the at least one guide catheter and the imaging probe. The flushing fluid can comprise saline and/or contrast (e.g. radiopaque contrast). The flushing fluid delivery assembly can be configured to deliver flushing fluid at a rate of approximately 6 ml/sec. The imaging system can further comprise the flushing fluid, and the flushing fluid can comprise iodinated contrast including an iodine concentration between 50 mg/ml and 500 mg/ml. The flushing fluid can comprise a fluid whose viscosity ranges from 1.0 Cp to 20 Cp at a temperature of approximately 37° C. The at least one guide catheter can comprise a first guide catheter comprising an optically transparent window, and the optical assembly can be constructed and arranged to be positioned within the optically transparent window. The first guide catheter can comprise a microcatheter with an inner diameter between 0.021" and 0.027". The first guide catheter can comprise a microcatheter with an inner diameter between 0.0165" and 0.027". The at least one guide catheter can further comprise a second guide catheter configured to slidingly receive the first guide catheter.

In some embodiments, the imaging system further comprises a torque tool constructed and arranged to operably engage the elongate shaft and subsequently apply torsional force to the elongate shaft.

According to another aspect of the present inventive concepts, methods of using the imaging system described herein are provided.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

FIG. 1A is magnified view of the distal portion of the shaft of the imaging probe of FIG. 1, consistent with the present inventive concepts.

FIG. 8 is a side sectional anatomical view of a system comprising a guide catheter, an imaging probe and a treatment device, each of which having been placed into a vessel of the patient, consistent with the present inventive concepts.

FIG. 9 is a side sectional anatomical view of the system of FIG. 8, after the guide catheter has been partially retracted, consistent with the present inventive concepts.

FIG. 10 is a side sectional anatomical view of the system of FIG. 8, after the imaging probe has been advanced through the treatment device, consistent with the present inventive concepts.

FIG. 11 is a side sectional anatomical view of the system of FIG. 8, as the imaging probe is being retracted through the treatment device, consistent with the present inventive concepts.

DETAILED DESCRIPTION OF THE DRAWINGS

Figure 1:
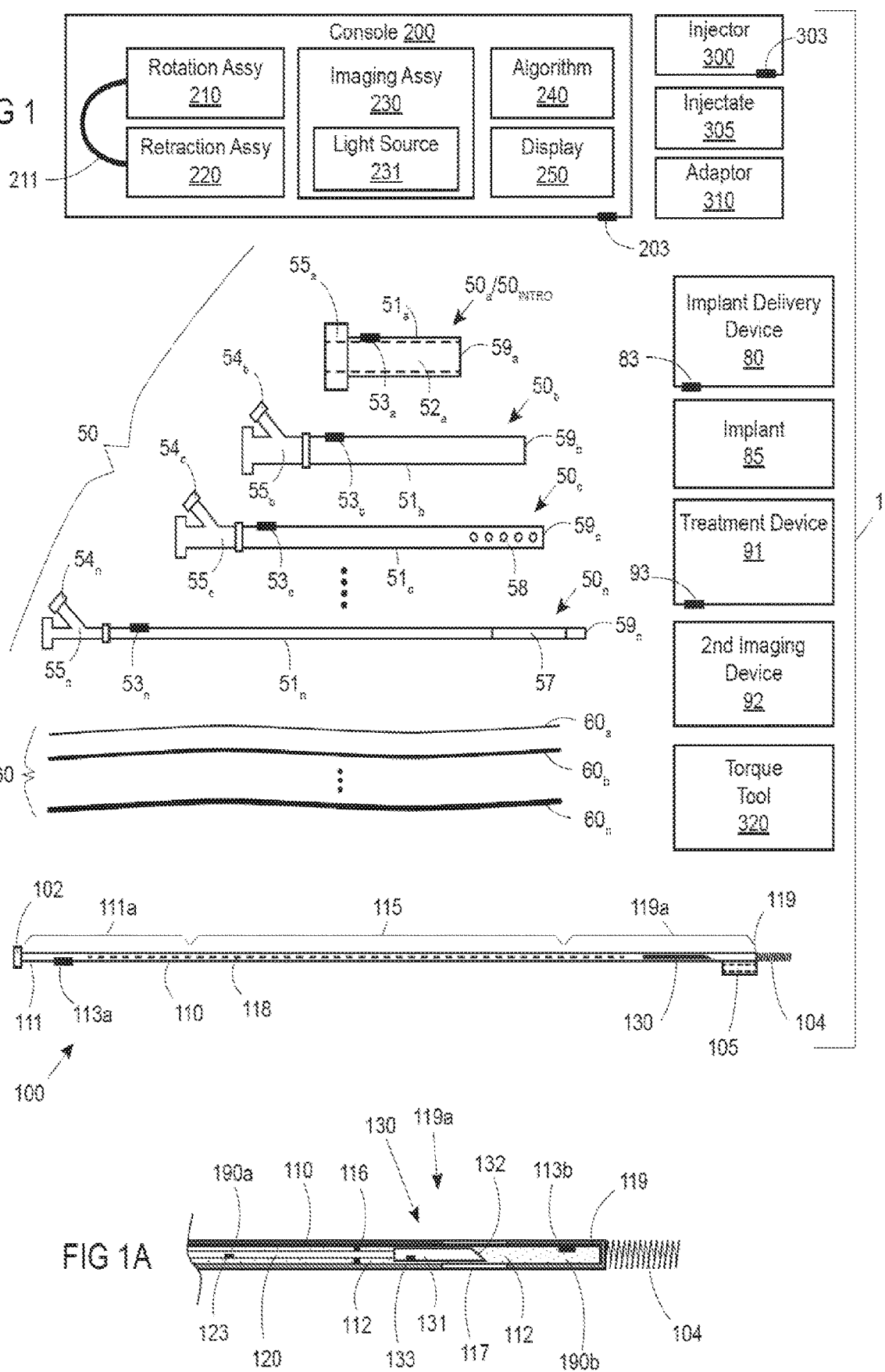
FIG. 1 is a schematic view of an imaging system comprising an imaging probe, an imaging console and one or more delivery devices, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described. Shafts of the present inventive concepts, such as hollow tube shafts comprising a lumen and a wall, include an inner diameter (ID) equal to the diameter of the lumen, and an outer diameter (OD) defined by the outer surface of the shaft.

The terms "major axis" and "minor axis" of a component where used herein are the length and diameter, respectively, of the smallest volume hypothetical cylinder which can completely surround the component.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such light (e.g. a transducer comprising a light emitting diode or light bulb), sound (e.g. a transducer comprising a piezo crystal configured to deliver ultrasound energy), pressure, heat energy, cryogenic energy, chemical energy; mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one or more of these.

As used herein, the term "patient site" refers to a location within the patient, such as a location within a body conduit such as a blood vessel (e.g. an artery or vein) or a segment of the GI tract (e.g. the esophagus, stomach or intestine), or a location with an organ. A "patient site" can refer to a location in the spine, such as within the epidural space or intrathecal space of the spine. A patient site can include a location including one or more of: an aneurysm; a stenosis; thrombus and/or an implant.

As used herein, the term "neural site" refers to a patient site proximate the brain, such as at a location within the neck, head or brain of a patient. A neural site can include a location proximate the brain including one or more of: an aneurysm; a stenosis; thrombus and/or an implant.

As used herein, the term "proximate" shall include locations relatively close to, on, in and/or within a referenced component or other location.

As used herein, the term "transparent" and "optically transparent" refer to a property of a material that is relatively transparent (e.g. not opaque) to light delivered and/or collected by one or more components of the imaging system or probe of the present inventive concepts (e.g. to collect image data of a patient site).

It is appreciated that certain features of the inventive concepts, which are, for clarity, described in the context of separate embodiments, may also be provided in combination in a single embodiment. Conversely, various features of the inventive concepts which are, for brevity, described in the context of a single embodiment, may also be provided separately or in any suitable sub-combination. For example, it will be appreciated that all features set out in any of the claims (whether independent or dependent) can be combined in any given way.

The present inventive concepts include imaging systems comprising imaging probes and one or more delivery devices, such as delivery catheters and/or guidewires. The imaging probe can be configured to be positioned proximate a patient site and to collect image data from the patient site, such as a neural site, spinal site and/or other patient site as defined hereabove. The imaging probe comprises an elongate shaft including a lumen. In some embodiments, a rotatable optical core and a distally positioned optical assembly are positioned within the lumen of the probe shaft. A probe connector can be positioned on the proximal end of the elongate shaft, the connector surrounding at least a portion of the rotatable optical core (e.g. the proximal end of the rotatable optical core). The present inventive concepts further includes methods of introducing the imaging probe to a patient site, such as a neural site, using one or more delivery devices such as delivery catheters and/or guidewires. In some embodiments, the imaging probe is advanced through a delivery catheter to a patient site, without being advanced over a guidewire.

In some embodiments, the imaging probe comprises an inertial assembly configured to reduce rotational speed variances of the rotatable optical core. In some embodiments, the imaging probe comprises an impeller attached to the rotatable optical core and configured to resist rotation of the rotatable optical core, such as when the rotatable optical core is retracted.

In some embodiments, the imaging probe comprises a reinforcing assembly embedded into the elongate shaft. The reinforcing assembly can be configured to resist flexing of the elongate shaft and can comprise an optically transparent portion.

In some embodiments, the imaging probe comprises an elongate shaft in which at least a portion of the shaft includes a reduced inner diameter or otherwise comprises a portion in which the gap between the elongate shaft and the rotatable optical core is reduced. The reduced gap portion can be configured to reduce rotational speed variances of the rotatable optical core. In some embodiments, the reduced gap portion causes the elongate shaft to frictionally engage the rotatable optical core, providing a dampening force configured to reduce undesired speed variances of the rotatable optical core (e.g. to avoid undesired rotational speed variances in the attached optical assembly 130). Alternatively or additionally, a fluid can be positioned in the reduced gap portion (or other locations between the elongate shaft and the rotatable optical core), such as to similarly reduce undesired speed variances of the rotatable optical core. The fluid can comprise a shear-thinning fluid configured to avoid excessive loading on the rotatable optical core (e.g. during high speed rotation to prevent breaking of the rotatable optical core).

Systems, devices and methods of the present inventive concepts can be used to diagnose and/or treat stroke. Stroke is the 4th-leading cause of death in the United States and leads all ailments in associated disability costs. Stroke is a result of vascular disease and comes in two major forms: ischemic, in which the blood supply to the brain is interrupted; and hemorrhagic, in which a ruptured vessel leaks blood directly in the brain tissue. Both forms have associated high morbidity and mortality, such that improved diagnosis and treatment would have a significant impact on healthcare costs.

Imaging of the vessels is the primary diagnostic tool when planning and applying therapies such as: thrombolytic drugs or stent retrievers for clot removal (ischemic stroke); or coils, flow diverters and other devices for aneurysm repair (hemorrhagic stroke). External, non-invasive, imaging technologies, such as x-ray, angiography or MRI, are the primary imaging techniques used, but such techniques provide limited information such as vessel size and shape information with moderate resolution (e.g. approximately 200 µm resolution). Such levels of resolution do not permit the imaging of important smaller perforator vessels present in the vasculature. An inability to adequately image these vessels limits pre-procedural planning as well as acute assessment of therapeutic results. These imaging technologies are further limited in their effectiveness due to the shadowing and local image obliteration that can be created by the therapies themselves (e.g. in the case of implantation of one or more coils). Thus there is a desire to also perform intravascular imaging to examine the detailed morphology of the interior vessel wall and/or to better plan and assess the results of catheter based interventions. Currently, intravascular imaging techniques such as Intravascular Ultrasound (IVUS) and intravascular Optical Coherence Tomography (OCT) have been developed, but are only approved for use in the coronary arteries. IVUS is also used in the larger peripheral vasculature. Currently, intravascular imaging has not been extended for use into the neurological vessels except for the larger carotid arteries. The limitations of current technologies correlate to: the neurological vessel sizes can become very small, on the order of 1 mm in diameter or less, and the vessel tortuosity becomes quite high (e.g. if attempting to navigate the tortuous carotid sinus to reach and image the mid-cranial artery as well as branches and segments above).

Due to the fundamental limits of ultrasound resolution, especially the unavoidable beam spreading when small transducers are used, optical techniques are more appropriate. In particular, with the advent of new light sources such as broad band SLED's, visible wavelength laser diodes, and compact swept-frequency light sources, which are all compatible with single-mode fibers and interferometric imaging such as OCT, the use of optical techniques is highly advantageous both from a clinical performance as well as commercial viewpoint. The use of single mode fibers allows small diameter imaging catheters.

Referring now to FIG. 1, a schematic view of an imaging system comprising an imaging probe and one or more delivery devices is illustrated, consistent with the present inventive concepts. System 10 is constructed and arranged to collect image data and produce an image based on the recorded data, such as when system 10 comprises an Optical Coherence Tomogrophy (OCT) imaging system. System 10 comprises imaging probe 100, and at least one delivery device, such as at least one delivery catheter 50 and/or at least one guidewire 60. System 10 can further comprise an imaging console, console 200 which is configured to operably attach to imaging probe 100. System 10 can further comprise a fluid injector, such as injector 300 which can be configured to inject one or more fluids, such as a flushing fluid, an imaging contrast agent (e.g. a radiopaque contrast agent, hereinafter "contrast") and/or other fluid, such as injectate 305 shown. System 10 can further comprise an implant, such as implant 85 which can be implanted in the patient via implant delivery device 80. System 10 can further comprise a device configured to treat the patient, treatment device 91, which can be configured to dilate a stenotic site, remove stenotic material (e.g. thrombus) and/or otherwise treat a patient disease or disorder. System 10 can further comprise a second imaging device, such as imaging device 92 shown.

Imaging probe 100 comprises an elongate shaft, shaft 110, comprising proximal end 111, distal end 119, proximal portion 111*a*, a middle portion (mid portion 115), and distal portion 119*a*. An optical connector, connector 102 is positioned on the proximal end 111 of shaft 110, such as a connector configured to operably attach probe 100 to console 200 Imaging probe 100 is configured to provide a patient image, such as a three dimensional (3D) image created when shaft 110 of imaging probe 100 is retracted. In some embodiments, imaging probe 100 and/or another component of system 10 is of similar construction and arrangement to the similar components described in applicant's co-pending U.S. Provisional Application Ser. No. 62/148, 355, titled "Micro-Optic Probes for Neurology", filed Apr. 29, 2015, the content of which is incorporated herein in its entirety for all purposes.

Imaging system 10 can comprise one or more imaging probes 100, each suitable for imaging highly tortuous bodily lumens such as the mid-cranial artery, various peripheral arteries, and ducts of the endocrine system such as the liver (bile) and pancreatic ducts. Each imaging probe 100 can comprise very small cross-sections, typically less than 1 mm in OD and contain a rotatable optical core, core 120 comprising a single fiber optically connected on its distal end to an optical assembly, optical assembly 130. Core 120 is rotated to create a high fidelity image of the luminal wall through which probe 100 is inserted. Imaging probe 100 and other components of imaging system 10 can be configured to facilitate uniform rotational velocity of core 120 while imaging probe 100 traverses difficult anatomies. Imaging system 10 can comprise multiple imaging probes 100 provided in a kit configuration, such as when two or more probes 100 comprise different characteristics (e.g. different length, diameter and/or flexibility)

Imaging probe 100 is constructed and arranged to collect image data from a patient site. Distal portion 119*a* can be configured to pass through the patient site, such as a patient site including occlusive material such as thrombus or a patient site including an implant. In some embodiments, probe 100 is constructed and arranged to collect image data from a neural site, such as a neural site selected from the group consisting of: artery of patient's neck; vein of patient's neck; artery of patient's head; vein of patient's head; artery of patient's brain; vein of patient's brain; and combinations of one or more of these. In some embodiments, probe 100 is constructed and arranged to collect image data from one or more locations along or otherwise proximate the patient's spine. In some embodiments, probe 100 is constructed and arranged to collect image data from tissue selected from the group consisting of: wall tissue of a blood vessel of the patient site; thrombus proximate the patient site; occlusive matter proximate the patient site; a blood vessel outside of blood vessel in which optical assembly 130 is positioned; tissue outside of blood vessel in which optical assembly 130 is positioned; extracellular deposits outside of the lumen of the blood vessel in which optical assembly 130 is positioned (e.g. within and/or outside of the blood vessel wall); and combinations of one or more of these. Alternatively or additionally, optical assembly 130 can be constructed and arranged to collect image data from an implanted device (e.g. a temporary or chronically implanted device), such as implant 85 described herebelow or a device previously implanted in the patient. In some embodiments, optical assembly 130 is constructed and arranged to collect image data regarding the placement procedure in which the implant was positioned within the patient (e.g. real time data collected during placement). Optical assembly 130 can be constructed and arranged to collect implant data comprising position and/or expansion data related to placement of an implant or other treatment device, such as a device selected from the group consisting of: a stent retriever (also known as a stentriever); an embolization device such as an embolization coil; an embolization coil delivery catheter; an occlusion device; a stent; a covered stent; a stent delivery device; a flow diverter; an aneurysm treatment device; an aneurysm delivery device; a balloon catheter; and combinations of one or more of these. In some embodiments, optical assembly 130 is constructed and arranged to collect data related to the position of an implant 85 or other device comprising a stimulation element, such as an electrode or other stimulation element positioned proximate the brain (e.g. an electrode positioned in the deep brain or other brain location) or a stimulation element positioned proximate the spine (e.g. stimulation element configured to treat pain by stimulating spine tissue). Implantation of implant 85 can be performed based on an analysis of collected image data (e.g. an analysis of collected image data by algorithm 240). The analysis can be used to modify an implantation parameter selected from the group consisting of: selection of the implantable device (e.g. selection of implant 85); selection of the implantable device porosity; selection of the implantable device metal coverage; selection of the implantable device pore density; selection of the implantable device diameter; selection of the implantable device length; selection of the location to implant the implantable device; a dilation parameter for expanding the implantable device once implanted; a repositioning of the implantable device once implanted; selection of a second implantable device to be implanted; and combinations thereof. An adjustment of the implantation can be performed based on one or more issues identified in the analysis, such as an issue selected from the group consisting of: malposition of implanted device; inadequate deployment of implanted device; presence of air bubbles; and combinations thereof.

In some embodiments, optical assembly 130 is constructed and arranged to collect data related to the position of a treatment device, such as treatment device 91 described herebelow, during a patient treatment procedure.

Delivery catheters 50 can comprise one or more delivery catheters, such as delivery catheters 50*a*, 50*b*, 50*c* through 50*n* shown. Delivery catheters 50 can include a vascular introducer, such as when delivery catheter 50*a* shown in FIG. 1 comprises a vascular introducer, delivery catheter $50_{INTRO}$. Other delivery catheters 50 can be inserted into the patient through delivery catheter $50_{INTRO}$, after the vascular introducer is positioned through the skin of the patient. Two or more delivery catheters 50 can collectively comprise sets of inner diameters (IDs) and outer diameters (ODs) such that a first delivery catheter 50 slidingly receives a second delivery catheter 50 (e.g. the second delivery catheter OD is less than or equal to the first delivery catheter ID), and the second delivery catheter 50 slidingly receives a third delivery catheter 50 (e.g. the third delivery catheter OD is less than or equal to the second delivery catheter ID), and so on. In these configurations, the first delivery catheter 50 can be advanced to a first anatomical location, the second delivery catheter 50 can be advanced through the first delivery catheter to a second anatomical location distal or otherwise remote (hereinafter "distal") to the first anatomical location, and so on as appropriate, using sequentially smaller diameter delivery catheters 50.

Each delivery catheter 50 comprises a shaft 51 (e.g. shafts 51a, 51b, 51c and 51n shown), each with a distal end 59 (e.g. distal ends 59a, 59b, 59c and 59n shown). A connector 55 (e.g. connectors 55a, 55b, 55c and 55n shown) is positioned on the proximal end of each shaft 51. Each connector 55 can comprise a Touhy or other valved connector, such as a valved connector configured to prevent fluid egress from the associated catheter 50 (with and/or without a separate shaft positioned within the connector 55). Each connector 55 can comprise a port 54 as shown on delivery catheters 50b, 50c, and 50n, such as a port constructed and arranged to allow introduction of fluid into the associated delivery catheter 50 and/or for removing fluids from an associated delivery catheter 50. In some embodiments, a flushing fluid, as described herebelow, is introduced via one or more ports 54, such as to remove blood or other undesired material from locations proximate optical assembly 130. Port 54 can be positioned on a side of connector 55 and can include a luer fitting and a cap and/or valve. Shafts 51, connectors 55 and ports 54 can each comprise standard materials and be of similar construction to commercially available introducers, guide catheters, diagnostic catheters, intermediate catheters and microcatheters used in interventional procedures.

Each delivery catheter 50 comprises a lumen 52 (reference number 52 shown on delivery catheter 50a but removed from the remaining delivery catheters 50 for illustrative clarity) extending from the connector 55 to the distal end 59 of shaft 51. The diameter of each lumen 52 defines the ID of the associated delivery catheter 50. Each delivery catheter 50 can be advanced over a guidewire (e.g. guidewire 60) via lumen 52. In some embodiments, a delivery catheter 50 is configured for rapid exchange advancement and retraction over a guidewire, such as via a sidecar with a rapid exchange (Rx) guidewire lumen as is known to those of skill in the art. In some embodiments, probe 100 and at least one delivery catheter 50 are cooperatively constructed and arranged such that the delivery catheter 50 is advanced through a vessel, such as a blood vessel, and probe 100 is slidingly received by the delivery catheter 50 and advanced through the delivery catheter 50 to a location proximate a patient site PS to be imaged (e.g. a location just distal to, within and/or just proximate the patient site PS to be imaged). In some embodiments, a second delivery catheter 50 is slidingly received by a first delivery catheter 50, and probe 100 is advanced through the second delivery catheter 50 to a location proximate a patient site PS to be imaged. In yet other embodiments, three or more delivery catheters 50 are coaxially inserted in each other, with probe 100 advanced through the innermost delivery catheter 50 to a location proximate a patient site PS to be imaged. In some embodiments, probe 100 is advanced through (e.g. through and beyond) one or more delivery catheters 50 without the use of a guidewire.

Delivery catheters 50 can comprise one or more delivery catheters selected from the group consisting of: an introducer; a vascular introducer; an introducer with an ID between 7 Fr and 9 Fr; a delivery catheter (also referred to as a guide catheter) for positioning through the aortic arch (e.g. such that its distal end is just distal or otherwise proximate the aortic arch) such as a delivery catheter with an ID between 5 Fr and 7 Fr or an ID of approximately 6.5 Fr; a delivery catheter (also referred to as an intermediate catheter) for insertion through a larger, previously placed delivery catheter, such as an intermediate delivery catheter with an ID of between 0.053" and 0.070"; a delivery catheter (also referred to as a microcatheter) with an ID of between 0.0165" and 0.027"; and combinations of one or more of these. In some embodiments, delivery catheters 50 comprise a first delivery catheter $50_{INTRO}$ comprising an introducer, such as an introducer with an ID of between 7 Fr and 9 Fr or an ID of approximately 8 Fr. Delivery catheters 50 further can further comprise a second delivery catheter 50 constructed and arranged to be inserted into the first delivery catheter 50, such as a second delivery catheter $50_{GUIDE}$ constructed and arranged for positioning through the aortic arch and comprising an ID between 5 Fr and 7 Fr or an ID of approximately 6 Fr. Delivery catheters 50 can comprise a third delivery catheter 50 constructed and arranged to be inserted through the first delivery catheter $50_{INTRO}$ and/or the second delivery catheter $50_{GUIDE}$, such as a third delivery catheter $50_{INTER}$ (e.g. an intermediate catheter) with an ID of between 0.053" and 0.070". Delivery catheters 50 can comprise a fourth delivery catheter $50_{MICRO}$ constructed and arranged to be inserted through the first, second and/or third delivery catheters 50, such as a fourth delivery catheter $50_{MICRO}$ with an ID of between 0.0165" to 0.027". Imaging probe 100 can be constructed and arranged to be inserted through first, second, third and/or fourth delivery catheters 50, such as when imaging probe 100 comprises an OD of less than 0.070", such as when at least the distal portion of imaging probe 100 comprises an OD of less than or equal to 0.025", 0.022", 0.018", 0.016", 0.015" or 0.014". In some embodiments, at least the distal portion of imaging probe 100 comprises an ID of approximately 0.014" (e.g. an ID between 0.012" and 0.016"). In some embodiments, system 10 comprises a probe 100 and one or more delivery catheters 50.

Each delivery catheter 50 can comprise an optically transparent segment, such as a segment relatively transparent to light transmitted and/or received by optical assembly 130, such as transparent segment 57 shown on delivery catheter 50n and described herein. Transparent segment 57 can comprise a length of up to 50 cm, such as a length of between 1 cm and 15 cm, or a length of up to 2 cm or up to 5 cm. Transparent segment 57 can be part of a delivery catheter 50 comprising a microcatheter with an ID between 0.0165" and 0.027", or between 0.021" and 0.027". System 10 can comprise a first delivery catheter 50 that slidingly receives probe 100 and includes a transparent segment 57, and a second delivery catheter 50 that slidingly receives the first delivery catheter 50.

Each delivery catheter 50 can comprise a spring tip, not shown but such as spring tip 104 described herein as attached to shaft 110 of probe 100.

Guidewires 60 can comprise one or more guidewires, such as guidewires 60a, 60b through 60n shown. Guidewires 60 can comprise one or more guidewires constructed and arranged to support advancement (e.g. intravascular advancement) of probe 100 (e.g. via a rapid exchange lumen in distal portion 119a of shaft 110) and/or a delivery catheter 50 into a patient site PS such as a neural site. Guidewires 60 can comprise one or more guidewires selected from the group consisting of: a guidewire with an OD between 0.035" and 0.038"; a guidewire with an OD between 0.010" and 0.018"; an access length guidewire such as a guidewire with a length of approximately 200 cm; an exchange length guidewire such as a guidewire with a length of approximately 300 cm; a guidewire with a length between 175 cm and 190 cm; a guidewire with a length between 200 cm and 300 cm and/or an OD between 0.014" and 0.016"; a hydrophilic guidewire; a Stryker Synchro™ guidewire; a Terumo guidewire such as the Terumo Glidewire™ guidewire; a Terumo Traxcess™ guidewire; an X-Celerator™ guidewire; an X-Pedion™ guidewire; an Agility™ guidewire; a Bentson™ guidewire; a Coon™ guidewire; an Amplatz™ guidewire; and combinations of one or more of these. In some embodiments, system 10 comprises a probe 100 and one or more guidewires 60. Guidewires 60 can comprise one or more visualizable portions, such as one or more radiopaque or ultrasonically reflective portions.

System 10 can comprise various sets and configurations of delivery catheters 50 and guidewires 60. In some embodiments, delivery catheters 50 comprise a first delivery catheter $50_{INTRO}$ comprising an introducer (e.g. a vascular introducer), and at least two delivery catheters 50 that are inserted through delivery catheter $50_{INTRO}$, these catheters comprising corresponding different sets of IDs and ODs, such as to allow sequential insertion of each delivery catheter 50 through the lumen 52 of a previously placed delivery catheter 50, as described in detail herein. In some embodiments, a first delivery catheter 50 is advanced over a first guidewire 60, and a smaller OD delivery catheter 50 is subsequently advanced over a smaller OD guidewire 60 (e.g. after the first guidewire 60 is removed from the first delivery catheter 50 and replaced with the second guidewire 60). In some embodiments, after image data is collected by an imaging probe 100 positioned within a delivery catheter (e.g. after a retraction in which the image data is collected), imaging probe 100 is removed and replaced with a guidewire 60 over which an additional device can be placed (e.g. another delivery catheter 50, a treatment device 91, an implant delivery device 80 or other device). In some embodiments, probe 100, one or more delivery catheters 50 and/or one or more guidewires 60 are inserted, advanced and/or retracted as described herein.

Probe 100, one or more delivery catheters 50 and/or one or more guidewires 60 can be advanced to a patient site PS through one or more blood vessels (e.g. advancement of or more delivery catheters 50 over a guidewire 60 through one or more arteries or veins). Alternatively or additionally, probe 100, one or more delivery catheters 50 and/or one or more guidewires 60 can be advanced to a patient site PS via a non-blood vessel lumen, such as the epidural and/or intrathecal space of the spine, or via another body lumen or space (e.g. also as can be performed over a guidewire 60).

In some embodiments, one or more delivery catheters 50 comprise a functional element 53 (e.g. functional elements 53a, 53b, 53c and 53n shown). Each functional element 53 can comprise one or more functional elements such as one or more sensors, transducers and/or other functional elements as described in detail herebelow. In some embodiments, shaft 110 comprises a length of at least 100 cm, at least 200 cm, at least 240 cm. In some embodiments, shaft 110 comprises a length of approximately 250 cm. In some embodiments, shaft 110 comprises a length less than or equal to 350 cm, less than or equal to 250 cm, or less than or equal to 220 cm.

In some embodiments, shaft 110 comprises an outer diameter (OD) between 0.005" and 0.022" along at least a portion of its length (e.g. at least a portion of distal portion 119a). In some embodiments, shaft 110 comprises an OD of approximately 0.0134", an OD at or below 0.014" or an OD at or below 0.016", along at least a portion of its length (e.g. along a portion surrounding core 120 and/or optical assembly 130, and/or along at least the most distal 10 cm, 20 cm or 30 cm of shaft 110). In these embodiments, imaging probe 100 can be configured to be advanced and/or retracted without a guidewire or delivery catheter (e.g. when optical assembly 130 and shaft 110 are retracted in unison during collection of image data). In some embodiments, shaft 110 comprises an OD that is less than 1 mm, or less than 500 µm, along at least a portion of its length. In some embodiments, shaft 110 comprises an OD that changes along its length. In some embodiments, distal portion 119a comprises a larger OD than an OD of mid portion 115, such as when the portion of distal portion 119a surrounding optical assembly 130 has a larger OD than an OD of mid-portion 115. In these embodiments, distal portion 119a can comprise a larger or similar ID as an ID of mid portion 115.

In some embodiments, shaft 110 comprises an inner diameter (ID) between 0.004" and 0.012", along at least a portion of its length. In some embodiments, shaft 110 comprises an ID of approximately 0.0074" along at least a portion of its length (e.g. along a portion surrounding core 120 and/or optical assembly 130). In some embodiments, shaft 110 comprises an ID that changes along its length. In some embodiments, distal portion 119a comprises a larger ID than an ID of mid portion 115, such as when the portion of distal portion 119a surrounding optical assembly 130 has a larger ID than an ID of mid-portion 115.

In some embodiments, shaft 110 comprises a wall thickness of 0.001" to 0.005", or a wall thickness of approximately 0.003", along at least a portion of its length (e.g. along a portion surrounding core 120 and/or optical assembly 130. In some embodiments, shaft 110 comprises a thinner wall surrounding at least a portion of optical assembly 130 (e.g. thinner than a portion of the wall surrounding core 120).

In some embodiments, shaft 110 distal portion 119a has a larger ID than mid portion 115 of shaft 110, such as when mid portion 115 has an ID at least 0.002" larger than the ID of distal portion 119a. In these embodiments, the OD of mid portion 115 and the OD of distal portion 119a can be of similar magnitude. Alternatively, the OD of mid portion 115 can be different than the OD of distal portion 119a (e.g. the OD of distal portion 119a can be greater than the OD of mid portion 115, such as when distal portion 119a is at least 0.001" larger).

In some embodiments, imaging probe 100 comprises a stiffened portion, such as when imaging probe 100 comprises stiffening element 118. Stiffening element 118 is positioned in, within and/or along at least a portion of shaft 110. In some embodiments, stiffening element 118 is positioned within or on the inside surface of the wall of shaft 110. In some embodiments, stiffening element 118 comprises a wire wound over core 120. In some embodiments, stiffening element 118 terminates proximal to optical assembly 130. Alternatively, stiffening element 118 can travel lateral to and/or potentially beyond optical assembly 130, such as when the portion of stiffening element 118 comprises one or more optically transparent materials.

In some embodiments, distal portion 119a comprises a wall thickness that is less than the wall thickness of mid portion 115. In some embodiments, distal portion 119a comprises a stiffer material than the materials of mid portion 115, and/or distal portion 119a includes a stiffening element (e.g. stiffening element 118a shown in FIG. 13 herebelow), such as when distal portion 119a comprises a wall thickness less than the wall thickness of mid portion 115.

In some embodiments, probe 100 comprises a guidewire lumen, such as a rapid exchange guidewire lumen positioned in a sidecar 105 shown in FIG. 1. Sidecar 105 can comprise a length of less than 150 mm. Sidecar 105 can comprise a length of at least 15 mm, such as a length of approximately 25 mm.

In some embodiments, proximal portion 111a of shaft 110 is configured to be positioned in a service loop. Shaft 110 proximal portion 111a can comprise a different construction than mid portion 115 or different than distal portion 119a. For example, proximal portion 111a can comprise a larger OD than mid portion 115 or a thicker wall than mid portion 115.

Figure 14:
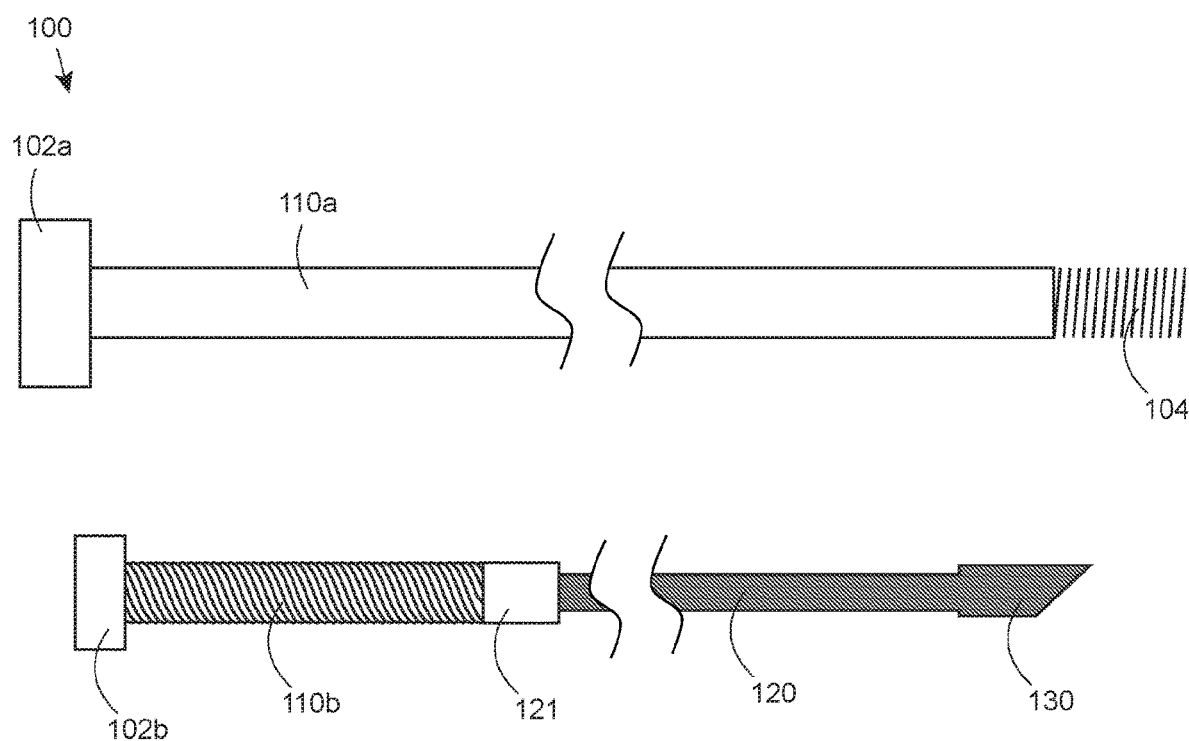
FIG. 14 is partially assembled view of an imaging probe comprising a shaft, rotatable optical core, and torque shaft, consistent with the present inventive concepts.

In some embodiments, shaft 110 comprises an outer shaft and an inner "torque" shaft, which can be shorter than the outer shaft, such as is described herebelow in reference to FIG. 14. In some embodiments, the torque shaft terminates prior to a portion of probe 100 that enters the patient.

In some embodiments, system 10 comprises torque tool 320, a tool that frictionally engages shaft 110 of probe 100 (e.g. from a lateral direction at a location along proximal portion 111a), and allows an operator to apply torsional force to shaft 110.

Referring additionally to FIG. 1A, a magnified view of distal portion 119a is illustrated, consistent with the present inventive concepts. A lumen 112 extends from proximal end 111 of shaft 110 to distal portion 119a, ending at a location proximal to distal end 119. Positioned within lumen 112 is a rotatable optical core, core 120. An optical assembly, optical assembly 130 is positioned on the distal end of core 120. Optical assembly 130 includes lens 131, and a reflecting surface, reflector 132. Optical assembly 130 is positioned within an optically translucent and/or effectively transparent window portion of shaft 110, viewing portion 117. Optical assembly 130 is constructed and arranged to collect image data through at least a portion of shaft 110. In some embodiments, optical assembly 130 is further constructed and arranged to collect image data through at least a portion of an additional device, such as at least a portion of a shaft of a delivery catheter 50 (e.g. an optically transparent portion of a delivery catheter 50, such as transparent segment 57 described herein). In FIG. 1A, optional components sidecar 105 and stiffening element 118 have been removed for illustrative clarity.

In some embodiments, a fluid 190 is included in lumen 112 (e.g. in the space not occupied by core 120 and optical assembly 130), such as fluid 190a and fluid 190b shown in FIG. 1A where fluid 190b is positioned around optical assembly 130, and fluid 190a is positioned around core 120 proximal to optical assembly 130. Fluid 190 (e.g. fluid 190b) can comprise an optically transparent fluid. In some embodiments, fluid 190a and fluid 190b comprise similar materials. Alternatively or additionally, fluid 190a and fluid 190b can comprise dissimilar materials. In some embodiments, fluid 190a comprises a more viscous fluid than fluid 190b. Fluid 190a and/or 190b (singly or collectively fluid 190) can be constructed and arranged to limit undesired variations in rotational velocity of core 120 and/or optical assembly 130. In some embodiments, fluid 190 comprises a gel. In some embodiments, fluid 190 comprises a non-Newtonian fluid (e.g. a shear-thinning fluid) or other fluid whose viscosity changes with shear. Alternatively or additionally, fluid 190 can comprise a lubricant (e.g. to provide lubrication between core 120 and shaft 110). In some embodiments, fluid 190 comprises a shear-thinning fluid, and core 120 is rotated at a rate above 50 Hz, such as a rate above 100 Hz or 200 Hz. At higher rotation rates, if fluid 190 comprised a high viscosity Newtonian fluid, the resultant viscous drag during rotation of core 120 would result in a torsional load on core 120 which would cause it to break before the high rotation could be reached. However, a fluid 190 comprising a low viscosity Newtonian fluid is also not desired, as it would not provide sufficient dampening (e.g. would not provide adequate rotational speed control), such as during low-speed ("idle-mode") imaging. For these reasons, probe 100 can comprise a fluid 190 that is a relatively high viscosity, shear-thinning (non-Newtonian) fluid, that provides sufficient loading during low speed rotation of core 120 and, due to its varying viscosity, avoid excessive loading during high speed rotation of core 120. In some embodiments, fluid 190 comprises a shear-thinning fluid whose viscosity changes non-linearly (e.g. its viscosity rapidly decreases with increasing shear rate). In some embodiments, probe 100 comprises a reduced gap between shaft 110 and core 120 along at least a portion of shaft 110 (e.g. a portion of shaft 110 proximal to optical assembly 130), such as via a space reducing element as described herebelow in reference to FIG. 16. This gap can range from 20 μm to 200 μm (e.g. a constant or varied gap between 20 μm and 200 μm). Fluid 190 (e.g. a high viscosity, shear-thinning fluid) can be positioned (at least) in the reduced gap portion of shaft 110. In this configuration, the amount of force applied to core 120 to reduce rotational variation is proportional to the shear stress and the length of shaft 110 in which fluid 190 and shaft 110 interact (the "interaction length"). Positioning of this interaction length relatively proximate to optical assembly 130 optimizes reduction of undesired rotational velocity variation of optical assembly 130 (e.g. since core 120 can have low torsional rigidity, dampening sufficiently far from optical assembly 130 will not provide the desired effect upon optical assembly 130).

In some embodiments, optical assembly 130 comprises a lens 131 with an OD that is greater than the diameter of lumen 112 of shaft 110 (e.g. greater than the diameter of at least a portion of lumen 112 that is proximal to optical assembly 130). The OD of lens 131 being greater than the diameter of lumen 112 prevents optical assembly 130 from translating within lumen 112. For example, lens 131 can comprise a relatively large diameter aperture lens, such as to provide a small spot size while collecting large amounts of light (e.g. a lens 131 with an OD approaching up to 350 μm). Lumen 112 can be less than this diameter (e.g. less than 350 μm), such as to allow a reduced OD of shaft 110 proximal to optical assembly 130 (e.g. as shown in FIGS. 4, 5, 6, 12, 13 and 16). In embodiments in which the OD of optical assembly 130 is greater than the diameter of lumen 112 at locations proximal to optical assembly 130, the portion of shaft 110 surrounding optical assembly 130 has a larger OD and/or ID than the portions of shaft 110 proximal to optical assembly 130. In these embodiments, both shaft 110 and optical assembly 130 are retracted simultaneously during collection of image data, since lumen 112 has too small a diameter to accommodate translation of optical assembly 130.

In some embodiments, fluid 190 (e.g. fluid 190a) comprises a fluid with a viscosity between 10 Pa-S and 100,000 Pa-S. In these embodiments, fluid 190 can be configured to thin to approximately 3 Pa-S at a shear rate of approximately 100 s$^{-1}$. In some embodiments, fluid 190 (e.g. fluid 190b) comprises a viscosity between 1 Pa-S and 100 Pa-S, such as a viscosity of approximately 10 Pa-S. In some embodiments, fluid 190 is configured to cause core 120 to tend to remain centered within lumen 112 of shaft 110 as it rotates (e.g. due to the shear-thinning nature of fluid 190). In some embodiments, fluid 190a comprises a hydrocarbon-based material and/or silicone. In some embodiments, fluid 190b comprises mineral oil and/or silicone. In some embodiments, probe 100 includes one or more fluids 190 in at least the most distal 20 cm of shaft 110.

In some embodiments, a seal is included in lumen 112, sealing element 116, constructed and arranged to provide a seal between core 120 and the walls of shaft 110 (e.g. when positioned within distal portion 119a). Sealing element 116 can allow for the rotation of core 120, while preventing the mixing and/or migrating of fluids 190a and/or 190b (e.g. by resisting the flow of either around seal 116). In some embodiments, a sealing element 116 is positioned between 1 mm and 200 from optical assembly 130, such as when sealing element 116 is positioned approximately 3 mm from optical assembly 130. In some embodiments, sealing element 116 comprises two or more sealing elements, such as two or more sealing elements 116 which slidingly engage core 120 and/or optical assembly 130. In some embodiments, probe 100 comprises a sealing element positioned in a proximal portion of shaft 110 (e.g. within or proximate connector 102), such as sealing element 151 described herebelow in reference to FIG. 7.

Sealing element 116 and/or 151 can comprise an element selected from the group consisting of: a hydrogel material; a compliant material; silicone; and combinations of one or more of these. In some embodiments, sealing element 116 and/or 151 can comprise a material bonded to shaft 110 with an adhesive, or simply an adhesive itself on shaft 110 (e.g. a UV cured adhesive or an adhesive configured not to bond with core 120).

Figure 7:
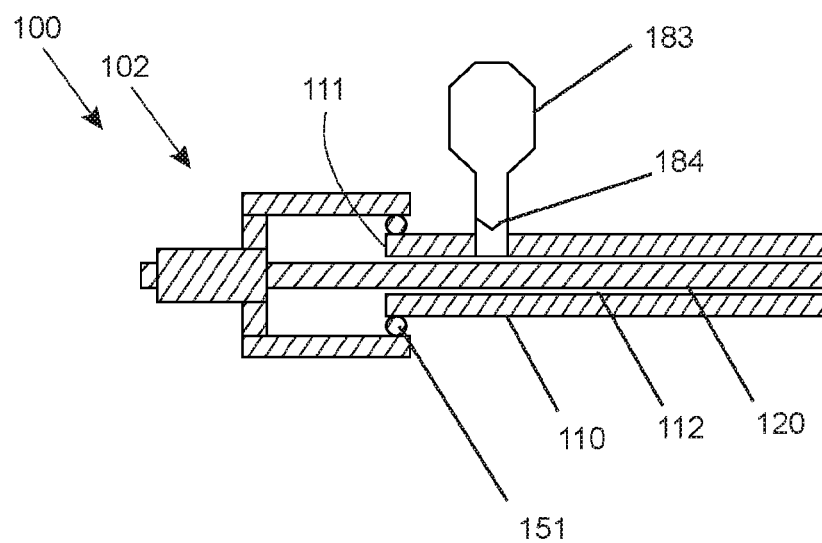
FIG. 7 is a side sectional view of a proximal portion of an imaging probe comprising a pressurization element, consistent with the present inventive concepts.

In some embodiments, fluid 190 is configured to be pressurized, such as is described herein in reference to FIG. 7, such as to reduce bubble formation and/or bubble growth within fluid 190.

Shaft 110 can comprise one or more materials, and can comprise at least a portion which is braided and/or includes one or more liners, such as a polyimide or PTFE liner. In some embodiments, at least the distal portion 119a of shaft 110 comprises an OD less than or equal to 0.025", such as an OD less than or equal to 0.022", 0.018", 0.016", 0.015" or 0.014". In some embodiments, shaft 110 comprises a material selected from the group consisting of: polyether ether ketone (PEEK); polyimide; nylon; fluorinated ethylene propylene (FEP); polytetrafluoroethylene (PTFE); polyether block amide (Pebax); and combinations of one or more of these. In some embodiments, shaft 110 comprises at least a portion including a braid including stainless steel and/or a nickel titanium alloy, such as a shaft 110 including a braid positioned over thin walled FEP or PTF. The braided portion can be coated with Pebax or other flexible material. In some embodiments, shaft 110 comprises at least a portion (e.g. a proximal portion) that is metal, such as a metal hypotube comprising stainless steel and/or nickel titanium alloy. In some embodiments, shaft 110 comprises a first portion that is a metal tube, and a second portion, distal to the first portion, that comprises a braided shaft. In some embodiments, shaft 110 comprises at least a portion that comprises a hydrophobic material or other material configured to reduce changes (e.g. changes in length) when exposed to a fluid.

Viewing portion 117 of shaft 110 can comprise one or more materials, and can comprise similar or dissimilar materials to a different portion of shaft 110. Viewing portion 117 can comprise a similar ID and/or OD as one or more other portions of shaft 110. In some embodiments, viewing portion 117 comprises an ID and/or OD that is larger than an ID and/or OD of shaft 110 at mid portion 115 of shaft 110. Viewing portion 117 can comprise a similar or dissimilar flexibility as one or more other portions of shaft 110. Viewing portion 117 can comprise one or more optically transparent materials selected from the group consisting of: Pebax; Pebax 7233; PEEK; amorphous PEEK; polyimide; glass; sapphire; nylon 12; nylon 66; and combinations of one or more of these.

In some embodiments, a flexible tip portion is positioned on the distal end of shaft 110, such as spring tip 104 shown. Spring tip 104 can comprise a length of between 0.5 cm and 5 cm, such as a length of approximately 1 cm, 2 cm or 3 cm, or a length between 2 cm and 3 cm. At least a portion of spring tip 104 can be made visible to an imaging apparatus, such as by including a radiopaque material such as platinum or other material visible to an X-ray imaging device. Spring tip 104 can comprise a core comprising a material such as stainless steel.

In some embodiments, probe 100 and/or other components of system 10 comprise one or more markers (e.g. radiopaque or other visualizable markers), sensors, transducers or other functional elements such as: functional elements 53a-n of delivery catheters 50; functional element 83 of implant delivery device 80; functional element 93 of treatment device 91; functional elements 113a and 113b (singly or collectively functional element 113, described herebelow) of shaft 110; functional element 123 of core 120; functional element 133 of optical assembly 130; functional element 203 of console 200; and functional element 303 of injector 300.

In some embodiments, core 120 comprises a single mode glass fiber, such as a fiber with an OD between 40 μm and 175 μm, a fiber with an OD between 80 μm and 125 μm, a fiber with an OD between 60 μm and 175 μm, or a fiber with an OD of approximately 110 μm. Core 120 can comprise a material selected from the group consisting of: silica glass; plastic; polycarbonate; and combinations of one or more of these. Core 120 can comprise a fiber with a coating, such as a polyimide coating. Core 120 can comprise cladding material and/or coatings surrounding the fiber, such as are known to those of skill in the art. Core 120 can comprise a numerical aperture (NA) of at or above 0.11, such as an NA of approximately 0.16 or 0.20. In some embodiments, core 120 can comprise an NA (e.g. an NDA between 0.16 and 0.20) to significantly reduce bend-induced losses, such as would be encountered in tortuous anatomy. System 10 can be configured to rotate core 120 in a single direction (uni-directional rotation) or multi-directional (bi-directional rotation).

In some embodiments, probe 100 and other components of system 10 are configured to retract core 120 within shaft 110. In these embodiments, probe 100 can be configured such that a material (e.g. fluid 190) is introduced into and within shaft 110 (e.g. between core 120 and shaft 110). The introduced material can be configured to provide a function selected from the group consisting of: index matching; lubrication; purging of bubbles; and combinations of one or more of these.

In some embodiments, optical assembly 130 comprises an OD between 80 µm and 500 µm, such as an OD of at least 125 µm, or an OD of approximately 150 µm. In some embodiments, optical assembly 130 comprises a length of between 200 µm and 3000 µm, such as a length of approximately 1000 µm. Optical assembly 130 can comprise one or more lenses, such as lens 131 shown, such as a GRIN lens and/or a ball lens. Optical assembly 130 can comprise a GRIN lens with a focal length between 0.5 mm and 100 mm, such as approximately 2.0 mm. Optical assembly 130 can comprise one or more reflecting elements, such as reflecting element 132 shown.

Figure 18:
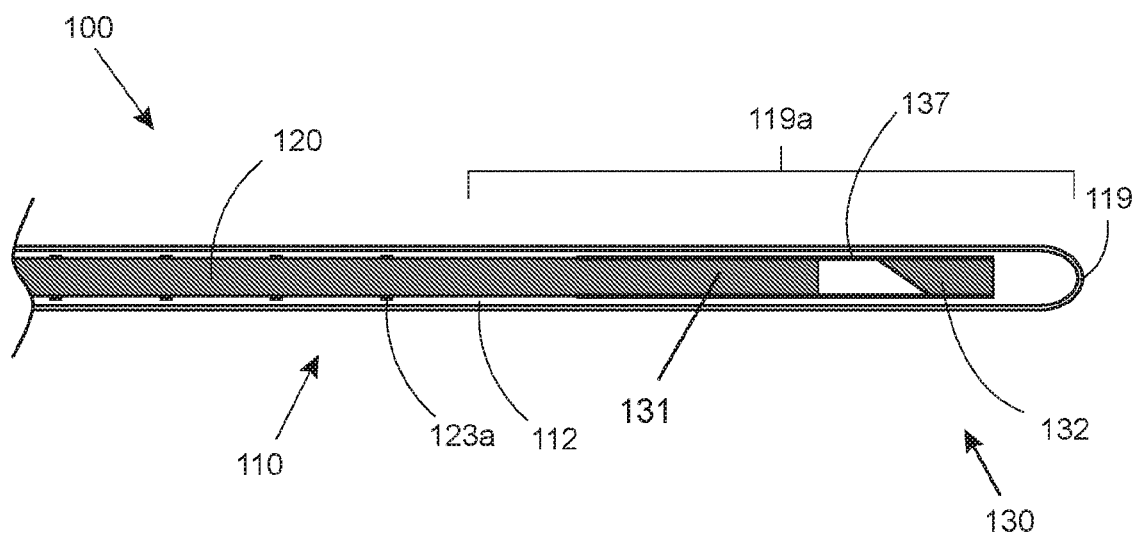
FIG. 18 is a side sectional view of the distal portion of an imaging device comprising a lens and deflector separated and connected by a projection, consistent with the present inventive concepts.

In some embodiments, optical assembly 130 comprises a lens 131 and a reflecting element 132 which is positioned offset from lens 131 via one or more connecting elements 137 as shown in FIG. 18. Connecting element 137 can comprise a tube (e.g. a heat shrink tube) surrounding at least a portion of lens 131 and reflecting element 132. Connecting element 137 can comprise one or more elements selected from the group consisting of: tube; flexible tube; heat shrink; optically transparent and combinations of one or more of these. Connecting element 137 can position reflecting element 132 at a distance of between 0.01 mm and 3.0 mm from lens 131, such as at a distance between 0.01 mm and 1.0 mm. Reflecting element 132 can comprise a partial portion of a larger assembly that is cut or otherwise separated (e.g. cleaved) from the larger assembly during a manufacturing process used to fabricate optical assembly 130. Use of the larger assembly can simplify handling during manufacturing. In some embodiments, the resultant reflecting element 132 comprises a shape-optimized reflector. Reflecting element 132 can comprise a segment of wire, such as a gold wire. In these embodiments, lens 131 can comprise a GRIN lens, such as a lens with an OD of approximately 150 µm and/or a length of approximately 1000 µm. In some embodiments, lens 131 further comprises a second lens, such as a coreless lens positioned proximal to and optically connected to the GRIN lens.

In some embodiments, imaging probe 100 comprises a reduced diameter portion (e.g. a reduced outer and/or inner diameter portion) along shaft 110, at a location proximal to optical assembly 130, such as is shown in FIGS. 4, 5, 6, 12, 13 and 16. In these embodiments, optical assembly 130 can comprise an OD that is larger than lumen 112 of shaft 110 (e.g. at a location proximal to optical assembly 130), such as to provide a larger lens 131 for improved imaging capability. In some embodiments, probe 100 comprises a space reducing element between shaft 110 and core 120, such as is described herebelow in reference to elements 122 of FIG. 16. Functional elements 113 and/or 123 can comprise a space reducing element (e.g. a projection from shaft 110 and/or core 120, respectively).

Console 200 can comprise an assembly, rotation assembly 210 constructed and arranged to rotate at least core 120. Rotation assembly 210 can comprise one or more motors configured to provide the rotation, such as a motor selected from the group consisting of: DC motor; AC motor; stepper motor; synchronous motor; and combinations of one or more of these. Console 200 can comprise an assembly, retraction assembly 220, constructed and arranged to retract at least shaft 110. Retraction assembly 220 can comprise one or more motors or linear drive elements configured to provide the retraction, such as a component selected from the group consisting of: DC motor; AC motor; stepper motor; synchronous motor; gear mechanism, linear drive mechanism; magnetic drive mechanism; piston; pneumatic drive mechanism; hydraulic drive mechanism; and combinations of one or more of these. Rotation assembly 210 and/or retraction assembly 220 can be of similar construction and arrangement to those described in applicant's co-pending application U.S. Provisional Application Ser. No. 62/148,355, titled "Micro-Optic Probes for Neurology", filed Apr. 29, 2015; the content of which is incorporated herein by reference in its entirety for all purposes.

Console 200 can comprise an imaging assembly 230 configured to provide light to optical assembly 130 (e.g. via core 120) and collect light from optical assembly 130 (e.g. via core 120). Imaging assembly 230 can include a light source 231. Light source 231 can comprise one or more light sources, such as one or more light sources configured to provide one or more wavelengths of light to optical assembly 130 via core 120. Light source 231 is configured to provide light to optical assembly 130 (via core 120) such that image data can be collected comprising cross-sectional, longitudinal and/or volumetric information related to the patient site PS or implanted device being imaged. Light source 231 can be configured to provide light such that the image data collected includes characteristics of tissue within the patient site PS being imaged, such as to quantify, qualify or otherwise provide information related to a patient disease or disorder present within the patient site PS being imaged. Light source 231 can be configured to deliver broadband light and have a center wavelength in the range from 800 nm to 1700 nm. The light source 231 bandwidth can be selected to achieve a desired resolution, which can vary according to the needs of the intended use of system 10. In some embodiments, bandwidths are about 5% to 15% of the center wavelength, which allows resolutions of between 20 µm and 5 µm, respectively. Light source 231 can be configured to deliver light at a power level meeting ANSI Class 1 ("eye safe") limits, though higher power levels can be employed. In some embodiments, light source 231 delivers light in the 1.3 µm band at a power level of approximately 20 mW. Tissue light scattering is reduced as the center wavelength of delivered light increases, however water absorption also increases. Light source 231 can deliver light at a wavelength approximating 1300 nm to balance these two effects. Light source 231 can be configured to deliver shorter wavelength light (e.g. approximately 800 nm light) to traverse patient sites to be imaged including large amounts of fluid. Alternatively or additionally, light source 231 can be configured to deliver longer wavelengths of light (e.g. approximately 1700 nm light), such as to reduce a high level of scattering within a patient site to be imaged.

Imaging assembly 230 (or another component of console 200) can comprise a fiber optic rotary joint (FORJ) configured to transmit light from light source 231 to core 120, and to receive light from core 120. In some embodiments, core 120 comprises a fiber with a first numerical aperture (NA), and imaging assembly 230 comprises an imaging assembly optical core with a second NA different than the first NA. For example, the first NA (the NA of core 120) can comprise an NA of approximately 0.16 and the second NA (the NA of the imaging assembly optical core) can comprise an NA of approximately 0.11. In some embodiments, system 10 comprises an adaptor 310 configured to optically connect probe 100 to imaging assembly 230 (e.g. a single use or limited use disposable adaptor used in less procedures than imaging assembly 230). Adaptor 310 can comprise a lens assembly configured to "optically match" (e.g. to minimize coupling losses) different numerical apertures (such as the first and second NAs described hereabove). In some embodiments, adaptor 310 comprises a fiber with an NA that is the geometric mean of the two different NAs. In some embodiments, adaptor 310 comprises a fiber with an NA that is the arithmetic mean of the two different NAs.

Rotation assembly 210 can be constructed and arranged to rotate core 120 (and subsequently one or more components of optical assembly 130), at a rotational velocity of approximately 250 rps, or at a rotational velocity between 40 rps and 1000 rps. Rotation assembly 210 can be configured to rotate core 120 at a rate between 20 rps and 2500 rps. In some embodiments, rotation assembly 210 can be configured to rotate core 120 at a rate up to 25,000 rps. In some embodiments, the rotation rate provided by rotation assembly 210 is variable, such as when the rotation rate is varied based on a signal provided by a sensor of system 10, such as when one or more of functional elements 53, 83, 93, 113, 123, 133, 203 and/or 303 comprise a sensor, and algorithm 240 is used to analyze one or more signals from the one or more sensors. In some embodiments, the sensor signal represents the amount of light collected from tissue or other target. In some embodiments, system 10 is configured to vary the rotation rate provided by rotation assembly 210 when the sensor signal correlates to a parameter selected from the group consisting of: tortuosity of vessel in which probe 100 is placed; narrowing of vessel in which probe 100 is placed; presence of clot proximate optical assembly 130; presence of an implanted device proximate optical assembly 130; and combinations thereof. In some embodiments, the rotation rate provided by rotation assembly 210 is varied by an operator of system 10 (e.g. a clinician). Alternatively or additionally, system 10 can vary the rotation rate provided by rotation assembly 210 automatically or at least semi-automatically ("automatically" herein), such as an automatic variation of a rotation rate as determined by one or more signals from one or more sensors as described hereabove. In some embodiments, rotation by rotation assembly 210 is increased (manually or automatically) when optical assembly 130 is collecting image data from a target area.

In some embodiments, rotation assembly 210 is constructed and arranged to rotate core 120 at one rate (e.g. at least 150 rps or approximately 250 rps) during image data collection (i.e. an "imaging mode"), and at a different rate (e.g. a slower rate, such as a rate between 30 rps and 150 rps), during a "preview mode". During preview mode, a "positioning operation" can be performed in which optical assembly 130 is linearly positioned and/or a flush procedure can be initiated. The positioning operation can be configured to visualize bright reflections (e.g. via one or more implants such as an implanted stent, flow director and/or coils). Alternatively or additionally, the preview mode can be configured to allow an operator (e.g. a clinician) to confirm that optical assembly 130 has exited the distal end 59 of a surrounding delivery catheter 50. The preview mode can be configured to reduce time and acceleration forces associated with rotating core 120 at a velocity to accommodate image data collection (e.g. a rotational velocity of at least 150 rps or approximately 250 rps).

Retraction assembly 220 can be constructed and arranged to retract optical assembly 130 (e.g. by core 120 and/or retracting shaft 100) at a retraction rate of approximately 40 mm/sec, such as a retraction rate between 3 mm/sec and 500 mm/sec (e.g. between 5 mm/sec and 60 mm/sec, or approximately 50 mm/sec). Retraction assembly 220 can be constructed and arranged to perform a pullback of between 20 mm and 150 mm (e.g. a pullback of approximately 50 mm or 75 mm), such as a pullback that is performed in a time period between 0.1 seconds and 15.0 seconds, such as a period between 0.1 and 10 seconds, or a period of approximately 4 seconds. In some embodiments, pullback distance and/or pullback rate are operator selectable and/or variable (e.g. manually or automatically). In some embodiments, the pullback distance and/or pullback rate provided by retraction assembly 220 is variable, such as when the pullback distance and/or pullback rate is varied based on a signal provided by a sensor of system 10, such as when one or more of functional elements 53, 83, 93, 113, 133, 203 and/or 303 comprise a sensor, and algorithm 240 is used to analyze one or more signals from the one or more sensors. In some embodiments, the sensor signal represents the amount of light collected from tissue or other target. In some embodiments, system 10 is configured to vary the pullback distance and/or pullback rate provided by retraction assembly 220 when the sensor signal correlates to a parameter selected from the group consisting of: tortuosity of vessel in which probe 100 is placed; narrowing of vessel in which probe 100 is placed; presence of clot proximate optical assembly 130; presence of an implanted device proximate optical assembly 130; and combinations thereof. In some embodiments, the pullback distance and/or pullback rate provided by retraction assembly 220 is varied by an operator of system 10 (e.g. a clinician). Alternatively or additionally, system 10 can vary the pullback distance and/or pullback rate provided by retraction assembly 210 automatically or at least semi-automatically ("automatically" herein), such as an automatic variation of a pullback distance and/or pullback rate as determined by one or more signals from one or more sensors as described hereabove. In some embodiments, pullback distance and/or pullback rate by retraction assembly 220 is varied (increased or decreased, manually or automatically) when optical assembly 130 is collecting image data from a target area.

In some embodiments, retraction assembly 220 and probe 100 are configured such that during image data collection, retraction assembly 220 retracts core 120 without causing translation to shaft 110 (e.g. core 120 retracts within lumen 112 of shaft 110).

In some embodiments, retraction assembly 220 and probe 100 can be configured such that during image data collection, retraction assembly 220 retracts core 120 and shaft 110 in unison. In these embodiments, shaft 110 can comprise a relatively short viewing window, viewing portion 117 surrounding optical assembly 130, since optical assembly 130 does not translate within shaft 110. For example, in these embodiments, viewing portion 117 can comprise a length less than or equal to 20 mm, less than or equal to 15 mm, less than or equal to 6 mm, or less than or equal to 4 mm, such as when viewing portion 117 comprises a length of approximately 3 mm. In some embodiments, viewing portion 117 comprises a length between 5 mm and 50 mm, such as a length of approximately 10 mm or approximately 12 mm. In these embodiments in which optical assembly 130 does not translate within shaft 110, shaft 110 diameter (ID and/or OD) can be reduced at locations proximal to viewing portion 117, such as when the OD of shaft 110 (at least the portion of shaft 110 surrounding and proximate optical assembly), comprises a diameter of less than or equal to 0.025", 0.016" or 0.014". Alternatively or additionally, in these embodiments in which optical assembly 130 does not translate within shaft 110, portions of the shaft proximal to optical assembly 130 (e.g. proximal to viewing portion 117) can include a non-transparent construction, such as a braided construction or a construction using materials such as metal tubing (e.g. nitinol or stainless steel hypotube), such as to improve pushability of probe 100.

Retraction assembly 220 can be configured to minimize formation of bubbles within any fluid (e.g. fluid 190) within shaft 110, such as by retracting shaft 110 and core 120 in unison, or by retracting core 120 at a precision rate to avoid bubble formation. When shaft 110 is retracted, proximal portion 111a can be configured to be positioned in a service loop. Retraction assembly 220 can comprise a translatable slide, and rotation assembly 210 can be positioned on the translatable slide.

Retraction assembly 220 can comprise a telescoping retraction assembly. Retraction assembly 220 can comprise a motor, such as a single use or otherwise sometimes disposable motor, such as a disposable motor that is part of a telescoping retraction assembly.

In some embodiments, rotation assembly 210 can be independently positioned in reference to retraction assembly 220. In some embodiments, retraction assembly 220 is configured to be positioned closer to the patient than the rotation assembly 210 is positioned (e.g. when retraction assembly 220 is positioned within 20 cm of a vascular introducer or other patient introduction device through which probe 100 is inserted). In some embodiments, retraction assembly 220 is configured to removably attach to a patient introduction device, such as to connect to a Touhy connector of a vascular introducer through which probe 100 is inserted, such as a delivery catheter 50 described herein.

In some embodiments, retraction assembly 220 receives "motive force" from console 200, such as via drive shaft 211 that may be operably attached to rotation assembly 210 as shown in FIG. 1.

Console 200 can comprise a display 250, such as a display configured to provide one or more images (e.g. video) based on the collected image data. Imaging assembly 230 can be configured to provide an image on display 250 with an updated frame rate of up to approximately 250 frames per second (e.g. similar to the rotational velocity of core 120). Display 250 can provide a 2-D and/or 3-D representation of 2-D and/or 3-D data.

Console 200 can comprise one or more functional elements, such as functional element 203 shown in FIG. 1. Functional element 203 can comprise one or more functional elements such as one or more sensors, transducers and/or other functional elements as described in detail herebelow.

Console 200 can comprise an algorithm, such as algorithm 240 shown, which can be configured to adjust (e.g. automatically and/or semi-automatically adjust) one or more operational parameters of system 10, such as an operational parameter of console 200, probe 100 and/or a delivery catheter 50. Alternatively or additionally, algorithm 240 can be configured to adjust an operational parameter of a separate device, such as injector 300 or implant delivery device 80 described herebelow. In some embodiments, algorithm 240 is configured to adjust an operational parameter based on one or more sensor signals, such as a sensor signal provided by a sensor-based functional element of the present inventive concepts as described herein (e.g. a signal provided by one or more of functional elements 53, 83, 93, 113, 123, 203 and/or 303). Algorithm 240 can be configured to adjust an operational parameter selected from the group consisting of: a rotational parameter such as rotational velocity of core 120 and/or optical assembly 130; a retraction parameter of shaft 110 and/or optical assembly 130 such as retraction velocity, distance, start position, end position and/or retraction initiation timing (e.g. when retraction is initiated); a position parameter such as position of optical assembly 130; a line spacing parameter such as lines per frame; an image display parameter such as a scaling of display size to vessel diameter; a probe 100 configuration parameter; an injectate 305 parameter such as a saline to contrast ratio configured to determine an appropriate index of refraction; a light source 231 parameter such as power delivered and/or frequency of light delivered; and combinations of one or more of these. In some embodiments, algorithm 240 is configured to adjust a retraction parameter such as a parameter triggering the initiation of the pullback, such as a pullback that is initiated based on a parameter selected from the group consisting of: lumen clearing; injector 300 signal; change in image data collected (e.g. a change in an image, based on the image data collected, that correlates to proper evacuation of blood from around optical assembly 130); and combinations of one or more of these. In some embodiments, algorithm 240 is configured to adjust a probe 100 configuration parameter, such as when algorithm 240 identifies (e.g. automatically identifies via an RF or other embedded ID) the attached probe 100 and adjusts a parameter such as arm path length and/or other parameter as listed above.

Injector 300 can comprise a power injector, syringe pump, peristaltic pump or other fluid delivery device configured to inject a contrast agent, such as radiopaque contrast, and/or other fluids. In some embodiments, injector 300 is configured to deliver contrast and/or other fluid (e.g. contrast, saline and/or Dextran). In some embodiments, injector 300 delivers fluid in a flushing procedure as described herebelow. In some embodiments, injector 300 delivers contrast or other fluid through a delivery catheter 50 with an ID of between 5 Fr and 9 Fr, a delivery catheter 50 with an ID of between 0.53" to 0.70", or a delivery catheter 50 with an ID between 0.0165" and 0.027". In some embodiments, contrast or other fluid is delivered through a delivery catheter as small as 4 Fr (e.g. for distal injections). In some embodiments, injector 300 delivers contrast and/or other fluid through the lumen of one or more delivery catheters 50, while one or more smaller delivery catheters 50 also reside within the lumen 52. In some embodiments, injector 300 is configured to deliver two dissimilar fluids simultaneously and/or sequentially, such as a first fluid delivered from a first reservoir and comprising a first concentration of contrast, and a second fluid from a second reservoir and comprising less or no contrast. Injector 300 can comprise one or more functional elements, such as functional element 303 shown in FIG. 1. Functional element 303 can comprise one or more functional elements such as one or more sensors, transducers and/or other functional elements as described in detail herebelow.

Implant 85 can comprise an implant (e.g. a temporary or chronic implant) for treating one or more of a vascular occlusion or an aneurysm. In some embodiments, implant 85 comprises one or more implants selected from the group consisting of: a flow diverter; a Pipeline™ flow diverter; a Surpass™ flow diverter; an embolization coil; a stent; a Wingspan™ stent; a covered stent; an aneurysm treatment implant; and combinations of one or more of these. Delivery device 80 can comprise a catheter or other tool used to deliver implant 85, such as when implant 85 comprises a self-expanding or balloon expandable portion. Implant delivery device 80 can comprise a functional element, such as functional element 83 shown in FIG. 1. Functional element 83 can comprise one or more functional elements such as one or more sensors, transducers and/or other functional elements as described in detail herebelow. In some embodiments, system 10 comprises a probe 100, one or more implants 85 and/or one or more implant delivery devices 80, such as is described in applicant's co-pending application U.S. Provisional Application Ser. No. 62/212,173, titled "Imaging System includes Imaging Probe and Delivery Devices", filed Aug. 31, 2015; the content of which is incorporated herein by reference in its entirety for all purposes. In some embodiments, probe 100 is configured to collect data related to implant 85 and/or implant delivery device 80 (e.g. implant 85 and/or implant delivery device 80 anatomical location, orientation and/or other configuration data), after implant 85 and/or implant delivery device 80 has been inserted into the patient.

Treatment device 91 can comprise an occlusion treatment or other treatment device selected from the group consisting of: a balloon catheter constructed and arranged to dilate a stenosis or other narrowing of a blood vessel; a drug eluting balloon; an aspiration catheter; a sonolysis device; an atherectomy device; a thrombus removal device such as a stent retriever device; a Trevo™ stentriever; a Solitaire™ stentriever; a Revive™ stentriever; an Eric™ stentriever; a Lazarus™ stentriever; a stent delivery catheter; a microbraid implant; an embolization system; a WEB™ embolization system; a Luna™ embolization system; a Medina™ embolization system; and combinations of one or more of these. In some embodiments, treatment device 91 comprises a therapeutic device selected from the group consisting of: stent retriever; embolization coil; embolization coil delivery catheter; stent; covered stent; stent delivery device; aneurysm treatment implant; aneurysm treatment implant delivery device; flow diverter; balloon catheter; and combinations thereof. In some embodiments, probe 100 is configured to collect data related to treatment device 91 (e.g. treatment device 91 location, orientation and/or other configuration data), after treatment device 91 has been inserted into the patient. Treatment device 91 can comprise a functional element, such as functional element 93 shown in FIG. 1.

$2^{nd}$ Imaging device 92 can comprise an imaging device such as one or more imaging devices selected from the group consisting of: an X-ray; a fluoroscope such as a single plane or biplane fluoroscope; a CT Scanner; an MRI; a PET Scanner; an ultrasound imager; and combinations of one or more of these.

Functional elements 53, 83, 93, 113, 123, 133, 203, and/or 303 can each comprise one or more sensors, transducers and/or other functional elements, as described in detail herebelow.

In some embodiments, a functional element 113 is positioned proximate optical assembly 130 (e.g. functional element 113b positioned distal to optical assembly 130 as shown in FIG. 1A, at the same axial location as optical assembly 130 and/or proximal to optical assembly 130). In some embodiments, imaging probe 100 comprises functional element 113a shown in FIG. 1. Functional element 113a is shown positioned on a proximal portion of shaft 110, however it can be positioned at another probe 100 location such as on, in and/or within connector 102. Functional elements 113a and/or 113b (singly or collectively functional element 113) can each comprise one or more functional elements such as one or more sensors, transducers and/or other functional elements as described in detail herebelow.

In some embodiments, functional element 53, 83, 93, 113, 123, 133, 203 and/or 303 comprise a sensor, such as a sensor configured to provide a signal related to a parameter of a system 10 component and/or a sensor configured to provide a signal related to a patient parameter. Functional element 53, 83, 93, 113, 123, 133, 203 and/or 303 can comprise one or more sensors selected from the group consisting of: a physiologic sensor; a pressure sensor; a strain gauge; a position sensor; a GPS sensor; an accelerometer; a temperature sensor; a magnetic sensor; a chemical sensor; a biochemical sensor; a protein sensor; a flow sensor such as an ultrasonic flow sensor; a gas detecting sensor such as an ultrasonic bubble detector; a sound sensor such as an ultrasound sensor; and combinations of one or more of these. In some embodiments, functional element 53, 83, 93, 113, 123, 133, 203 and/or 303 can comprise one or more physiologic sensors selected from the group consisting of: a pressure sensor such as a blood pressure sensor; a blood gas sensor; a flow sensor such as a blood flow sensor; a temperature sensor such as a blood or other tissue temperature sensor; and combinations of one or more of these. In some embodiments, algorithm 240 is configured to process the signal received by a sensor, such as a signal provided by a sensor as described herein. In some embodiments, functional element 53, 83, 93, 113, 123 and/or 133 comprises a position sensor configured to provide a signal related to a vessel path (e.g. a vessel lumen path) in three dimensions. In some embodiments, functional element 53, 83, 93, 113, 123 and/or 133 comprises a magnetic sensor configured to provide a signal for positioning optical assembly 130 relative to one or more implanted devices (e.g. one or more implants 85 described herein comprising a ferrous or other magnetic portion). In some embodiments, functional element 53, 83, 93, 113, 123 and/or 133 comprises a flow sensor, such as a flow sensor configured to provide a signal related to blood flow through a blood vessel of the patient site PS (e.g. blood flow through a stenosis or other partially occluded segment of a blood vessel). In these embodiments, algorithm 240 can be configured to assess blood flow (e.g. assess the significance of an occlusion), such as to provide information to a clinician regarding potential treatment of the occlusion. In some embodiments, optical assembly 130 comprises functional element 113, such as when optical assembly 130 is constructed and arranged as a sensor that provides a signal related to blood flow. In some embodiments, functional element 53, 83, 93, 113, 123 and/or 133 comprises a flow sensor configured to provide a signal used to co-register vessel anatomic data to flow data, which can be used to provide pre and post intervention modeling of flow (e.g. aneurysm flow), assess risk of rupture and/or otherwise assess adequacy of the intervention. In some embodiments, functional element 53, 83, 93, 113, 123 and/or 133 comprises an ultrasound sensor configured to provide a signal (e.g. image or frequency data) which can be co-registered with near field optical derived information provided by optical assembly 130. In some embodiments, functional element 53, 83, 93 and/or 113 are configured to be deployed by their associated device, such as to implant the functional element (e.g. a sensor-based functional element) into the patient. The implantable functional element 53, 83, 93 and/or 113 can comprise microchip and/or MEMS components. The implantable functional element 53, 83, 93 and/or 113 can comprise at least a portion that is configured to be visualized (e.g. by image data collected by probe 100 and/or a separate imaging device such as second imaging device 92.

In some embodiments, functional element 53, 83, 93, 113, 123, 133, 203 and/or 303 comprise one or more transducers selected from the group consisting of: a heating element such as a heating element configured to deliver sufficient heat to ablate tissue; a cooling element such as a cooling element configured to deliver cryogenic energy to ablate tissue; a sound transducer such as an ultrasound transducer; a vibrational transducer; and combinations of one or more of these.

In some embodiments, functional element 53, 83, 93 and/or 113 comprises a pressure release valve configured to prevent excessive pressure from accumulating in the associated device. In some embodiments, functional element 53, 83, 93 and/or 113 comprises one or more sideholes, such as one or more sideholes used to deliver a fluid in a flushing procedure as described herein.

In some embodiments, functional element 53, 83, 93, 113, 123, 133, 203 and/or 303 comprise a visualizable marker, such as when functional element 53, 83, 93 and/or 113 comprise a marker selected from the group consisting of: radiopaque marker; ultrasonically reflective marker; magnetic marker; ferrous material; and combinations of one or more of these.

Probe 100 is configured to collect image data, such as image data collected during rotation and/or retraction of optical assembly 130. Optical assembly 130 can be rotated by rotating core 120. Optical assembly 130 can be retracted by retracting shaft 110. Optical assembly 130 can collect image data while surrounded by a portion of a shaft of a delivery catheter 50 (e.g. when within a transparent segment 57 of a delivery catheter) and/or when there is no catheter 50 segment surrounding optical assembly 130 (e.g. when optical assembly 130 has been advanced beyond the distal ends 59 of all delivery catheters 50 into which probe 100 is inserted).

During collection of image data, a flushing procedure can be performed, such as by delivering one or more fluids, injectate 305 (e.g. as propelled by injector 300 or other fluid delivery device), to remove blood or other somewhat opaque material (hereinafter non-transparent material) proximate optical assembly 130 (e.g. to remove non-transparent material between optical assembly 130 and a delivery catheter and/or non-transparent material between optical assembly 130 and a vessel wall), such as to allow light distributed from optical assembly 130 to reach and reflectively return from all tissue and other objects to be imaged. In these flushing embodiments, injectate 305 can comprise an optically transparent material, such as saline. Injectate 305 can comprise one or more visualizable materials, as described herebelow. Injectate 305 can be delivered by injector 300 as described hereabove.

Flush rates required for providing clearance around optical assembly 130 can scale inversely with the viscosity of the flush medium. This mathematical relationship can be driven by the downstream draining of the flush medium in the capillary bed. If the capillary bed drains slowly, it is easier to maintain the upstream flush at a pressure at or slightly above native blood pressure, such that fresh blood will not enter the vessel being imaged (e.g. at a location proximate optical assembly 130). Conversely, if the capillary bed drains rapidly, the flush rate will need to increase correspondingly. Since saline (a standard flush medium) has a viscosity about ⅓ that of blood (e.g. 1 Cp vs 3.3 Cp), roughly three times normal flow rate will be required to clear a vessel (in the area proximate optical assembly 130), and such flow rates can pose a risk to vessel integrity. As an alternative, contrast media (e.g. radiopaque contrast media) can be used for flushing. Contrast material has a high viscosity (due to its high iodine concentrations, typically a concentration of approximately 300 mg/ml). System 10 can comprise a flushing fluid comprising contrast, such as contrast with a concentration between 50 mg/ml to 500 mg/ml of iodine (e.g. correlating to viscosities approximately two to five times that of blood). System 10 can comprise a flushing fluid (e.g. a radiopaque or other visualizable flushing fluid) with a viscosity between 1.0 Cp and 20 Cp (e.g. at a temperature of approximately 37° C.).

Alternative or in addition to its use in a flushing procedure, injectate 305 can comprise material configured to be viewed by second imaging device 92, such as when injectate 305 comprise a contrast material configured to be viewed by a second imaging device 92 comprising a fluoroscope or other X-ray device; an ultrasonically reflective material configured to be viewed by a second imaging device 92 comprising an ultrasound imager; and/or a magnetic material configured to be viewed by a second imaging device 92 comprising an MRI.

Injectate 305 can be delivered by one or more delivery catheters 50 (e.g. in the space between a first delivery catheter 50 and an inserted delivery catheter 50, or in the space between a delivery catheter 50 and an inserted probe 100). Injectate 305 delivered in a flushing procedure (or other injectate 305 delivery procedure) can be delivered out the distal end 59 of a delivery catheter 50 (e.g. a distal end 59 positioned proximal to optical assembly 130), such as is described in applicant's co-pending U.S. Provisional Application Ser. No. 62/212,173, titled "Imaging System includes Imaging Probe and Delivery Devices", filed Aug. 31, 2015, the content of which is incorporated herein by reference in its entirety for all purposes. Alternatively or additionally, any delivery catheter 50 can comprise one or more sideholes passing through a portion of the associated shaft 51, such as sideholes 58 shown positioned on a distal portion of delivery catheter 50c. In some embodiments, a delivery catheter 50 comprises a microcatheter comprising sideholes 58 positioned on a distal portion, such as a microcatheter with an ID less than 0.027" (e.g. a microcatheter with an ID between 0.016" and 0.027" or an ID between 0.021" and 0.027"). In some embodiments, flushing fluid is delivered towards optical assembly 130 from both sideholes 58 and from the distal end 59 of a delivery catheter 50. Sideholes 58 can be constructed and arranged to allow a flushing fluid to pass from within shaft 51 and through the sideholes 58, such as when a separate shaft is inserted within the delivery catheter 50 (e.g. a shaft 51 of an additional delivery catheter 50 or the shaft 110 of probe 100). Delivery of flushing fluid through sideholes 58 and/or the distal end of the delivery catheter 50 can be performed to clear blood from an area from a luminal segment surrounding optical assembly 130, such as during collecting of image data.

In some embodiments, the delivery of injectate 305 during a flushing procedure is based on a parameter selected from the group consisting of: a pre-determined volume of injectate to be delivered; a pre-determined time during which injectate is delivered; an amount of time of delivery including a time extending from a time prior to retraction of shaft 110 that continued until the collecting of the image data has been completed (e.g. completion of retraction of shaft 110); and combinations of one or more of these. In some embodiments, injector 300 delivers fluid in a flushing procedure with an approximate flow profile selected from the group consisting of: contrast (e.g. between 20% and 100% contrast that can be mixed with saline) at 5 ml/second for 6 seconds (e.g. for imaging of a carotid artery including 4 seconds of collecting image data); contrast (e.g. between 20% and 100% contrast that can be mixed with saline) at 4 ml/second for 6 seconds (e.g. for imaging of a vertebral artery including 4 seconds of collecting image data); and combinations of one or more of these. In some embodiments, a flushing procedure comprises delivery of injectate 305 (e.g. via one or more delivery catheters 50) for between 2 seconds to 8 seconds, such as a delivery of injectate for approximately 4 seconds (e.g. to purge blood or other non-transparent fluid from a luminal segment of a blood vessel or other area surrounding optical assembly 130 during collection of image data from a patient site PS). In similar flushing procedures, injectate 305 can be delivered at a rate between 3 ml/second and 9 ml/second (e.g. approximately 6 ml/sec via one or more delivery catheters 50), to purge non-transparent material.

In these flushing procedures, injectate 305 can comprise a transparent fluid selected from the group consisting of: saline; contrast; Dextran; and combinations of one or more of these. In some embodiments, the volume of injectate 305 delivered and/or the time of injectate 305 delivery during a flushing procedure is determined by a parameter selected from the group consisting of: type of procedure being performed; diameter of vessel in which optical assembly 130 is positioned; length of pullback; duration of pullback; and combinations of one or more of these. In some embodiments, injectate 305 is delivered during a flushing procedure by a delivery catheter with an ID greater than 0.027" (e.g. a first delivery catheter 50 whose distal end 59 is more proximal than a second delivery catheter 50 inserted into the first delivery catheter 50). In some embodiments, injectate 305 is delivered via multiple lumens 52 in associated multiple delivery catheters 50 (e.g. in the space between two or more pairs of delivery catheters 50 arranged to slidingly receive each other in a sequential fashion).

In some embodiments, injectate comprises a first fluid delivered in a first portion of a flushing procedure (e.g. a fluid comprising saline and/or a fluid comprising no or minimal contrast), and a second fluid including contrast (e.g. a second fluid comprising saline and contrast), such as to limit the amount of contrast delivered to the patient during the flush procedure. In these embodiments, injector 300 can comprise two reservoirs (as described hereabove), such as a first reservoir for supplying the first fluid and a second reservoir for supplying the second fluid. When comprised of two reservoirs, injector 300 can be configured to deliver the fluids in each reservoir at different rates, such as to achieve different pressures and/or to provide flushing through different catheters with different IDs.

As described herein, optical assembly 130 can be rotated (e.g. via rotation of core 120) and retracted (e.g. via retraction of shaft 110 by retraction assembly 220) during collection of image data, such as a rotation combined with retraction to create a 3D image of the patient site PS. In some embodiments, optical assembly 130 is rotated at a rate between 40 rps and 1000 rps, such as a rate of approximately 250 rps. In some embodiments, optical assembly 130 is rotated at a first rate during an imaging mode, and a second rate during a preview mode (imaging mode and preview mode each described hereabove). In some embodiments, the retraction of optical assembly 130 spans of distance of between 1 cm and 15 cm, such as a retraction of approximately 4 cm. In some embodiments, optical assembly 130 is retracted at a rate of between 1 mm/sec and 60 mm/sec. In some embodiments, the retraction of optical assembly 130 comprises a retraction of approximately 7.5 cm over 4 seconds and/or a retraction rate of approximately 20 mm/sec. In some embodiments, retraction of optical assembly 130 comprises a resolution of between 5 µm and 20 µm axially and/or a resolution between 20 µm and 100 µm longitudinally. The longitudinal resolution is governed by two factors: the spot-size (light beam cross-section) at the tissue surface being imaged and the spacing between successive rotations of optical assembly 130 during retraction. For a rotation rate of 100 rps and a pullback rate of 22 mm/sec, a pitch of 200 µm between rotations results. In these configurations, a spot size between 20 µm and 40 µm would result in collecting image data which under-samples the objects being imaged. System 10 can be configured to more closely match spot size with pitch, such as by correlating spot size with rotation rate and/or pullback rate.

In some embodiments, imaging system 10 is constructed, arranged and used to create an image as described in applicant's co-pending U.S. Provisional Application Ser. No. 62/212,173, titled "Imaging System includes Imaging Probe and Delivery Devices", filed Aug. 31, 2015; the content of each of which is incorporated herein by reference in its entirety for all purposes.

In some embodiments, system 10 is configured to assist in the selection, placement and/or use of a treatment device 91. Treatment device 91 can comprise a stent retriever configured to remove thrombus or other occlusive matter from a patient, such as when imaging probe 100 images the anatomy and/or the treatment device 91 to produce anatomical information (e.g. used to select the size or other geometry of the stent retriever), visualize the stent retriever at the occlusive site (e.g. to position treatment device 91), and or visualize occlusive matter (e.g. thrombus) engaged with and/or not removed by the treatment device 91. In some embodiments, system 10 is configured to quantify a thrombus volume, such as a thrombus to be removed by a treatment device 91. Thrombus visualized by system 10 can comprise thrombus selected from the group consisting of: residual thrombus in acute stroke; thrombus remaining after a thrombus removal procedure; thrombus present after flow diverter implantation; and combinations thereof.

In some embodiments, system 10 is configured to provide anatomical information to be used to select a site of implantation and/or to select a particular implantable device to be implanted in the patient, such as implant 85 of system 10 described hereabove. System 10 can be configured to image at least one perforator artery of the patient, such as to image one, two or more perforator arteries of at least 50 µm in diameter. Implant 85 can be implanted in the patient via implant delivery device 80, such as when implant 85 comprises a stent and/or a flow diverter. System 10 can be configured to perform a function selected from the group consisting of: detect and/or quantify implant 85 apposition (e.g. a stent or flow diverter malapposition); provide quantitative and/or qualitative information regarding the size and/or placement of an implant 85 to be implanted in a patient, such as information related to perforator location; perforator geometry, neck size and/or flow diverter mesh density; and combinations of one or more of these. System 10 can be configured to provide information related to an implant 85 parameter selected from the group consisting of: porosity; length; diameter; and combinations thereof. System 10 can be configured to provide implant 85 porosity information comprising the porosity of one or more portions of implant 85, such as a portion to be positioned proximate a sidebranch of a vessel in which implant 85 is implanted. System 10 can be configured to provide porosity information based on a wire diameter of implant 85. System 10 can be configured to provide information related to the implantation (e.g. implantation site or device information) of a second implant 85 to be implanted in the patient. In these embodiments in which two implanted devices 85 are used, the first and second implanted devices can comprise similar or dissimilar devices (e.g. a stent and a flow diverter, two stents or two flow diverters). System 10 can be configured to collect image data during deployment of one or more implants 85. System 10 can be configured to collect image data used to modify an implanted device (e.g. during and/or after implantation), such as to modify the porosity of implant 85 (e.g. via a treatment device 91 comprising a balloon catheter used to adjust the porosity of a partially or fully implanted implant 85).

Imaging conventionally inaccessible areas of the body (e.g. coronary arteries, neurovascular arteries, the endocrine system, pulmonary airways, etc.) using specialized catheters has been in use for several decades. Even so, products for these applications are still being widely developed as technological advances allow higher resolution, new modalities (e.g. spatially-resolved spectroscopy), and lower cost probes to be realized. Limitations and other issues with the current catheters are described herebelow. Such imaging catheters commonly utilize high-speed rotation of distally-located optics to create a cross sectional view of a body lumen since reduced diameter imaging catheters generally precludes the use of conventional optics or so-called coherent fiber bundles. Rather than creating a multi-pixel conventional 'snapshot', the image with rotating optics is built up one or two pixels at a time by scanning a single imaging spot, similar to the raster scan employed by older CRT's. This rotation may be coupled with a longitudinal motion ('pullback') to create a spiral scan of the artery or lumen, which can be rendered as a 3-D image. The majority of currently available imaging catheters have a distally located imaging element, connected optically or electrically to a proximal end. The imaging element is attached to a mechanical transmission that provides rotation and pullback to occur. Recently, advances in micro-motor technology can supplant the mechanical transmission with distally located actuation, but pullback is still required. However, these motors are expensive and relatively large (available designs do not allow probes below 1 mm OD to be constructed).

There are a number of commercially available "torque shafts" which are miniature wire-wound tubes intended to transmit torque over a long and flexible shaft. Such devices are now commonly used in intravascular ultrasound (IVUS) procedures as well as OCT procedures. Imaging probes combined with torque shafts perform rotational scanning in coronary arteries for example. Generally however, these devices are approximately 0.8 to 1.3 mm in OD, (2.4 Fr to ~4 Fr) and are thus 2 to 4 times larger than the devices required by neurological applications. Presently, such torque wires are not scalable to the sizes required to permit the construction of scanning imaging catheters less than 0.7 mm in OD.

Since optical imaging in arteries necessitates the clearing of obfuscating blood, usually with a flush solution, the imaging catheter diameter becomes critically important in smaller or obstructed vessels (e.g. due to use of smaller guides). Since it is often diseased or obstructed vessels that require imaging for diagnosis and treatment, imaging probe 100 can be designed for a small diameter (e.g. an OD less than or equal to 0.025", 0.016" or 0.014").

As has been previously disclosed (Petersen, et al U.S. Pat. No. 6,891,984 [the '984 patent]; Crowley U.S. Pat. No. 6,165,127 [the '127 patent], the content of each of which is incorporated herein by reference in its entirety for all purposes), using a viscous fluid located at the distal region of the imaging catheter is provided to prevent twisting.

Achieving uniform rotational scanning at the distal tip of a single fiber imaging catheter, while maintaining an overall device size less than 500 µm in OD is a significant challenge. Because it is currently impractical to add a motor to the distal tip that is sized less than 1 mm in OD (see Tsung-Han Tsai, Benjamin Potsaid, Yuankai K. Tao, Vijaysekhar Jayaraman, James Jiang, Peter J. S. Heim, Martin F. Kraus, Chao Zhou, Joachim Hornegger, Hiroshi Mashimo, Alex E. Cable, and James G. Fujimoto; "Ultrahigh speed endoscopic optical coherence tomography using micro-motor imaging catheter and VCSEL technology", Biomed Opt Express. 2013 Jul. 1; 4(7): 1119-1132), with the attendant wires and size issues, a way must be found to apply torque to the proximal end and transmit the torque to the distal tip (which may be as much as three meters away in some clinical applications) while maintaining uniform rotational speed. Uniform speed is paramount to image fidelity as non-uniform rotation can lead to image smearing and severe distortions (See FIG. 3). If the extremely low inherent rotational stiffness of a glass fiber is considered, the issues of uniformly spinning the distal tip by driving the proximal end can be appreciated. Uniform rotation is critically important in endoscopic techniques in order to obtain accurate circumferential images. The term 'NURD' (non-uniform rotational distortion) has been coined in the industry to describe these deleterious effects.

Figure 3:
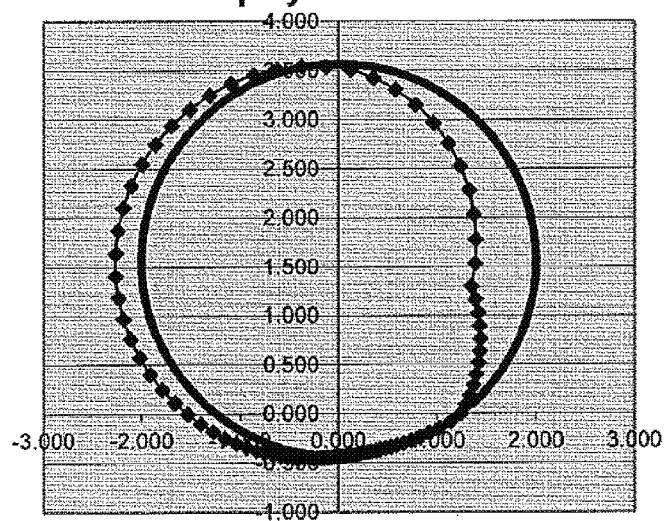
FIG. 3 is a chart illustrating non-uniform rotational distortion.

An example of distortion caused by non-uniform rotational distortion (NURD) is shown in FIG. 3. The solid curve is a simulated perfectly round artery, 4 mm in diameter. The curve with square data points is the image of the same arterial wall with NURD. In this case, the catheter rotation is slowed by 50% over a small portion of the cycle, and sped up by 50% in another portion, such that the average distal rotational speed matches the proximal rotational speed (as it must, otherwise rapidly accumulating twist would cause the core 120 to break). It can be seen that this NURD can lead to significant measurement errors. The imaging probe 100 and other components of system 10 are configured to reduce these types of distortions.

The '127 patent discloses the use of a viscous fluid located inside the bore of an ultrasound catheter. The purpose of the fluid is to provide loading of a torque wire such that the wire enters the regime of high torsional stiffness at moderate spin rates. As described in the '127 patent, this fluid is housed within a separate bore formed inside the main catheter, increasing the overall size of the device. The fluid does not contact the imaging tip, nor does the ultrasound energy propagate through this fluid. This approach also requires the use of a torque wire, limiting the achievable reduction in size needed. In the imaging probe of the present inventive concepts, one or more viscous fluids (e.g. one or more fluids 190) can be provided to deliberately cause twisting (i.e. winding) of core 120. The twisting can comprise dynamic twisting that changes with total (i.e. end-to-end) frictional load (torque) of probe 100, to result in a relatively constant rotational rate. Probe 100 can be configured such that the amount of twisting changes during a pullback of one or more portions of probe 100 (e.g. a pullback of core 120 and/or a pullback of core 120 and shaft 110).

The '984 patent utilizes a viscous fluid with a high index of refraction to simultaneously reduce refractive effects at the curved sheath boundary as well as provide viscous loading to allow an optical fiber to be the torque transmitter. This configuration allows a certain reduction in size. However, the '984 patent fails to describe or disclose a mechanism for confining the fluid at the distal tip within the geometry constraints; unavoidable migration of this fluid during transport and storage will cause unavoidable loss of performance. Similarly, the '984 patent fails to address issues that could arise during pullback of the internal fiber which will cause voids to form in the viscous fluid, these voids causing relatively large optical effects (so-called 'bubble-artifacts', see, for example, "Expert review document on methodology, terminology, and clinical applications of optical coherence tomography: physical principles, methodology of image acquisition, and clinical application for assessment of coronary arteries and atherosclerosis", Francisco Prati, et al, European heart Journal, Nov. 4, 2009). In some embodiments, probe 100 is configured to rotate core 120 in a single direction (i.e. unidirectional) during use. In some embodiments, probe 100 comprises a torque shaft within shaft 110 and frictionally engaged with core 120, such as torque shaft 110b described herebelow. Torque shaft 110b can extend from the proximal end of probe 100 to a location proximal to optical assembly 130, such as a torque shaft with a distal end that is located at least 5 cm from optical assembly 130, or a distal end that is located proximal to the most proximal location of shaft 110 that is positioned within the patient.

A liquid, gel or other fluid-filled (e.g. and sealed) imaging probe 100 has the advantage that it does not require purging (e.g. to remove air bubbles). The fluid 190a or 190b can be configured as a lubricant, reducing friction between core 120 and shaft 110. In embodiments in which core 120 is pulled back relative to shaft 110 to obtain an image, a void is created at the end of core 120 that can be filled with liquid, gel or other fluid (e.g. fluid 190).

It is difficult for fluid to "fill in" this region as it must be provided from the proximal end of shaft 110 and travel the length of the core 120. Bubbles are likely to form here as a low pressure can be generated. In embodiments of the present inventive concepts, rather than retracting the core 120 within shaft 110, the entire imaging probe 100 is pulled back during image data collection (i.e. core 120 and shaft 110 are retracted in unison without relative axial motion between the two). Since the shaft 110 moves along with the core 120, the presence of a low-pressure region at the end of the imaging core is eliminated or at least mitigated.

Figure 4:
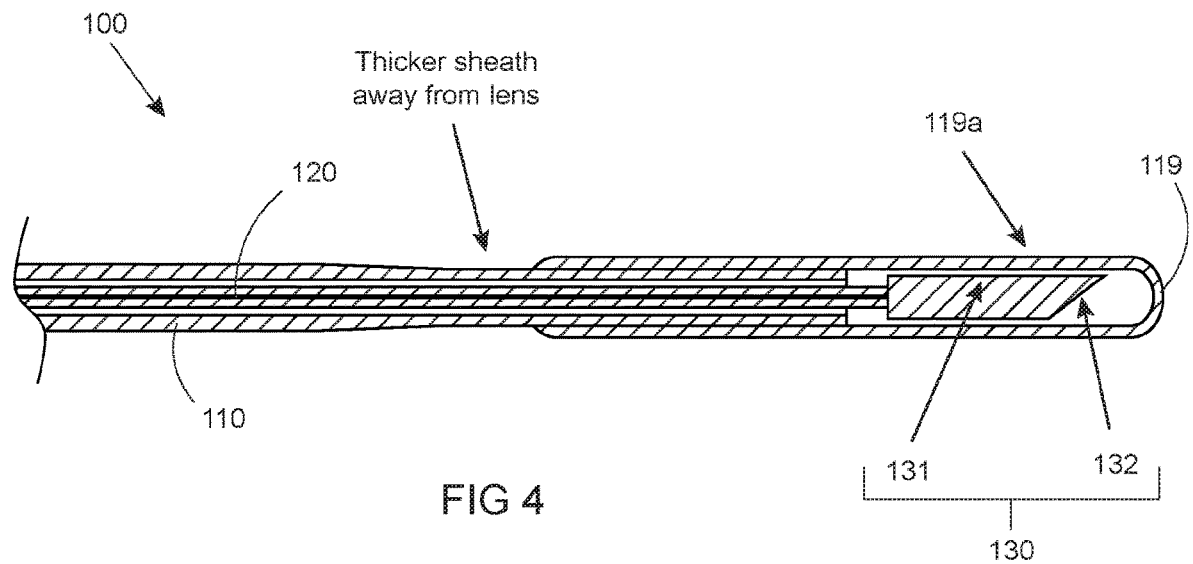
FIG. 4 is a side sectional view of the distal portion of an imaging probe comprising a thin walled segment of shaft about an optical assembly, consistent with the present inventive concepts.

As shown in FIG. 4, such "mutual" motion of shaft 110 and core 120 allows shaft 110 to have a larger diameter around optical assembly 130, as relative motion between optical assembly 130 and shaft 110 is avoided. A larger diameter optical assembly 130 (e.g. a larger diameter lens of optical assembly 130) provides collection of more light, which can correlate to a brighter image. This configuration can also provide a lens of optical assembly 130 that has a focal length that is positioned farther away from the OD (i.e. outer surface) of shaft 110 surrounding optical assembly 130, improving distal image quality. Alternatively or additionally, and also as shown in FIG. 4, optical assembly 130 can comprise an OD that is larger than an ID of at least a portion of shaft 110 proximal to optical assembly 130. In these embodiments, optical assembly 130 and shaft 110 can be retracted simultaneously during collection of image data from a target area.

In some embodiments, the shaft 110 wall is relatively thicker over a majority of its length as compared to a thinner wall of shaft 110 at a distal portion of shaft 110 (e.g. thinner at a shaft 110 portion proximate optical assembly 130). Such a configuration allows for improved longitudinal and torsional control for positioning of imaging probe 100. In some embodiments, shaft 110 can comprise a stiffened portion positioned about optical assembly 130, such as a stiffened segment of shaft 110 comprising: a different (stiffer) wall material; a braided shaft portion; and or a stiffening element (e.g. a wire embedded in the wall of shaft 110). The stiffened distal portion of shaft 110 can correlate to a thinner wall, which in turn correlates to optical assembly 130 comprising larger optical components (e.g. one or more larger diameter lenses), for example without having to increase the OD of shaft 110 surrounding optical assembly 130. In some embodiments, shaft 110 has varying mechanical properties along its length (e.g. a stiffened proximal segment for "push-ability"), and a gradually decreasing stiffness distally (e.g. to improve deliverability and safety as advanced into tortuous anatomy).

Figure 5:
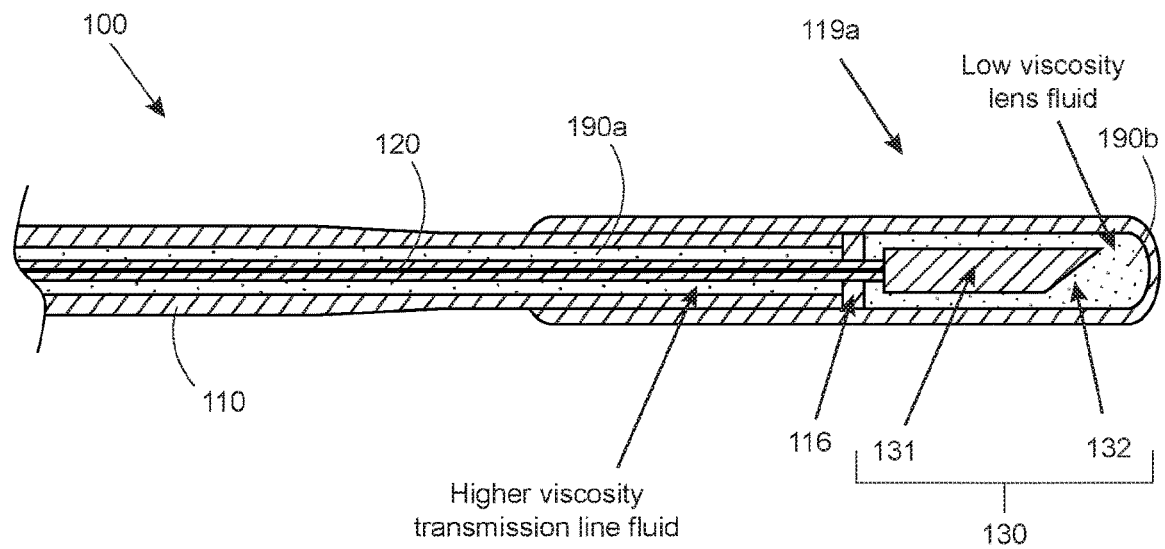
FIG. 5 is a side sectional view of the distal portion of an imaging probe comprising two fluids within the shaft of the imaging probe, consistent with the present inventive concepts.

Also as shown in FIG. 4, optical assembly 130 can comprise a lens 131 and a reflecting element 132 (e.g. to "turn" the light). Reflecting element 132 is configured such that optical assembly 130 is asymmetrical. When optical assembly 130 is spun at high speed, the presence of viscous liquids or other viscous fluids in the optical path surrounding optical assembly 130 could, in some cases, cause cavitation in the region behind reflector 132. As shown in FIG. 5, in some embodiments, probe 100 includes a first fluid, fluid 190a that surrounds core 120, and a second, different fluid, fluid 190b, that surround optical assembly 130, such that fluid 190a can be configured to provide a first function (e.g. prevent or at least reduce undesired rotational variances of core 120), while fluid 190b provides a second function (e.g. prevent or at least reduce cavitation about optical assembly 130). In some embodiments, the viscosity of fluid 190b can be selected to be relatively low viscosity, such as to minimize cavitation, while the viscosity of fluid 190a can be selected to be relatively high (e.g. at least more viscous than fluid 190b) to optimize uniformity in the rotational speed.

In neurological placement, imaging probe 100 is usually placed into a femoral vessel of the patient. There is significant tortuosity in the vasculature proximal to a neurological imaging area, starting with the carotid artery take off from the aorta. In some embodiments, the use of a high viscosity fluid 190a in the mid and/or proximal section of imaging probe 100 allows the fluid 190a to provide the additional function of lubricating the spinning core 120 in the shaft 110 (e.g. lubrication of benefit due to the high tortuosity in which imaging probe 100 is placed). The reduced friction that results reduces the stress on the core 120, and allows smoother motions over any discontinuities in shaft 110 or core 120. Fluid 190 can be configured to provide sufficient lubrication or other advantageous parameter to eliminate or at least reduce ("reduce" herein) adverse effects that would otherwise occur as probe 100 is positioned in tortuous anatomy (e.g. when distal portion 119a is positioned proximate and distal to the carotid artery). In these embodiments, fluid 190 can comprise a high viscosity fluid.

Additionally, the presence of a high viscosity fluid 190a helps maintain the lower viscosity fluid 190b in the distal end of shaft 110 prior to use, as the higher viscosity fluid 190a in shaft 110 operates as a barrier, and reduces the likelihood of fluid 190b migration from the imaging region about optical assembly 130 prior to use (e.g. during sterilization and shipping of imaging probe 100). In some embodiments, a sealing element, such as sealing element 116, is positioned between two or more different fluids 190. Alternatively, no separating element may be present, such as when one or more of the fluids 190 comprise a gel configured not to mix with a neighboring fluid 190.

Figure 6:
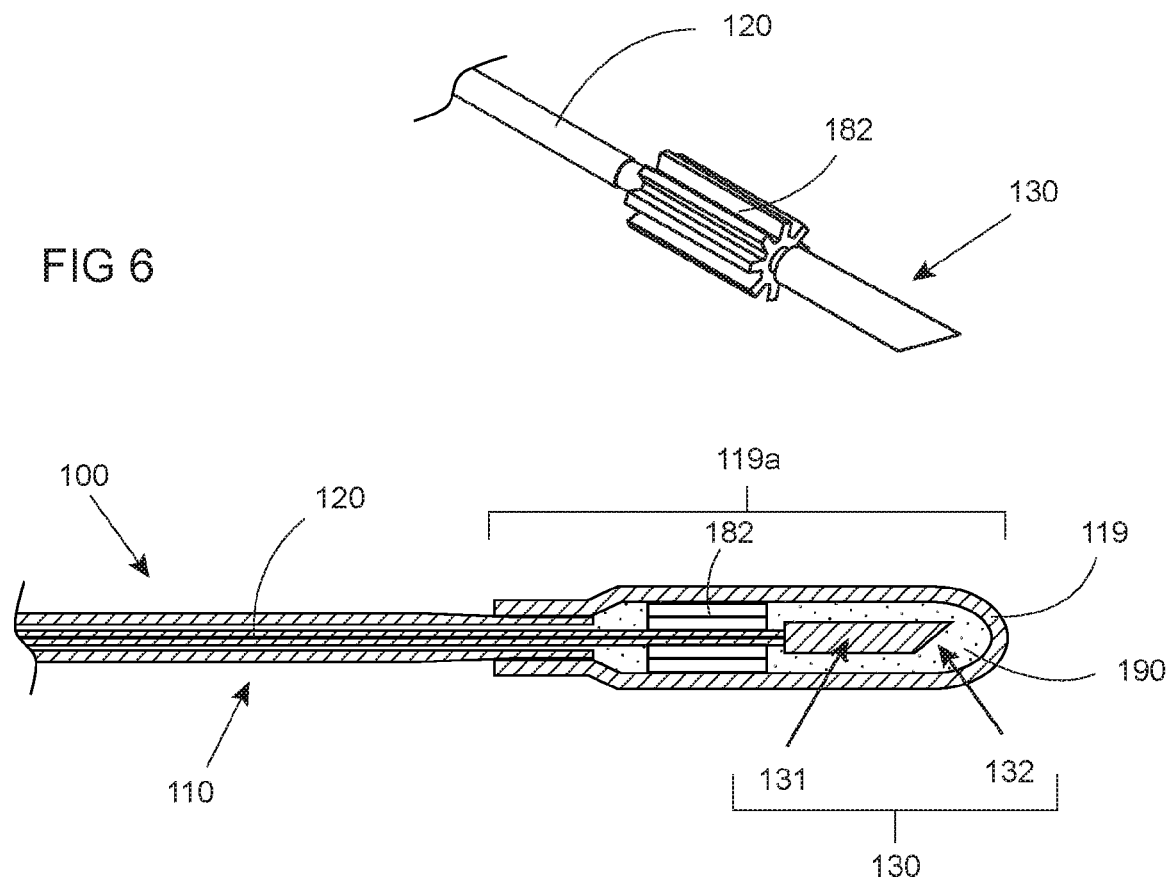
FIG. 6 is a perspective view of an impeller, and a side sectional view of a distal portion of an imaging probe comprising the impeller, consistent with the present inventive concepts.

In some embodiments, imaging probe 100 includes an inertial assembly comprising an impeller, propeller or other inertia-based element configured to reduce undesired variances in rotational speed of optical assembly 130, such as is shown in FIG. 6. Imaging probe 100 comprises impeller 182 that is attached to the core 120. Drag on impeller 182 "winds up" core 120 and decreases unintended or otherwise undesired variances in rotational velocity of the fiber. Impeller 182 operates to spin the fluid 190 between shaft 110 and optical assembly 130. The impeller 182 blades form drag, which due to its symmetry around its rotational axis, remains uniform through the rotation. In some embodiments, the radial extending ends of impeller 182 intentionally contact an inner wall of shaft 110, to alternatively or increasingly provide drag. Impeller 182 can comprise one or more projections from core 120, such as projections that frictionally engage shaft 110 and/or otherwise cause shear force that applies a load to core 120 during rotation. Impeller 182 can comprise one or more projections from shaft 110, such as projections that frictionally engage core 120 and/or otherwise cause shear force that applies a load to core 120 during rotation.

Impeller 182 can be configured to cause wind-up loading of core 120. Impeller 182 can be configured to frictionally engage fluid 190 and/or shaft 110 during rotation of core 120. Impeller 182 can comprise a component selected from the group consisting of: turbine; vane-type micro-structure; flywheel; and combinations of one or more of these.

Liquid, gel or other fluid positioned inside shaft 110 can have a tendency to form bubbles. If these bubbles are in the optical path they will reduce the light transmission. In some embodiments, fluid 190a and/or fluid 190b (singly or collectively fluid 190) can be pressurized (e.g. to a pressure of 100 psi or above) to prevent or at least reduce the size of any bubbles in shaft 110, such as is described herein in reference to FIG. 7.

Small tire inflators are commonly used for filling bicycle tires. They are available in sizes smaller than 1 inch, which is suitable for this application. These and similarly configured inflators can provide pressures up to and beyond 100 psi, which when applied to fluid 190 can significantly reduce the bubble size. Assuming a bubble size at atmospheric pressure is to be 0.1 microliters, the bubble size at 100 psi can be calculated as:

$$V_p = V_a P_a / P_p$$

where:
$V_p$=Bubble volume under pressure
$V_a$=Bubble volume at atmospheric pressure (e.g. 0.1 µL)
$P_a$=Atmospheric pressure (14.7 PSI)
$P_p$=Pressurizing device pressure (e.g. 100 psi)

Under pressurization, the bubble volume decreases from 0.1 µL to 0.0147 µL. The corresponding bubble diameter is reduced from 0.022" to 0.011", which will mitigate or eliminate deleterious effects on the optical beam.

FIG. 7 is a sectional view of an imaging probe including a pressurization system, consistent with the present inventive concepts. Imaging probe 100 comprises shaft 110 with proximal end 111, lumen 112, core 120 and optical connector 102, each of which can be of similar construction and arrangement as those described hereabove in reference to FIG. 1. Imaging probe 100 can include pressurization assembly 183 (e.g. a pressurized gas canister) which can be fluidly connected to lumen 112 via valve 184 (e.g. a one way check valve). In some embodiments, each imaging probe 100 is provided with a pressurization assembly 183. Alternatively, a single pressurization assembly 183 can be reused (e.g. used on multiple imaging probes 100 in multiple clinical procedures). In some embodiments, pressurization assembly 183 can be pre-attached to shaft 110, or separated and attachable. In some embodiments, pressurization assembly 183 can be operably attached and/or activated just prior to the time of clinical use of imaging probe 100, such as to pressurize fluid within lumen 112 or other imaging probe 100 internal location, such as to reduce the size of one or more gas bubbles in a fluid, such as fluid 190 described herein.

In some embodiments, at a location near to proximal end 111 of shaft 110, sealing element 151 (e.g. a compressible O-ring) is positioned between core 120 and shaft 110. Shaft 110 and sealing element 151 can be constructed and arranged to maintain a relative seal as lumen 112 is pressurized (e.g. as described above), while allowing core 120 to rotate within shaft 110 and sealing element 151. Sealing element 151 can provide a seal during rotation of core 120 within shaft 110. Retraction of shaft 110 and core 120 simultaneously during imaging, as described herein, simplifies the design of sealing element 151. In some alternative embodiments, core 120 is retracted within shaft 110, and sealing element 151 is configured to maintain a seal during that retraction.

Figure 15A:
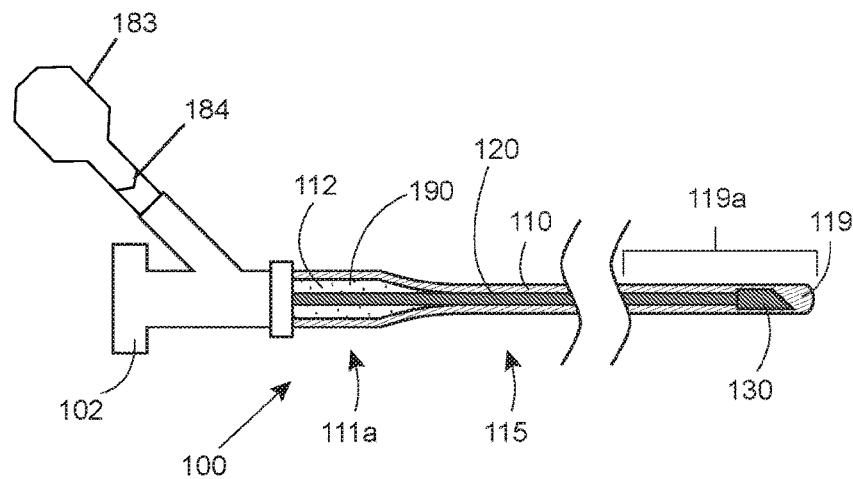
FIG. 15A-C are side sectional views of an imaging probe in a series of expansion steps of its shaft via an internal fluid, consistent with the present inventive concepts.
Figure 15B:
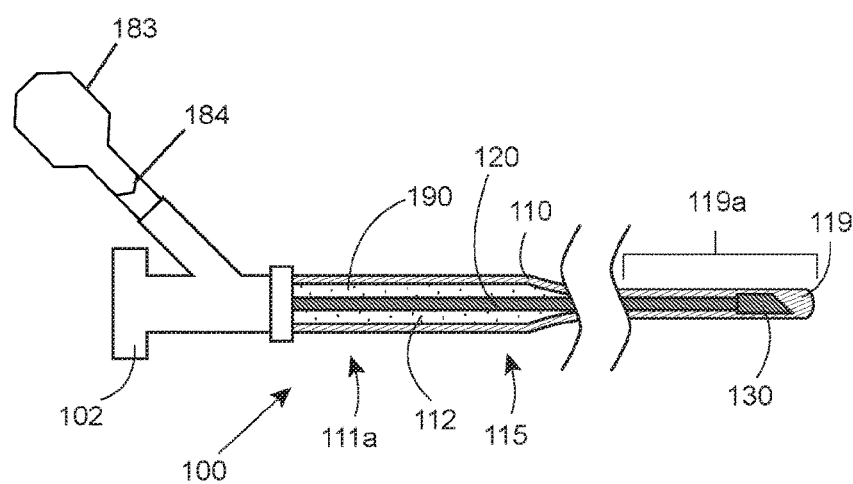
Figure 15C:
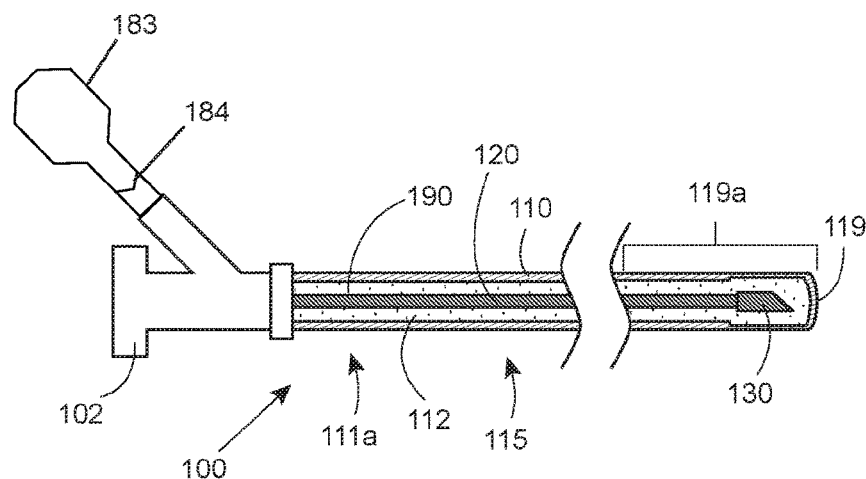

In some embodiments, at least a portion of shaft 110 is configured to radially expand as fluid 190 is pressurized, such as is shown in FIGS. 15A-C. Pressurization assembly 183 is attached to connector 102 such that fluid 190 can be introduced and/or pressurized into and/or within shaft 110. In FIG. 15A, proximal portion 111a of shaft 110 is expanded (e.g. lumen 112 is expanded in the region of proximal portion 111a). In FIG. 15B, proximal portion 111a and mid portion 115 of shaft 110 are expanded. In FIG. 15C, proximal portion 111a, mid portion 115 and distal portion 119a are expanded. In these embodiments, system 10 can be configured to rotate core 120 after shaft 110 has been fully expanded as shown in FIG. 15C. Expansion of shaft 110 can create and/or increase space between core 120 and the inner wall of shaft 110. In some embodiments, shaft 110 remains at least partially expanded (e.g. shaft 110 has been plastically deformed) when the pressure of fluid 190 is decreased (e.g. to atmospheric pressure). Shaft 110 can be configured to expand to a first diameter (ID and/or OD) when fluid 190 is pressurized to a first pressure, and to expand to a second, larger diameter, when fluid 190 is pressurized to a second, higher pressure. In some embodiments, shaft 110 is configured to become more rigid as the pressure of fluid 190 increases.

There can be two attachments from probe 100 (e.g. a disposable catheter) to the non-disposable components of system 10. One is attached to shaft 110 (a non-rotating shaft) and the other to core 120. Attachment of imaging probe 100 to console 200 can comprise two functional attachments. One attachment comprises attachment of shaft 110 to a retraction assembly, such as retraction assembly 220 described herein, such that shaft 110 (and optic assembly 130) can be retracted during collection of image data. Another attachment comprises attaching core 120 to a rotational assembly, such as rotation assembly 210, such that core 120 can be rotated during collection of image data. Both attachments can be retracted together during collection of image data. The attachment of core 120 makes the optical connection between core 120 and an imaging assembly (e.g. imaging assembly 230 described herein) and can provide the motive power to rotate core 120 (e.g. an attachment to rotation assembly 210).

The imaging system and associated imaging probes of the present inventive concepts provide enhanced compatibility with traditional therapeutic catheters, such as those used in neurological procedures as described herein.

Stent retrieval devices (also referred to as "stent retrievers") are used for endovascular recanalization. While the rate of successful revascularization is high, multiple passes of the stent retrieval device are often required to fully remove the clot, adding to procedure times and increasing likelihood of complications. The addition of imaging to a stent retrieval procedure has the potential to reduce both procedure time and complications. In FIGS. 8-11, system 10 comprises imaging probe 100 and a therapeutic device, treatment device 91. While treatment device 91 is shown as a stent retriever, other therapeutic devices would be applicable, such as a treatment device 91 selected from the group consisting of: stent retriever; embolization coil; embolization coil delivery catheter; stent; covered stent; stent delivery device; aneurysm treatment implant; aneurysm treatment implant delivery device; flow diverter; balloon catheter; and combinations thereof. Imaging probe 100 and treatment device 91 have been placed into a vessel, such as a blood vessel of the neck or head. Imaging probe 100 and treatment device 91 can be insertable into a single catheter, such as delivery catheter 50d shown.

Positioning of optical assembly 130 and resulting images produced assure correct placement of the treatment device 91 (e.g. positioning of the stent retriever distal to the thrombus) and also assures that therapy is completed successfully (e.g. sufficient thrombus has been removed), which can both reduce procedure times and improve clinical results.

In some embodiments, system 10 comprises delivery catheter 50a (not shown, but such as a 6-8 Fr guide catheter) that can be placed into a target vessel (e.g. artery), such as by using transfemoral access. In some embodiments, delivery catheter 50a comprises a standard balloon guide catheter, such as to prevent distal thrombus migration and to enhance aspiration during thrombectomy. System 10 can further comprise delivery catheter 50b (not shown but such as a flexible 5-6 Fr catheter) that is used as an intermediate catheter, advanced through delivery catheter 50a to gain distal access close to the occluded segment of the vessel. System 10 can comprise a third delivery catheter 50c, shown, such as a 0.021" to 0.027" microcatheter used to cross the thrombus or otherwise provide access to a target site to be treated and/or imaged. Angiographic runs can be performed through the delivery catheter 50c to angiographically assess the proper position of the delivery catheter 50c tip (e.g. position of tip distal to the thrombus and to estimate the length of the clot). The treatment device 91 (e.g. the stent retriever shown) is subsequently released by pulling back delivery catheter 50c while holding the treatment device 91 in place. In some embodiments, the treatment device 91 should cover the entire length of an occlusion in order to achieve flow restoration (e.g. when the stent portion opens).

In FIG. 8, a distal portion of delivery catheter 50c has been positioned in a blood vessel (e.g. within a vessel location including thrombus). A stent portion of treatment device 91 remains undeployed, captured within the distal portion of delivery catheter 50c. In FIG. 9, delivery catheter 50c is retracted, such that the stent portion of treatment device 91 deploys (e.g. to engage thrombus, thrombus not shown). In FIG. 10, imaging probe 100 is advanced through the deployed stent portion of treatment device 91. Image data can be collected during the advancement. In FIG. 11, imaging probe 100 is being retracted (optical assembly 130 passes through the stent portion of treatment device 91) as image data is collected, such as to perform a procedural assessment as described herein.

In some embodiments, system 10 is constructed and arranged such that proximally applied torque (e.g. to core 120) and distally applied rotational speed control (e.g. to core 120 and/or optical assembly 130) is provided. This configuration has several benefits, including but not limited to: small size; low-cost; and an independence from the tortuous path proximal to the distal tip of imaging probe 100.

In some embodiments, system 10 is configured to provide precise rotational control (e.g. avoid undesired rotational speed variances of core 120 and/or optical assembly 130) via inertial damping, such as inertial damping which increases with rotational speed. This control can be accomplished with: a viscous fluid in contact with core 120 and/or optical assembly 130 (e.g. fluid 190a and/or 190b described herein); a fluid in contact with a mechanical load such a vane-type micro-structure; a mechanical load acting as a flywheel; and combinations thereof.

In some embodiments, imaging probe 100 comprises a guidewire independent design, comprising a shaft 110 with an OD of 0.016" or less (e.g. approximately 0.014"), and configured such that its shaft 110, core 120 and optical assembly 130 are retracted in unison using external pullback (e.g. retraction assembly 220 described herein).

In some embodiments, imaging probe 100 is configured to be advanced through vessels to a target site with or without the use of a microcatheter.

In some embodiments, imaging probe 100 is configured such that core 120 and optical assembly 130 are configured to be retracted within shaft 110 during image data collection, such as an internal pullback using purge media (e.g. fluid 190 or other purge media introduced between the core 120 and the shaft 110). In some embodiments, the introduced material is configured to provide a function selected from the group consisting of: index matching; lubrication; purging of bubbles; and combinations thereof.

In some embodiments, imaging probe 100 comprises an Rx tip. In these embodiments, imaging probe 100 can be configured such that core 120 and optical assembly 130 are configured to be retracted within shaft 110 during image data collection.

Figure 2:
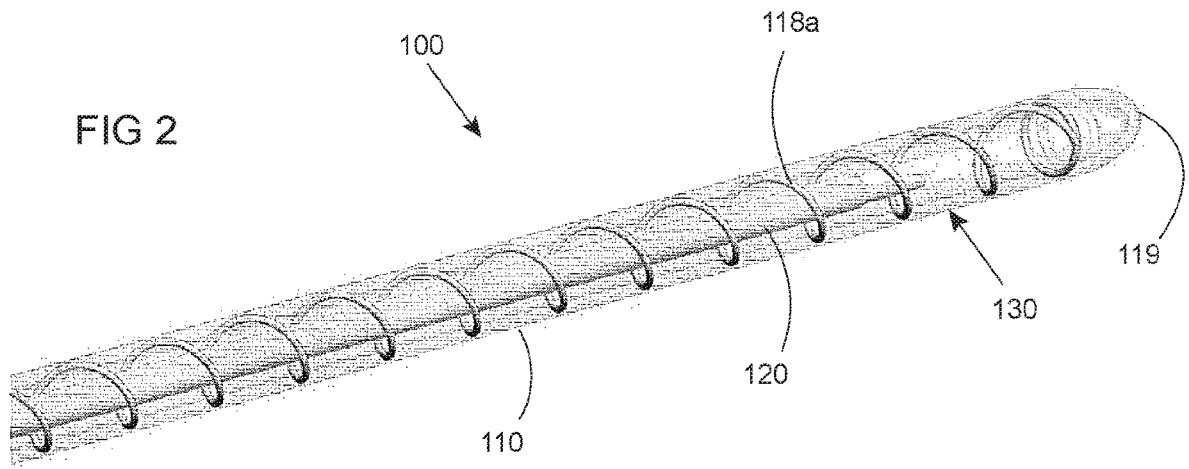
FIG. 2 is a perspective view of an imaging probe comprising a metal coil in a distal portion of its shaft, consistent with the present inventive concepts.

In some embodiments, imaging probe 100 comprises a highly deliverable, very small cross-section probe. In some embodiments, shaft 110 comprises one or more optically transparent materials providing an optically transparent window, viewing portion 117, positioned within distal portion 119a of shaft 110. Viewing portion 117 can comprise a length between 1 mm and 100 mm, such as a length of approximately 3 mm. In some embodiments, viewing portion 117 can comprise a length less than 50 mm, such as less than 20 mm or less than 15 mm (e.g. a relatively short window in embodiments in which both shaft 110 and optical assembly 130 are retracted simultaneously during the collection of image data). Viewing portion 117 can comprise a material selected from the group consisting of: nylon; nylon 12; nylon 66; and combinations of one or more of these. In some embodiments, at least a portion of shaft 110 comprises a reinforced portion, such as a reinforced portion comprising a stiffening element (e.g. stiffening element 118 shown in FIG. 1). In some embodiments, stiffening element 118 terminates proximal to optical assembly 130 (e.g. proximal to viewing portion 117 of shaft 110). Alternatively, stiffening element 118 can extend beyond optical assembly 130, such as is shown in FIG. 2, and the pullback geometry can be coordinated such that the light path to and from optical assembly 130 avoids the stiffening element 118. Stiffening element 118 can be included to resist twisting of distal portion 119a, such as during rotation of the core 120. For example, stiffening element 118 can comprise an element selected from the group consisting of: a coil; a metal coil; a metal coil wound over a plastic such as PTFE; a tube; a metal tube; a metal and/or plastic braid positioned within the wall of shaft 110; and combinations thereof. In some embodiments, shaft 110 comprises a stiffening element 118 comprising a coil wound in a direction such that rotation of the core 120 tends to cause the coil to tighten (e.g. to further resist twisting of shaft 110). In some embodiments, one or more portions of stiffening element 118 come into contact with a fluid maintained within shaft 110 (e.g. fluid 190 described herein), such that twisting of shaft 110 is reduced by torque forces applied by the fluid to stiffening element 118.

In some embodiments, system 10 includes integration of imaging probe 100 with one or more therapeutic devices (e.g. one or more treatment devices 91). For example, a treatment device 91 can comprise a stent retriever, and system 10 can provide real time simultaneous visualization of one or more of: the patient's anatomy (e.g. blood vessel wall and other tissue of the patient); the treatment device 91 (e.g. one or more struts of treatment device 91); and/or thrombus or other occlusive matter. The simultaneous visualization can be correlated to reduced procedure time and improved efficacy.

In some embodiments, system 10 is configured to apply proximal pressure to imaging probe 100, such as to keep the distal portion bubble-free or at least to mitigate bubble generation within one or more fluids 190 of imaging probe 100.

As described herein, imaging probe 100 can comprise a core 120 including a thin fiber that can be optically coupled on its distal end to optical assembly 130 comprising a lens assembly. In some embodiments, a fluid interacting element (e.g. a coil or length of wound wire, though not necessarily a torque wire), can be positioned just proximal to optical assembly 130 (e.g. embedded in the wall of or within shaft 110). In some embodiments, the shaft 110 can be filled with a low viscosity fluid 190, such as to interact with the fluid interacting element and create drag. The coil or other fluid interacting element, in contrast to a conventional torque wire, is not wound to create a high-fidelity transmission of torque but to increase viscous drag. The fluid 190 can be low viscosity (e.g. with a viscosity at or below 1000 Cp) to allow for easier filling and will reduce bubble artifacts created in high viscosity solutions. The fluid interacting element can comprise an impeller, such as impeller 182 described herein. The fluid interacting element comprises a non-circular cross section portion of a portion of shaft 110, such as a cross section with a geometry selected from the group consisting of: polygon shaped cross section of a lumen of shaft 110; projections into a lumen of shaft 110; recesses in inner diameter (i.e. the inner wall) of shaft 110; and combinations of one or more of these.

In some embodiments, imaging probe 100 comprises a formed element to create viscous drag, such as impeller 182 described herein. This element can have a variety of shapes designed to maximize the interaction with an internal fluid 190.

In some embodiments, imaging probe 100 is constructed and arranged such that viscous drag is created by mechanical friction between a part rigidly coupled to core 120 and in close contact with the wall of shaft 110. The friction may be created by the shear force of a narrow annulus between the mechanical element and the shaft 110 wall, such as when the shaft 110 is filled with fluid 190.

Figure 17:
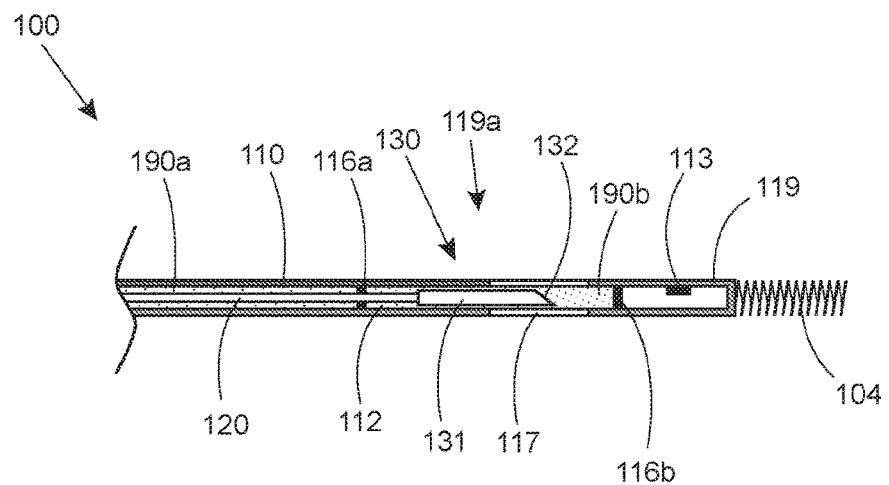
FIG. 17 is a side sectional view of the distal portion of an imaging probe comprising two sealing elements, consistent with the present inventive concepts.

In some embodiments, imaging probe 100 comprises at least one fluid 190 that is contained by at least one sealing element (e.g. sealing element 116 and/or sealing element 151 described herein). Sealing element 116 and/or 151 can be constructed and arranged to allow core 120 to rotate in the sealed region while preventing the (viscous) fluid 190 to penetrate through the seal. In some embodiments, two sealing elements 116*a* and 116*b* are included, such as one positioned just proximal to the optical assembly 130 and one positioned further distal, such as is shown in FIG. 17. In these embodiments, the separation distance between the two sealing elements 116 and/or the viscosity of the captured fluid 190 can be chosen to create sufficient torsional loading as core 120 is rotated. In some embodiments, the two sealing elements 116*a* and 116*b* are positioned apart at a distance between 1 mm and 20 mm. In some embodiments, the fluid 190 comprises a viscosity between 10 Cp and 100 Cp.

In some embodiments, system 10 comprises an imaging probe 100 and a console 200. Imaging probe 100 comprises: a proximal end 111 and a distal end 119, and at least one lumen 112 extending between the proximal end 111 and the distal end 119. Core 120 is positioned within lumen 112, the proximal end of core 120 in optical and mechanical communication with console 200, and the distal end of core 120 in optical communication with an optical assembly configured to collect image data within a body lumen.

In some embodiments, imaging probe 100 comprises optical assembly 130 located at the distal end of core 120, optical assembly 130 in mechanical and optical communication with core 120, the optical assembly 130 directing light to the target (e.g. thrombus, vessel wall, tissue and/or implant) being imaged and collecting return light from the imaged target. Imaging probe 100 can further comprise an inertial system (e.g. impeller 182) located proximate the distal end of the core 120, wherein the inertial system reduces undesired rotational speed variances that occur during a rotation of the core 120. The inertial system can comprise a (predetermined) length of wound hollow core cable, the distal end of the cable being affixed to core 120 just proximal to optical assembly 130, the proximal end unattached (e.g. not attached to core 120). The inertial system can comprise a mechanical resistance element located in the distal region of core 120, and can be in contact with a fluid 190 confined within a lumen 112 of shaft 110, the mechanical resistance arising during rotation within the fluid 190.

In some embodiments, imaging probe 100 comprises a sealing element, such as sealing element 151 described herein, located within lumen 112 of shaft 110. Sealing element 151 can be configured to allow rotation of core 120 while forming substantially liquid-tight seals around core 120 and the inner wall of shaft 110. In some embodiments, sealing element 151 is further configured as a mechanical resistance element. In some embodiments, sealing element 151 is formed from a hydrogel. In some embodiments, the sealing element 151 is formed by an adhesive (e.g. a UV-cured adhesive), bonding to the inner wall of shaft 110, but not the surface of core 120. In some embodiments, the surface of core 120 is configured to avoid bonding to an adhesive (e.g. a UV adhesive). In some embodiments, the sealing element 151 is formed from a compliant material such as a silicone rubber.

In some embodiments, an imaging system comprises an imaging probe 100 and an imaging console, console 200. The imaging probe 100 comprises: a proximal end 111, a distal end 119, and at least one lumen 112 extending between the proximal end 111 and distal end 119. The imaging probe further comprises: a core 120 contained within a lumen 112 of the shaft 110, the proximal end of core 120 in optical and mechanical communication with console 200, the distal end optically connected to an optical assembly 130 configured to collect image data within a body lumen. Optical assembly 130 is positioned at the distal end of the core 120, and is configured to direct light to the target (e.g. thrombus, vessel well, tissue and/or implant) being imaged and collecting return light from the imaged target.

In some embodiments, imaging probe 100 comprises a core 120 and one, two or more inertial elements, such as impeller 182 described herein, attached to optical assembly 130 and/or core 120 (e.g. attached to a distal portion of core 120). Impeller 182 can be configured such that when the core 120 is retracted (e.g. in the presence of liquid, gel or gaseous medium, such as fluid 190), the impeller 182 imparts a rotational force to core 120, such as to reduce undesired rotational speed variances. Impeller 182 can comprise a turbine-like construction.

In some embodiments, system 10 comprises an imaging probe 100 and an imaging console, console 200. Imaging probe 100 comprises a proximal end 111, a distal end 119, and at least one lumen 112 extending between proximal end 111 and distal end 119. Imaging probe 100 can further comprise a rotatable optical core, core 120 contained within a lumen 112 of shaft 110, the proximal end of core 120 in optical and mechanical communication with console 200, and the distal end configured to collect image data from a body lumen.

As described herein, imaging probe 100 comprises optical assembly 130 which is positioned at the distal end of core 120. Optical assembly 130 is in mechanical and optical communication with core 120, and is configured to direct light to tissue target being imaged and collect return light from the imaged target. Imaging probe 100 can further comprise a reinforcing or other stiffening element (e.g. stiffening element 118 described herein) embedded into shaft 110 that creates an improved stiffness but effectively optically transparent window for rotational and pullback scanning. Stiffening element 118 can comprise an embedded wire and/or a stiffening member (e.g. a plastic stiffening member) in shaft 110. Stiffening element 118 can comprise a spiral geometry. As described hereabove, the spiral geometry of stiffening element 118 and a pullback spiral rotational pattern of optical assembly 130 can be matched but offset by approximately one-half of the spiral of stiffening element 118, such that an imaging beam of optical assembly 130 passes between the stiffening 118 spirals during pullback of optical assembly 130.

Figure 12:
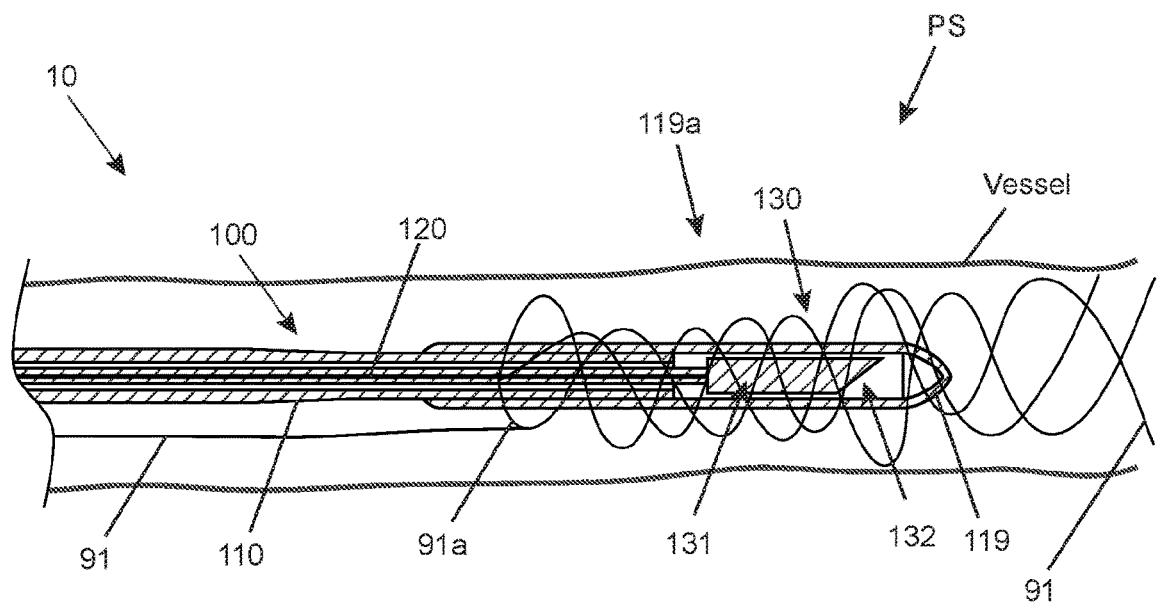
FIG. 12 is a side sectional anatomical view of a system comprising an imaging probe and a treatment device, consistent with the present inventive concepts.

Referring now to FIG. 12, a side sectional view of the distal portion of probe 100 is illustrated, having been inserted into a vessel, such that optical assembly 130 is positioned within treatment device 91 (e.g. a stent deployment device, stent retriever or other treatment device), consistent with the present inventive concepts. Probe 100 comprises shaft 110, core 120, optical assembly 130, lens 131 and reflector 132, and those and other components of probe 100 can be of similar construction and arrangement to those described hereabove. In some embodiments, distal end 119 comprises a geometry and/or a stiffness to enhance advancement of distal end 119 through blood vessels and/or one or more devices positioned within a blood vessel. For example, distal end 119 can comprise the bullet-shaped profile shown in FIG. 12. Alternatively or additionally, treatment device 91 can comprise a proximal portion (e.g. proximal end 91a shown), which can be configured to enhance delivery of distal end 119 through proximal end 91a. In some embodiments, probe 100 comprises a spring tip, such as spring tip 104 described hereabove.

Probe 100 and other components of system 10 can be configured to allow a clinician or other operator to "view" (e.g. in real time) the collection of thrombus or other occlusive matter into treatment device 91, such as to determine when to remove treatment device 91 and/or how to manipulate treatment device 91 (e.g. a manipulation to remove treatment device 91 and/or reposition treatment device 91 to enhance the treatment). The ability to view the treatment can avoid unnecessary wait time and other delays, as well as improve efficacy of the procedure (e.g. enhance removal of thrombus).

Figure 13:
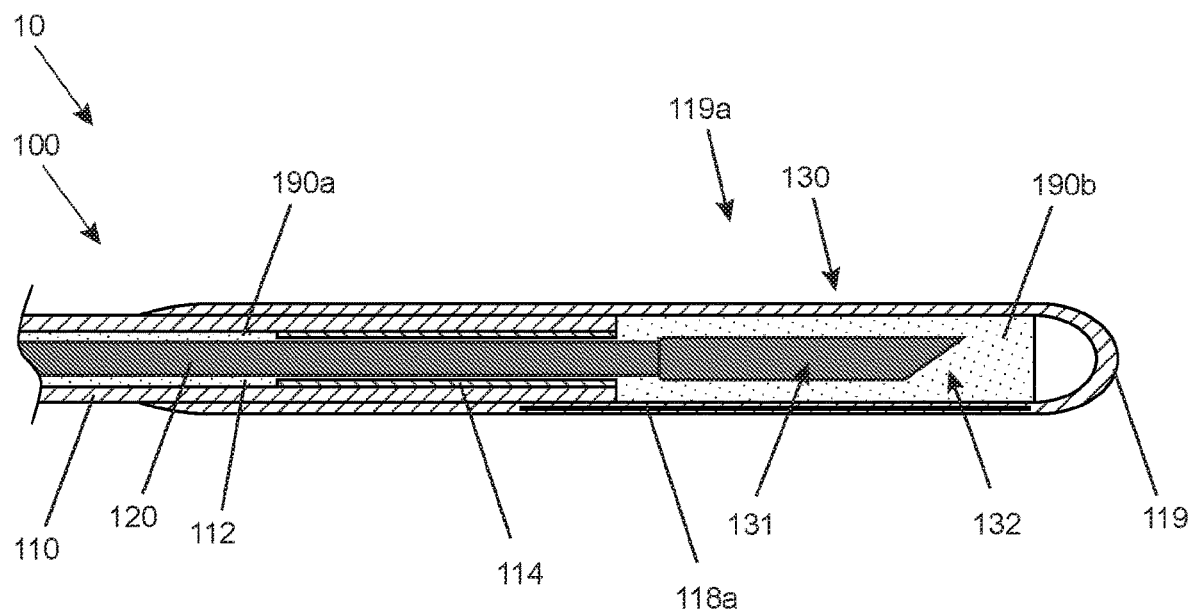
FIG. 13 is a side sectional view of an imaging probe comprising precision spacing between a rotatable optical core and a shaft, the spacing configured to provide capillary action to a fluid, consistent with the present inventive concepts.

Referring now to FIG. 13, a side sectional view of the distal portion of probe 100 is illustrated, consistent with the present inventive concepts. Probe 100 comprises shaft 110, lumen 112, core 120, optical assembly 130, lens 131 and reflector 132, and those and other components of probe 100 can be of similar construction and arrangement to those described hereabove. In some embodiments, distal portion 119a of shaft 110 comprises a reinforcing element, stiffening element 118a as shown in FIG. 13. Inclusion of stiffening element 118a can allow the wall of shaft 110 surrounding optical assembly 130 to be thin (e.g. thinner than the wall in a more proximal portion of shaft 110). Stiffening element 118a can comprise an optically transparent material as described herein. Stiffening element 118a can be configured to provide column and/or torsional strength to shaft 110. In some embodiments, probe 100 comprises a lumen narrowing structure, such as tube 114 shown positioned within lumen 112 of shaft 110. Tube 114 can be adhesively or at least frictionally engaged with the inner wall of shaft 110 or the outer surface of core 120. In some embodiments, tube 114 is simply a projection from the inner wall of shaft 110 (e.g. part of shaft 110). Tube 114 can be configured to provide a function selected from the group consisting of: increase torsional strength of shaft 110; increase column strength of shaft 110; provide a capillary action between fluid surrounding core 120 and/or optical assembly 130; and combinations thereof. In some embodiments, probe 100 comprises fluid 190a and/or fluid 190b shown, such as is described hereabove. Fluid 190a and fluid 190b can comprise similar or dissimilar fluids. In some embodiments, fluid 190a and/or fluid 190b comprise a low viscosity fluid as described hereabove. In some embodiments, fluid 190a and/or fluid 190b comprise a shear-thinning fluid as described hereabove.

Referring now to FIG. 14, a schematic of an imaging probe is illustrated, shown in a partially assembled state and consistent with the present inventive concepts. Probe 100 can comprise a first portion, comprising a connector 102a, outer shaft 110a and spring tip 104, constructed and arranged as shown in FIG. 14. Probe 100 can further comprise a second portion, connector 102b, torque shaft 110b, core 120 and optical assembly 130. Outer shaft 110a, spring tip 104, core 120 and optical assembly 130 and other components of probe 100 can be of similar construction and arrangement to those described hereabove. Connector 102b can be of similar construction and arrangement to connector 102 described hereabove, such as to optically connect probe 100 to console 200. Connector 102a can be configured to surround and mechanically engage connector 102b, such that connectors 102a and/or 102b mechanically connect to console 200.

Torque shaft 110b frictionally engages core 120 (e.g. via an adhesive), at least at a distal portion of torque shaft 110b. Torque shaft 110b can be attached to connector 102b via an adhesive or other mechanical engagement (e.g. via a metal tube, not shown, but such as a tube that is pressed into connector 102b). In some embodiments, a strain relief is provided at the end of torque shaft 110b, tube 121 shown. Tube 121 can be configured to reduce kinking and/or to increase the fixation between torque shaft 110b and core 120. Tube 121 and torque shaft 110b can have similar IDs and/or ODs.

During assembly, torque shaft 110b, optical assembly 130 and core 120 are positioned within shaft 110a. Connector 102a can be engaged with connector 102b to maintain relative positions of the two components.

Torque shaft 110b can comprise one or more plastic or metal materials, such as when torque shaft 110b comprises a braided torque shaft (e.g. a braid comprising at least stainless steel). Torque shaft 110b can comprise a length such that the distal end of torque shaft 110b terminates a minimum distance away from optical assembly 130, such as a length of approximately 49 cm. In some embodiments, torque shaft 110b comprises a length such that none or a small portion of torque shaft 110b enters the patient. In these embodiments, retraction assembly 220 can be positioned and engage shaft 110 at a location distal to the distal end of retraction assembly 220.

Referring now to FIGS. 15A-C, a series of side sectional views of an imaging probe in a series of expansion steps of its shaft via an internal fluid, consistent with the present inventive concepts. Probe 100 comprises connector 102, shaft 110, core 120 and optical assembly 130, and those and other components of probe 100 can be of similar construction and arrangement to those described hereabove. Shaft 110 comprises proximal portion 111a, mid portion 115 and distal portion 119a. Probe 100 further comprises pressurization assembly 183, which may include valve 184, each of which can be of similar construction and arrangement to the similar components described hereabove in reference to FIG. 7. Probe 100 can be configured such that as fluid is introduced into lumen 112, and/or the pressure of fluid within lumen 112 is increased, shaft 110 expands. For example, a first introduction of fluid 190 into lumen 112 and/or a first increase of pressure of fluid 190 in lumen 112 (e.g. via pressurization assembly 183) can be performed such that the proximal portion 111a of shaft 110 expands as shown in FIG. 15A. Subsequently, a second introduction of fluid 190 into lumen 112 and/or a second increase of pressure of fluid 190 in lumen 112 can be performed such that the mid portion 115 of shaft 110 expands as shown in FIG. 15B. Subsequently, a third introduction of fluid 190 into lumen 112 and/or a third increase of pressure of fluid 190 in lumen 112 can be performed such that the distal portion 119a of shaft 110 expands as shown in FIG. 15C. In some embodiments, shaft 110 is expanded to create a space between the inner wall of shaft 110 and core 120 and/or to create a space between the inner wall of shaft 110 and optical assembly 130.

Figure 16:
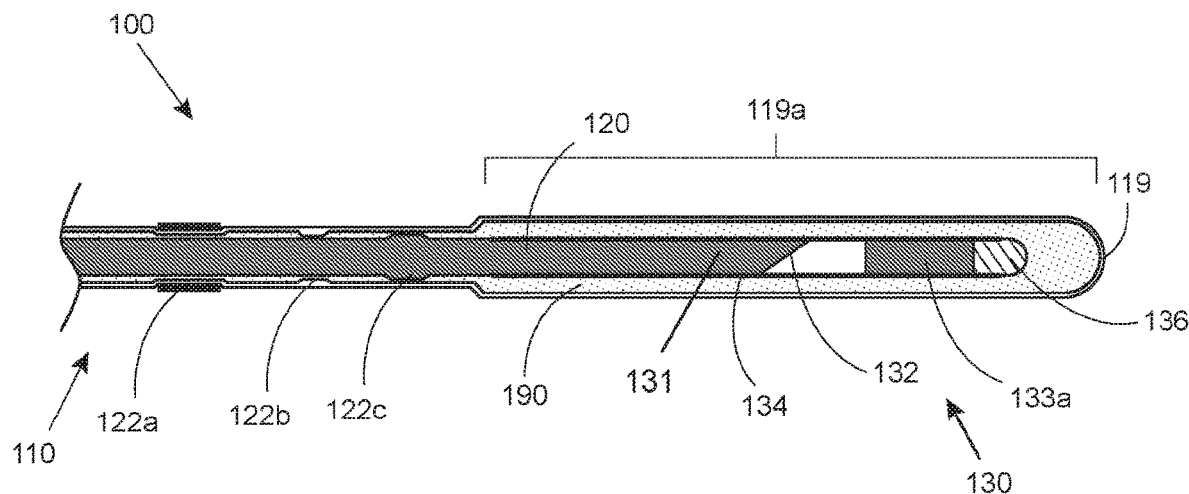
FIG. 16 is a side sectional view of the distal portion of an imaging probe comprising a distal marker positioned in reference to an optical assembly, consistent with the present inventive concepts.

Referring now to FIG. 16, a side sectional view of the distal portion of an imaging probe comprising a distal marker positioned in reference to an optical assembly is illustrated, consistent with the present inventive concepts. Probe 100 comprises shaft 110, core 120, optical assembly 130, lens 131 and reflector 132, and those and other components of probe 100 can be of similar construction and arrangement to those described hereabove. Shaft 110 comprises proximal portion 111a (not shown), distal portion 119a and distal end 119. Probe 100 can comprise a functional element 133a, which can be positioned on or relative to optical assembly 130 (e.g. positioned on or at a desired and/or known distance from optical assembly 130). Functional element 133a is shown positioned distal to optical assembly 130, and at a fixed distance as determined by a connecting element, tube 134 (e.g. heat shrink tubing or other plastic tube). In some embodiments, functional element 133a comprises a sensor, transducer or other functional element as described herein. In some embodiments, functional element 133a comprises a visualizable element, such as a radiopaque element, ultrasonically visible element and/or magnetically visible element. In some embodiments, functional element 133a comprises a visualizable element used to identify the location of optical assembly 130 on an image produced by an imaging device (e.g. a fluoroscope, ultrasonic imager or MRI) and the fixed location of functional element 133a relative to optical assembly 130 avoids registration issues, such as would be encountered if functional element 133a was positioned on shaft 110 or other component of probe 100 whose dimensions or other relative position to optical assembly 130 may change over time (e.g. due to expansion or contraction due to temperature shifts). In some embodiments, functional element 133a is attached to optical assembly 130 via a connecting element, such as tube 134 described hereabove, and tube 134 or other connecting element (e.g. connecting element 137 described herein) is configured to avoid dimensional changes (e.g. is minimally affected by changes in temperature). In some embodiments, probe 100 comprises fixation element 136 (e.g. an adhesive such as a UV cured adhesive) positioned just distal to functional element 133a as shown in FIG. 16, and configured to maintain the position of functional element 133a.

Probe 100 can comprise one or more elements that cause frictional engagement between shaft 110 and core 120 and/or simply reduce the space between shaft 110 and core 120, such as one or more of elements 122a, 122b and 122c shown in FIG. 16, such as to reduce undesired variations in rotational rate as described herein. In some embodiments, probe 100 comprises a compression element, band 122a, positioned about and/or within shaft 110 and causing a portion of the inner wall of shaft 110 to frictionally engage core 120. Alternatively or additionally, shaft 110 can comprise one or more projections 122b (e.g. annular projections) that extend to frictionally engage core 120. Alternatively or additionally, core 120 can comprise one or more projections 122c, each extending to frictionally engage shaft 110. One or more of each of elements 122a, 122b and/or 122c can be included, and each can be configured to create a shear force that applies a load to core 120 during rotation of core 120. In some embodiments, a fluid 190 is positioned between shaft 110 and core 120, such as a shear-thinning fluid as described herein. In these embodiments, one or more of elements 122a, 122b and/or 122c can comprise a space reducing element configured to increase the shear-thinning of the fluid 190 as core 120 is rotated (i.e. by interacting with the fluid 190 to increase the amount of thinning than that which would have occurred without the presence of the one or more space reducing elements 122).

Referring now to FIG. 17, a side sectional view of the distal portion of an imaging probe comprising two sealing elements is illustrated, consistent with the present inventive concepts. Probe 100 comprises shaft 110, core 120, optical assembly 130, lens 131, reflector 132 and viewing portion 117, and those and other components of probe 100 can be of similar construction and arrangement to those described hereabove. Shaft 110 comprises lumen 112, proximal portion 111a (not shown), distal portion 119a and distal end 119. Probe 100 can further comprise spring tip 104. Probe 100 can comprise functional element 113, as shown, or other functional elements as described herein. Probe 100 of FIG. 17 comprises two sealing elements, sealing element 116a (e.g. an O-ring surrounding core 120) and sealing element 116b (e.g. an elastomeric disk). In some embodiments, a fluid 190*b* is positioned within shaft 110 between sealing elements 116*a* and 116*b,* such as is described hereabove. Alternatively or additionally, a second fluid 190*a* is positioned within shaft 110 proximal to sealing element 116*a*. In some embodiment, a third fluid 190*c* (not shown), is positioned within shaft 110 distal to sealing element 116*b*. Fluids 190*a-c* can comprise similar or dissimilar fluids, also as described hereabove.

Referring now to FIG. 18, a side sectional view of the distal portion of an imaging probe comprising a reflecting element offset from a lens and multiple visualizable markers is illustrated, consistent with the present inventive concepts. Probe 100 comprises shaft 110, core 120, optical assembly 130, lens 131 and reflector 132, and those and other components of probe 100 can be of similar construction and arrangement to those described hereabove. Shaft 110 comprises lumen 112, proximal portion 111*a* (not shown), distal portion 119*a* and distal end 119.

In some embodiments, reflector 132 can be positioned distal to lens 131, and connected via connecting element 137, as shown in FIG. 18 and described hereabove.

In some embodiments, probe 100 comprises multiple visualizable markers, such as the four functional elements 123*a* shown in FIG. 18, which can be configured to provide a "ruler function" when visualized by a separate imaging device such as a fluoroscope, ultrasonic imager or MRI (e.g. when functional elements 123*a* comprise a radiopaque marker; an ultrasonically reflective marker or a magnetic marker, respectively). Functional elements 123*a* can comprise one or more visualizable bands (e.g. one or more compressible bands and/or wire coils) frictionally engaged with core 120. Alternatively or additionally, one or more functional elements 123*a* can be positioned on, within the wall of and/or on the inner surface of shaft 110. Functional elements 123*a* can be positioned equidistantly apart and/or at a known separation distance. In some embodiments, one or more functional elements 123*a* can be further configured as a sealing element (e.g. to provide a seal to a contained fluid such as one or more fluids 190 described herein) and/or as a rotational dampener configured to reduce undesired rotational velocity changes of core 120 and/or optical assembly 130.

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the inventive concepts, and variations of aspects of the inventive concepts that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. An imaging system for a patient comprising:
    an imaging probe comprising:
        an elongate shaft for insertion into the patient and comprising a proximal end, a distal portion, and a lumen extending between the proximal end and the distal portion;
        a rotatable optical core comprising a proximal end and a distal end, the rotatable optical core optically and mechanically connecting with a console;
        a probe connector positioned on the elongate shaft proximal end and surrounding at least a portion of the rotatable optical core;
        an optical assembly positioned in the elongate shaft distal portion and proximate the rotatable optical core distal end, the optical assembly configured to direct light to tissue and collect reflected light from the tissue, wherein the optical assembly comprises a single unitary gradient-index (GRIN) lens constructed and arranged to reflect light from a reflective surface of the single unitary GRIN lens;
        a shear-thinning fluid in the distal portion of the elongate shaft that has a viscosity that decreases with an increasing shear rate corresponding to a speed of rotation of the rotatable optical core; and
        a sealing element that separates the shear-thinning fluid in the distal portion from a fluid in the lumen of the elongate shaft.

2. The imaging system according to claim 1, wherein the shear-thinning fluid is configured to reduce undesired rotational variances of the rotatable optical core.

3. The imaging system according to claim 2, wherein the shear-thinning fluid is configured to avoid placing excessive loads on the rotatable optical core.

4. The imaging system according to claim 1, wherein the imaging probe is configured to access blood vessels of the brain.

5. The imaging system according to claim 1, wherein the imaging probe further comprises at least one space reducing element positioned between the elongate shaft and the rotatable optical core.

6. The imaging system according to claim 5, wherein the at least one space reducing element is configured to reduce rotational speed variances of the rotatable optical core.

7. The imaging system according to claim 6, wherein the at least one space reducing element is configured to reduce rotational speed variances of the speed of rotation of the rotatable optical core by increasing an amount of thinning of the shear-thinning fluid.

8. The imaging system according to claim 1, wherein the optical assembly comprises an outer diameter that is greater than an inner diameter of at least a portion of the elongate shaft proximal to the optical assembly.

9. The imaging system according to claim 1, wherein the imaging system includes a sensor that receives a signal related to the tissue, the console configured to process the signal, and a display configured to display a three-dimensional image from an output of the console in response to a retraction of the elongate shaft.

10. The imaging system according to claim 1, wherein the elongate shaft distal portion comprises an optically transparent window, and wherein the optical assembly is positioned within the optically transparent window.

11. The imaging system according to claim 10, wherein the optically transparent window comprises a length less than 20 mm.

12. The imaging system according to claim 11, wherein the optically transparent window comprises a length less than 15 mm.

13. The imaging system according to claim 10, wherein the optically transparent window comprises a material selected from the group consisting of: a Pebax® elastomer; a Pebax® 7233 elastomer; PEEK® plastic; amorphous PEEK® plastic; polyimide; glass; sapphire; nylon 12; nylon 66; and combinations thereof.

14. The imaging system according to claim 10, wherein the elongate shaft comprises at least a first portion, positioned proximate the optically transparent window, and wherein the first portion comprises a braided shaft.

15. The imaging system according to claim 10, wherein the elongate shaft further comprises a metal tube proximal to the optically transparent window.

16. The imaging system according to claim 1, further comprising a fluid interacting element in the distal portion and the lumen of the elongate shaft, wherein the fluid interacting element is configured to interact with the shear-thinning fluid to increase load on the rotatable optical core during rotation of the rotatable optical core.

17. The imaging system according to claim 1, wherein the rotatable optical core is constructed and arranged to rotate in a single direction.

18. The imaging system according to claim 1, wherein the optical assembly comprises an outer diameter between 80 μm and 500μm.

19. The imaging system according to claim 1, further comprising a retraction assembly constructed and arranged to retract the elongate shaft and the optical assembly while the imaging probe collects data from a target area.

20. The imaging system according to claim 1, wherein the imaging probe of the imaging system is configured to provide to the console quantitative or qualitative information used to determine the size of a flow diverter of an implant to be implanted in the patient or position a flow diverter in the patient.

21. The imaging system according to claim 20, wherein the quantitative and/or qualitative information comprises information related to a parameter selected from the group consisting of: perforator location; perforator geometry; neck size; flow diverter mesh density; and combinations thereof.

22. The imaging system according to claim 1, wherein the imaging probe of the imaging system is configured to provide implant site information, and wherein the implant site information is used to select a particular implantable device for implantation in the patient.

23. The imaging system according to claim 22, further comprising the implantable device for implantation in the patient, wherein the implantable device comprises a device selected from the group consisting of: stent; flow diverter; and combinations thereof.

24. The imaging system according to claim 23, wherein the imaging system provides information regarding an implantable device parameter selected from the group consisting of: porosity; length; diameter; and combinations thereof, which is used to select the implantable device.

25. The imaging system according to claim 1, further comprising at least one guide catheter.

26. The imaging system according to claim 25, wherein the at least one guide catheter comprises an inner diameter between 0.0165" and 0.027".

27. The imaging system according to claim 1, wherein the elongate shaft comprises an inner diameter that varies along the length of the elongate shaft.

28. The imaging system according to claim 1, wherein the elongate shaft comprises an outer diameter between 0.006" to 0.022".

29. The imaging system according to claim 1, wherein the elongate shaft further comprises a middle portion, and wherein the elongate shaft distal portion comprises a larger inner diameter than an inner diameter of the elongate shaft middle portion.

30. The imaging system according to claim 29, wherein the elongate shaft distal portion positioned about the optical assembly and the shear-thinning fluid comprises a wall thickness that is less than the elongate shaft middle portion wall thickness.

31. The imaging system according to claim 1, wherein the imaging probe further comprises a torque shaft with a proximal end and a distal end, and wherein the torque shaft is fixedly attached to the rotatable optical core such that rotation of the torque shaft rotates the rotatable optical core.

32. The imaging system according to claim 31, further comprising a retraction assembly constructed and arranged to retract at least one of the rotatable optical core or the elongate shaft, and wherein the torque shaft distal end is positioned proximal to the retraction assembly.

33. The imaging system according to claim 1, further comprising a rotation assembly constructed and arranged to rotate the rotatable optical core.

34. The imaging system according to claim 1, wherein the console comprises:
   a rotation assembly constructed and arranged to rotate the rotatable optical core; and
   a retraction assembly constructed and arranged to retract at least one of the rotatable optical core or the elongate shaft.

35. The imaging system according to claim 1, wherein the shear-thinning fluid comprises a viscosity between 10 pascal-seconds and 100,000 pascal-seconds.

36. The imaging system according to claim 1, wherein the shear-thinning fluid is configured to reduce in viscosity to a level of approximately 3 pascal-seconds.

37. The imaging system according to claim 1, wherein the shear-thinning fluid is configured to reduce in viscosity to a level of approximately 3 pascal-seconds at a shear rate of $100s^{-1}$.

38. The imaging system according to claim 1, wherein the shear-thinning fluid comprises silicone.

39. The imaging system according to claim 1, wherein the single unitary GRIN lens is constructed and arranged to reflect light from the reflective surface of the single unitary GRIN lens to another surface of the single unitary GRIN lens where the light is output from the single unitary GRIN lens.

40. The imaging system according to claim 1, wherein the shear-thinning fluid is different than the fluid in the lumen of the elongate shaft.

* * * * *